(12) United States Patent
Mavunkel et al.

(10) Patent No.: US 7,238,712 B2
(45) Date of Patent: *Jul. 3, 2007

(54) INDOLE-TYPE DERIVATIVES AS INHIBITORS OF P38 KINASE

(75) Inventors: Babu J. Mavunkel, Sunnyvale, CA (US); Sarvajit Chakravarty, Sunnyvale, CA (US); John J. Perumattam, Los Altos, CA (US); Sundeep Dugar, San Jose, CA (US); Qing Lu, Foster City, CA (US); Xi Liang, Mountain View, CA (US)

(73) Assignee: Scios, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/156,997

(22) Filed: May 28, 2002

(65) Prior Publication Data

US 2003/0195355 A1    Oct. 16, 2003

Related U.S. Application Data

(63) Continuation of application No. 09/575,060, filed on May 19, 2000, now Pat. No. 6,867,209.

(60) Provisional application No. 60/202,608, filed on May 9, 2000, provisional application No. 60/154,594, filed on Sep. 17, 1999.

(51) Int. Cl.
*A61K 31/445* (2006.01)
*C07D 401/06* (2006.01)

(52) U.S. Cl. ............. 514/323; 514/320; 514/321; 514/322; 544/360; 544/370; 546/196; 546/198; 546/199; 546/201

(58) Field of Classification Search ........ 514/321, 514/322, 323, 252, 16, 254.03, 254.11, 320; 546/196, 198, 199, 201; 544/370, 373, 376, 544/377, 360
See application file for complete search history.

(56) References Cited

U.S. PATENT DOCUMENTS

| | | | | |
|---|---|---|---|---|
| 3,316,260 | A | 4/1967 | Shen et al. | 544/143 |
| 4,088,765 | A | 5/1978 | Winn et al. | 514/322 |
| 4,243,806 | A | 1/1981 | Raeymaekers et al. | 544/396 |
| 4,454,130 | A | 6/1984 | Tominaga et al. | 544/363 |
| 4,737,501 | A | 4/1988 | Tominago et al. | 514/253 |
| 4,886,809 | A | 12/1989 | Tamada et al. | 514/321 |
| 5,409,941 | A | 4/1995 | Nowakowski | |
| 5,462,934 | A | 10/1995 | Goto et al. | 514/183 |
| 5,696,122 | A | 12/1997 | Gaster et al. | 514/254 |
| 5,698,553 | A | 12/1997 | Prucher et al. | 514/222.8 |
| 5,714,498 | A | 2/1998 | Kulagowski et al. | 514/307 |
| 5,726,177 | A | 3/1998 | Italazy et al. | 514/253 |
| 5,795,907 | A | 8/1998 | Kalindjian | 514/397 |
| 6,130,235 | A | 10/2000 | Mavunkel et al. | |
| 6,340,685 | B1 | 1/2002 | Mavunkel et al. | |
| 6,410,540 | B1* | 6/2002 | Goehring et al. | 514/252.13 |
| 6,525,042 | B1 | 2/2003 | Kobayashi et al. | |
| 2003/0092717 | A1 | 5/2003 | Dugar et al. | |

FOREIGN PATENT DOCUMENTS

| | | |
|---|---|---|
| EP | 0 318 235 | 5/1989 |
| EP | 0 431 945 | 6/1991 |
| EP | 0 709 384 | 5/1996 |
| EP | 0 831 090 | 3/1998 |

(Continued)

OTHER PUBLICATIONS

Cecil "Textbook of medicine" Sanders, p. 1395-98 (1983).*

(Continued)

*Primary Examiner*—Celia Chang
(74) *Attorney, Agent, or Firm*—Morrison & Foerster LLP

(57) ABSTRACT

The invention is directed to methods to inhibit p38-α kinase using compounds of the formula

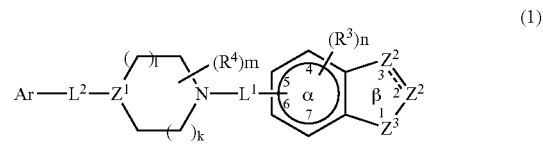

(1)

and the pharmaceutically acceptable salts thereof, or a pharmaceutical composition thereof, wherein $\diagdown$ represents a single or double bond;

one $Z^2$ is CA or $CR^8A$ and the other is $CR^1$, $CR^1_2$, $NR^6$ or N wherein each $R^1$, $R^6$ and $R^8$ is independently hydrogen or noninterfering substituent;

A is $—W_i—COX_jY$ wherein Y is $COR^2$ or an isostere thereof and $R^2$ is hydrogen or a noninterfering substituent, each of W and X is a spacer of 2–6 Å, and each of i and j is independently 0 or 1;

$Z^3$ is $NR^7$ or O;

each $R^3$ is independently a noninterfering substituent;

n is 0–3;

each of $L^1$ and $L^2$ is a linker;

each $R^4$ is independently a noninterfering substituent;

m is 0–4;

$Z^1$ is $CR^5$ or N wherein $R^5$ is hydrogen or a noninterfering substituent;

each of l and k is an integer from 0–2 wherein the sum of l and k is 0–3;

Ar is an aryl group substituted with 0–5 noninterfering substituents, wherein two noninterfering substituents can form a fused ring; and the distance between the atom of Ar linked to $L^2$ and the center of the α ring is 4.5–24 Å.

30 Claims, No Drawings

FOREIGN PATENT DOCUMENTS

| | | | |
|---|---|---|---|
| JP | 61-291566 | * | 12/1986 |
| JP | 2-184673 | | 7/1990 |
| JP | 3-161-470 | | 7/1991 |
| JP | 61-291566 | * | 12/1996 |
| JP | 9-124631 | | 9/1997 |
| WO | WO 96/40143 | | 12/1996 |
| WO | WO 97/26252 | | 7/1997 |
| WO | WO 98/06715 | | 2/1998 |
| WO | WO 98/07425 | | 2/1998 |
| WO | WO 98/28292 | | 7/1998 |
| WO | WO 99/00357 | | 1/1999 |
| WO | WO 99/61426 A | | 12/1999 |
| WO | WO 00/12074 A | | 3/2000 |
| WO | WO 00/59904 | | 3/2000 |
| WO | WO 02/42292 | * | 5/2002 |
| WO | WO 02/44168 | * | 6/2002 |
| WO | WO 02/070491 | * | 6/2002 |
| WO | WO 02/070491 | * | 9/2002 |

OTHER PUBLICATIONS

CRC handbook of chemistry and physics 83rd edition (2002).*
Bennett "Concise ch3mical and technical dictionary" p. 536-537 (1976).*
Grant "Hackh's chemical dictionary" p. 320-321 (1983).*
Adams et al. "Imidazole Compounds . . . " CA 128:201066 (1998).
De Clerck et al. (1981). Throm. Res 23:1-12.
Dukic et al. (1997). Arch. Pharm 330:25-28.
Eyers, P.A. et al. "Conversion of SB 203580-insensitive MAP kinase family members to drug-sensitive forms by a single amino-acid substitution", Chem and Biol (1995) 5:321-328.
Fischer, "Physical chemical properties and local anesthetic results of an ether substitute of procaine" CA 67:10051 (1996).
Gassman, P. G., "A General Method for the Synthesis of Indoles," J. Am. Chem. Soc., (1974) 96(17): 5495-5508.
International Search Report dated Jul. 29, 1999.
Jiang, Y. et al., "Characterization of the structure and function of a new mitogen-activated protein kinase (p38β)" J Biol Chem (1996) 271:17920-17926.
Kumar, S. et al. "Novel homologues of CSBP/p38 MAP kinase: activation, substrate specificity and sensitivity to inhibition by pyridinyl imidazoles", Biochem Biophys Res Comm (1997) 235:533-538.
Li, Z. et al. "The primary structure of p38γ: a new member of p38 group of MAP kinases", Biochem Biophys Res Comm (1996) 228:334-340.

Mittendorf et al. "Preparation of Bis-Benzimidazoles . . . " CA 132:265195 (2000).
Murai, Y., et al., "Synthesis of 4-, 5-, 6- and 7-Substituted N-Tosylindoles from Substituted Anilines," Heterocycles, (1992) 34(5):1017-1029.
Muro et al. "Dihydrobenzofuran Derivatives" CA 88:169949 (1978).
Nakai et al. (1994). CA 121:222012.
Nakai et al. (1994). CA 121:221997.
Oelschlaeger et al. (1988). CA 109:73387.
Ogawa et al. "Studies on Positive Inotropic . . . " CA 110:57613 (1988).
Otsuka Pharm. (1983). CA 100:51465.
Otsuka Pharm. (1983). CA 100:34414.
Otsuka Pharm. (1984). CA 100:68187.
Patani et al. "Bioisosterism: A Rational Approach in Drug Design" Chem. Rev. 96:3147-3176 (1996).
Societe Des Usine Chemiques "Anticancerous 2-Substituted . . . " CA 77:34584 (1968).
Stein, B. et al. "p38-2, a novel mitogen-activated protein kinase with distinct properties", J Biol Chem (1997) 272:19509-19517.
Tamada et al. "Preparation of Benzoheterocycle . . . " CA 111:153834 (1989).
Von Strandtmann. (1971). CA 80:82713.
Wang, X.S., et al., "Molecular cloning and characterization of a novel p38 mitogen-activated protein kinase", J Biol Chem (1997) 272:23668-23674.
Wang, Y. et al., "Cardiac muscle cell hypertrophy and apoptosis induced by distinct members of the p38 mitogen-activated protein kinase family", J Biol Chem (1998) 273:2161-2168.
Burger, "A guide to the chemical basis of drug design" Wiley Interscience, p. 15 (1983).
CAPLUS, accession No. 2000:460222 (Floyd et al.).
Trilateral project "comparative study on reach through claims" Nov. 2001, p. 1.
Wilbrahan et al., "Organic and biological chemistry" Southern Ill. Univ. p. 387 (1984).
Dinarello, Chest (2000) 118(2):503-508.
Hashimoto et al., Clinical and Experimental Allergy (1999-2000) 30:48-55.
Nick et al., J. Clin. Invest. (1997) 99:975-986.
Schmit et al., CA (1994) 122:53913.
Schneider et al., Chemical Abstracts (1996) 127:79417.

* cited by examiner

INDOLE-TYPE DERIVATIVES AS INHIBITORS OF P38 KINASE

This application is a continuation of U.S. Ser. No. 09/575,060, filed 19 May 2000, now U.S. Pat. No. 6,867,209 which claimed priority under 35 U.S.C. § 119(e) to U.S. Ser. No. 60/202,608, filed 9 May 2000 and to U.S. Ser. No. 60/154,594, filed 17 Sep. 1999. Priority was also claimed under 35 U.S.C. § 120 with respect to U.S. Ser. No. 09/316,761 filed 21 May 1999, now U.S. Pat. No. 6,589,955, which is a continuation of U.S. Ser. No. 09/275,176, filed 24 Mar. 1999, now U.S. Pat. No. 6,340,685, which is a continuation-in-part of U.S. Ser. No. 09/128,137, filed Aug. 3, 1998, now U.S. Pat. No. 6,130,235, which claimed the benefit of priority under 35 U.S.C. § 119(e) of U.S. Ser. No. 60/086,531, filed May 22, 1998. The contents of these applications are incorporated herein by reference in their entirety.

FIELD OF THE INVENTION

The invention relates to treating various disorders associated with enhanced activity of kinase p38-α. More specifically, it concerns compounds that are related to indole-type derivatives coupled to piperazine- or piperidine-type moieties as useful in these methods.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful anti-inflammatory agents.

Eye diseases associated with a fibroproliferative condition include retinal reattachment surgery accompanying proliferative vitreoretinopathy, cataract extraction with intraocular lens implantation, and post glaucoma drainage surgery.

PCT applications WO98/06715, WO98/07425, and WO96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine ring linked through a carboxamide linkage. Additional compounds which are conjugates of piperazines with indoles are described as insecticides in WO97/26252, also incorporated herein by reference.

Certain aroyl/phenyl-substituted piperazines and piperidines which inhibit p38-α kinase are described in PCT publication WO00/12074 published Mar. 9, 2000. In addition, indolyl substituted piperidines and piperazines which inhibit this enzyme are described in PCT publication No. WO99/61426 published Dec. 2, 1999. Carbolene derivatives of piperidine and piperazine as p38-α inhibitors are described in PCT/US00/07934 filed Mar. 24, 2000.

None of the foregoing patents describes the indole derivatives described herein which specifically inhibit p38-α.

DISCLOSURE OF THE INVENTION

The invention is directed to methods and compounds useful in treating conditions that are characterized by enhanced p38-α activity. These conditions include inflammation, proliferative diseases, and certain cardiovascular disorders as well as Alzheimer's disease as further described below.

Compounds of the invention have been found to inhibit p38 kinase, the α-isoform in particular, and are thus useful in treating diseases mediated by these activities. The compounds of the invention are of the formula

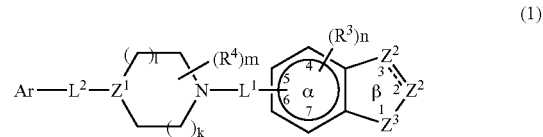

(1)

and the pharmaceutically acceptable salts thereof, or a pharmaceutical composition thereof, wherein ⟋⟍ represents a single or double bond;

one $Z^2$ is CA or $CR^8A$ and the other is $CR^1$, $CR^1_2$, $NR^6$ or N wherein each $R^1$, $R^6$ and $R^8$ is independently hydrogen or noninterfering substituent;

A is $—W_i—COX_jY$ wherein Y is $COR^2$ or an isostere thereof and $R^2$ is hydrogen or a noninterfering substituent, each of W and X is a spacer of 2–6 Å, and each of i and j is independently 0 or 1;

$Z^3$ is $NR^7$ or O;

each $R^3$ is independently a noninterfering substituent;

n is 0–3;

each of $L^1$ and $L^2$ is a linker;

each $R^4$ is independently a noninterfering substituent;

m is 0–4;

$Z^1$ is $CR^5$ or N wherein $R^5$ is hydrogen or a noninterfering substituent;

each of l and k is an integer from 0–2 wherein the sum of l and k is 0–3;

Ar is an aryl group substituted with 0–5 noninterfering substituents, wherein two noninterfering substituents can form a fused ring; and the distance between the atom of Ar linked to $L^2$ and the center of the α ring is 4.5–24 Å.

The invention is directed to methods of treating inflammation or proliferative conditions using these compounds. The invention is also directed to treating conditions associated with cardiac failure and Alzheimer's disease using the invention compounds.

MODES OF CARRYING OUT THE INVENTION

The compounds of formula (1) are useful in treating conditions which are characterized by overactivity of p38 kinase, in particular the α-isoform. Conditions "characterized by enhanced p38-α activity" include those where this enzyme is present in increased amount or wherein the enzyme has been modified to increase its inherent activity, or both. Thus, "enhanced activity" refers to any condition wherein the effectiveness of these proteins is undesirably high, regardless of the cause.

The compounds of the invention are useful in conditions where p38-α kinase shows enhanced activity. These conditions are those in which fibrosis and organ sclerosis are caused by, or accompanied by, inflammation, oxidation injury, hypoxia, altered temperature or extracellular osmolarity, conditions causing cellular stress, apoptosis or necrosis. These conditions include ischemia-reperfusion injury, congestive heart failure, progressive pulmonary and bronchial fibrosis, hepatitis, arthritis, inflammatory bowel disease, glomerular sclerosis, interstitial renal fibrosis, chronic scarring diseases of the eyes, bladder and reproductive tract, bone marrow dysplasia, chronic infectious or autoimmune states and traumatic or surgical wounds. These conditions, of course, would be benefited by compounds which inhibit p38-α. Methods of treatment with the compounds of the invention are further discussed below.

The Invention Compounds

The compounds useful in the invention are derivatives of indole-type compounds containing a mandatory substituent, A, at a position corresponding to the 2- or 3-position of indole. In general, an indole-type nucleus is preferred, although alternatives within the scope of the invention are also illustrated below.

In the description above, certain positions of the molecule are described as permitting "noninterfering substituents." This terminology is used because the substituents in these positions generally speaking are not relevant to the essential activity of the molecule taken as a whole. A wide variety of substituents can be employed in these positions, and it is well within ordinary skill to determine whether any particular arbitrary substituent is or is not "noninterfering."

As used herein, a "noninterfering substituent" is a substituent which leaves the ability of the compound of formula (1) to inhibit p38-α activity qualitatively intact. Thus, the substituent may alter the degree of inhibition of p38-α. However, as long as the compound of formula (1) retains the ability to inhibit p38-α activity, the substituent will be classified as "noninterfering." A number of assays for determining the ability of any compound to inhibit p38-α activity are available in the art. A whole blood assay for this evaluation is illustrated below: the gene for p38-α has been cloned and the protein can be prepared recombinantly and its activity assessed, including an assessment of the ability of an arbitrarily chosen compound to interfere with this activity. The essential features of the molecule are tightly defined. The positions which are occupied by "noninterfering substituents" can be substituted by conventional organic moieties as is understood in the art. It is irrelevant to the present invention to test the outer limits of such substitutions. The essential features of the compounds are those set forth with particularity herein.

In addition, $L^1$ and $L^2$ are described herein as linkers. The nature of such linkers is less important that the distance they impart between the portions of the molecule. Typical linkers include alkylene or alkenylene—i.e., an alkylene moiety which contains a double bond, including a double bond at one terminus. Other suitable linkers include, for example, substituted alkylenes or alkenylenes, carbonyl moieties, and the like.

As used herein, "hydrocarbyl residue" refers to a residue which contains only carbon and hydrogen. The residue may be aliphatic or aromatic, straight-chain, cyclic, branched, saturated or unsaturated. The hydrocarbyl residue, when so stated however, may contain heteroatoms over and above the carbon and hydrogen members of the substituent residue. Thus, when specifically noted as containing such heteroatoms, the hydrocarbyl residue may also contain carbonyl groups, amino groups, hydroxyl groups and the like, or contain heteroatoms within the "backbone" of the hydrocarbyl residue.

As used herein, "inorganic residue" refers to a residue that does not contain carbon. Examples include, but are not limited to, halo, hydroxy, $NO_2$ or $NH_2$.

As used herein, the term "alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the like. Typically, the alkyl, alkenyl and alkynyl substituents contain 1–10C (alkyl) or 2–10C (alkenyl or alkynyl). Preferably they contain 1–6C (alkyl) or 2–6C (alkenyl or alkynyl). Heteroalkyl, heteroalkenyl and heteroalkynyl are similarly defined but may contain 1–2 O, S or N heteroatoms or combinations thereof within the backbone residue.

As used herein, "acyl" encompasses the definitions of alkyl, alkenyl, alkynyl and the related hetero-forms which are coupled to an additional residue through a carbonyl group.

"Aromatic" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5–12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1–6C. These carbon chains may also include a carbonyl group, thus making them able to provide substituents as an acyl moiety.

When the compounds of Formula 1 contain one or more chiral centers, the invention includes optically pure forms as well as mixtures of stereoisomers or enantiomers With respect to the portion of the compound between the atom of Ar bound to $L^2$ and ring α, $L^1$ and $L^2$ are linkers which space the substituent Ar from ring α at a distance of 4.5–24 Å, preferably 6–20 Å, more preferably 7.5–10 Å. The distance is measured from the center of the α ring to the atom of Ar to which the linker $L^2$ is attached. Typical, but nonlimiting, embodiments of $L^1$ and $L^2$ are CO and isosteres thereof, or optionally substituted isosteres, or longer chain forms. $L^2$, in particular, may be alkylene or alkenylene optionally substituted with noninterfering substituents or $L^1$ or $L^2$ may be or may include a heteroatom such as N, S or O. Such substituents include, but are not limited to, a moiety selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein two substituents on $L^2$ can be joined to form a non-aromatic saturated or unsaturated ring that includes 0–3 heteroatoms which are O, S and/or N and which contains 3 to 8 members or said two substituents can be joined to form a carbonyl moiety or an oxime, oximeether, oximeester or ketal of said carbonyl moiety.

Isosteres of CO and $CH_2$, include SO, $SO_2$, or CHOH. CO and $CH_2$ are preferred.

Thus, $L^2$ is substituted with 0–2 substituents. Where appropriate, two optional substituents on $L^2$ can be joined to form a non-aromatic saturated or unsaturated hydrocarbyl ring that includes 0–3 heteroatoms such as O, S and/or N and which contains 3 to 8 members. Two optional substituents on $L^2$ can be joined to form a carbonyl moiety which can be subsequently converted to an oxime, an oximeether, an oximeester, or a ketal.

Ar is aryl, heteroaryl, including 6-5 fused heteroaryl, cycloaliphatic or cycloheteroaliphatic that can be optionally substituted. Ar is preferably optionally substituted phenyl.

Each substituent on Ar is independently a hydrocarbyl residue (1–20C) containing 0–5 heteroatoms selected from O, S and N, or is an inorganic residue. Preferred substituents include those selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein two of said optional substituents on adjacent positions can be joined to form a fused, optionally substituted aromatic or nonaromatic, saturated or unsaturated ring which contains 3–8 members. More preferred substituents include halo, alkyl (1–4C) and more preferably, fluoro, chloro and methyl. These substituents may occupy all available positions of the aryl ring of Ar, preferably 1–2 positions, most preferably one position. These substituents may be optionally substituted with substituents similar to those listed. Of course some substituents, such as halo, are not further substituted, as known to one skilled in the art.

Two substituents on Ar can be joined to form a fused, optionally substituted aromatic or nonaromatic, saturated or unsaturated ring which contains 3–8 members.

Between $L^1$ and $L^2$ is a piperidine-type moiety of the following formula:

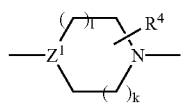

$Z^1$ is $CR^5$ or N wherein $R^5$ is H or a noninterfering substituent. Each of l and k is an integer from 0–2 wherein the sum of l and k is 0–3. The noninterfering substituents $R^5$ include, without limitation, halo, alkyl, alkoxy, aryl, arylalkyl, aryloxy, heteroaryl, acyl, carboxy, or hydroxy. Preferably, $R^5$ is H, alkyl, OR, $NR_2$, SR or halo, where R is H or alkyl. Additionally, $R^5$ can be joined with an $R^4$ substituent to form an optionally substituted non-aromatic saturated or unsaturated hydrocarbyl ring which contains 3–8 members and 0–3 heteroatoms such as O, N and/or S. Preferred embodiments include compounds wherein $Z^1$ is CH or N, and those wherein both l and k are 1.

$R^4$ represents a noninterfering substituent such as a hydrocarbyl residue (1–20C) containing 0–5 heteroatoms selected from O, S and N. Preferably $R^4$ is ailcyl, alkoxy, aryl, arylalkyl, aryloxy, heteroalkyl, heteroaryl, heteroarylalkyl, RCO, =O, acyl, halo, CN, OR, NRCOR, NR, wherein R is H, alkyl (preferably 1–4C), aryl, or hetero forms thereof. Each appropriate substituent is itself unsubstituted or substituted with 1–3 substituents. The substituents are preferably independently selected from a group that includes alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof and two of $R^4$ on adjacent positions can be joined to form a fused, optionally substituted aromatic or nonaromatic, saturated or unsaturated ring which contains 3–8 members, or $R^4$ is =O or an oxime, oximeether, oximeester or ketal thereof. $R^4$ may occur m times on the ring; m is an integer of 0–4. Preferred embodiments of $R^4$ comprise alkyl (1–4C) especially two alkyl substituents and carbonyl. Most preferably $R^4$ comprises two methyl groups at positions 2 and 5 or 3 and 6 of a piperidinyl or piperazinyl ring or =O preferably at the 5-position of the ring. The substituted forms may be chiral and an isolated enantiomer may be preferred.

$R^3$ also represents a noninterfering substituent. Such substituents include hydrocarbyl residues (1–6C) containing 0–2 heteroatoms selected from O, S and/or N and inorganic residues. n is an integer of 0–3, preferably 0 or 1. Preferably, the substituents represented by $R^3$ are independently halo, alkyl, heteroalkyl, OCOR, OR, NRCOR, SR, or $NR_2$, wherein R is H, alkyl, aryl, or heteroforms thereof. More preferably $R^3$ substituents are selected from alkyl, alkoxy or halo, and most preferably methoxy, methyl, and chloro. Most preferably, n is 0 and the α ring is unsubstituted, except for $L^1$ or n is 1 and $R^3$ is halo or methoxy.

In the ring labeled β, $Z^3$ may be $NR^7$ or O—i.e., the compounds may be related to indole or benzofuran. If $C^3$ is $NR^7$, preferred embodiments of $R^7$ include H or optionally substituted alkyl, alkenyl, alkynyl, aryl, arylalkyl, acyl, aroyl, heteroaryl, heteroalkyl, heteroalkenyl, heteroalkynyl, heteroalkylaryl, or is SOR, $SO_2R$, RCO, COOR, alkyl-COR, $SO_3R$, $CONR_2$, $SO_2NR_2$, CN, $CF_3$, $NR_2$, OR, alkyl-SR, alkyl-SOR, alkyl-$SO_2R$, alkyl-OCOR, alkyl-COOR, alkyl-CN, alkyl-$CONR_2$, or $R_3Si$, wherein each R is independently H, alkyl, alkenyl or aryl or heteroforms thereof. More preferably, $R^7$ is hydrogen or is alkyl (1–4C), preferably methyl or is acyl (1–4C), or is COOR wherein R is H, alkyl, alkenyl of aryl or hetero forms thereof. $R^7$ is also preferably a substituted alkyl wherein the preferred substituents are form ether linkages or contain sulfinic or sulfonic acid moieties. Other preferred substituents include sulfhydryl substituted alkyl substituents. Still other preferred substituents include $CONR_2$ wherein R is defined as above.

It is preferred that the indicated dotted line represents a double bond; however, compounds which contain a saturated β ring are also included within the scope of the invention.

Preferably, the mandatory substituent CA or $CR^8A$ is in the 3-position; regardless of which position this substituent occupies, the other position is $CR^1$, $CR^1{}_2$, $NR^6$ or N. $CR^1$ is preferred. Preferred embodiments of $R^1$ include hydrogen, alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof and two of $R^1$ can be joined to form a fused, optionally substituted aromatic or nonaromatic, saturated or unsaturated ring which contains 3–8 members. Most preferably, $R^1$ is H, alkyl, such as methyl, most preferably, the ring labeled α contains a double bond and $CR^1$ is CH or C-alkyl. Other preferable forms of $R^1$ include H, alkyl, acyl, aryl, arylalkyl, heteroallcyl, heteroaryl, halo, OR, $NR_2$, SR, NRCOR, alkyl-OOCR, RCO, COOR, and CN, wherein each R is independently H, alkyl, or aryl or heteroforms thereof.

While the position not occupied by CA is preferred to include $CR^1$, the position can also be N or $NR^6$. While $NR^6$ is less preferred (as in that case the ring labeled β would be saturated), if $NR^6$ is present, preferred embodiments of $R^6$ include H, or alkyl, alkenyl, alkynyl, aryl, arylalkyl, acyl, aroyl, heteroaryl, heteroalkyl, heteroalkenyl, heteroalkynyl, heteroalkylaryl, or is SOR, $SO_2R$, RCO, COOR, alkyl-COR, $SO_3R$, $CONR_2$, $SO_2NR_2$, CN, $CF_3$, or $R_3Si$ wherein each R is independently H, alkyl, alkenyl or aryl or heteroforms thereof.

Preferably, $CR^8A$ or CA occupy position 3- and preferably $Z^2$ in that position is CA. However, if the β ring is saturated and $R^8$ is present, preferred embodiments for $R^8$ include H, halo, alkyl, alkenyl and the like. Preferably $R^8$ is a relatively small substituent corresponding, for example, to H or lower alkyl 1–4C.

A is $-W_i-COX_jY$ wherein Y is $COR^2$ or an isostere thereof and $R^2$ is a noninterfering substitent. Each of W and X is a spacer and may be, for example, optionally substituted alkyl, alkenyl, or alkynyl, each of i and j is 0 or 1. Preferably, W and X are unsubstituted. Preferably, j is 0 so that the two carbonyl groups are adjacent to each other. Preferably, also, i is 0 so that the proximal CO is adjacent the ring. However, compounds wherein the proximal CO is spaced from the ring can readily be prepared by selective reduction of an initially glyoxal substituted β ring. In the most preferred embodiments of the invention, the α/β ring system is an indole containing CA in position 3- and wherein A is $COCR^2$.

The noninterfering substituent represented by $R^2$, when $R^2$ is other than H, is a hydrocarbyl residue (1–20C) containing 0–5 heteroatoms selected from O, S and/or N or is an inorganic residue. Preferred are embodiments wherein $R^2$ is H, or is straight or branched chain alkyl, alkenyl, alkynyl, aryl, arylalkyl, heteroalkyl, heteroaryl, or heteroarylalkyl, each optionally substituted with halo, alkyl, heteroalkyl, SR, OR, $NR_2$, OCOR, NRCOR, $NRCONR_2$, $NRSO_2R$, $NRSO_2NR_2$, $OCONR_2$, CN, COOR, $CONR_2$, COR, or $R_3Si$ wherein each R is independently H, alkyl, alkenyl or aryl or the heteroatom-containing forms thereof, or wherein $R^2$ is OR, $NR_2$, SR, $NRCONR_2$, $OCONR_2$, or $NRSO_2NR_2$, wherein each R is independently H, alkyl, alkenyl or aryl or the heteroatom-containing forms thereof, and wherein two R attached to the same atom may form a 3–8 member ring and wherein said ring may further be substituted by alkyl, alkenyl, alkynyl, aryl, arylalkyl, heteroalkyl, heteroaryl, heteroarylalkyl, each optionally substituted with halo, SR, OR, $NR_2$, OCOR, NRCOR, $NRCONR_2$, $NRSO_2R$, $NRSO_2NR_2$, $OCONR_2$, or $R_3Si$ wherein each R is independently H, alkyl, alkenyl or aryl or the heteroatom-containing forms thereof wherein two R attached to the same atom may form a 3–8 member ring, optionally substituted as above defined.

Other preferred embodiments of $R^2$ are H, heteroarylalkyl, $-NR_2$, heteroaryl, $-COOR$, $-NRNR_2$, heteroaryl-COOR, heteroaryloxy, $-OR$, heteroaryl-$NR_2$, $-NROR$ and alkyl. Most preferably $R^2$ is isopropyl piperazinyl, methyl piperazinyl, dimethylamine, piperazinyl, isobutyl carboxylate, oxycarbonylethyl, morpholinyl, aminoethyldimethylamine, isobutyl carboxylate piperazinyl, oxypiperazinyl, ethylcarboxylate piperazinyl, methoxy, ethoxy, hydroxy, methyl, amine, aminoethyl pyrrolidinyl, aminopropanediol, piperidinyl, pyrrolidinyl-piperidinyl, or methyl piperidinyl.

Isosteres of $COR^2$ as represented by Y are defined as follows.

The isosteres have varying lipophilicity and may contribute to enhanced metabolic stability. Thus, Y, as shown, may be replaced by the isosteres in Table 1.

TABLE 1

Acid Isosteres

| Names of Groups | Chemical Structures | Substitution Groups (SG) |
|---|---|---|
| tetrazole | (structure) | n/a |
| 1,2,3-triazole | (structure) | H; $SCH_3$; $COCH_3$; Br; $SOCH_3$; $SO_2CH_3$; $NO_2$; $CF_3$; CN; COOMe |
| 1,2,4-triazole | (structure) | H; $SCH_3$; $COCH_3$; Br; $SOCH_3$; $SO_2CH_3$; $NO_2$ |
| imidazole | (structure) | H; $SCH_3$; $COCH_3$; Br; $SOCH_3$; $SO_2CH_3$; $NO_2$ |

Thus, isosteres include tetrazole, 1,2,3-triazole, 1,2,4-triazole and imidazole.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation.

Synthesis of the Invention Compounds

The following Reaction Scheme is illustrative of the conversion of a 4-benzyl piperidinyl-indole-5-carboxamide to the glyoxalic acid compounds of the invention and derivatives thereof.

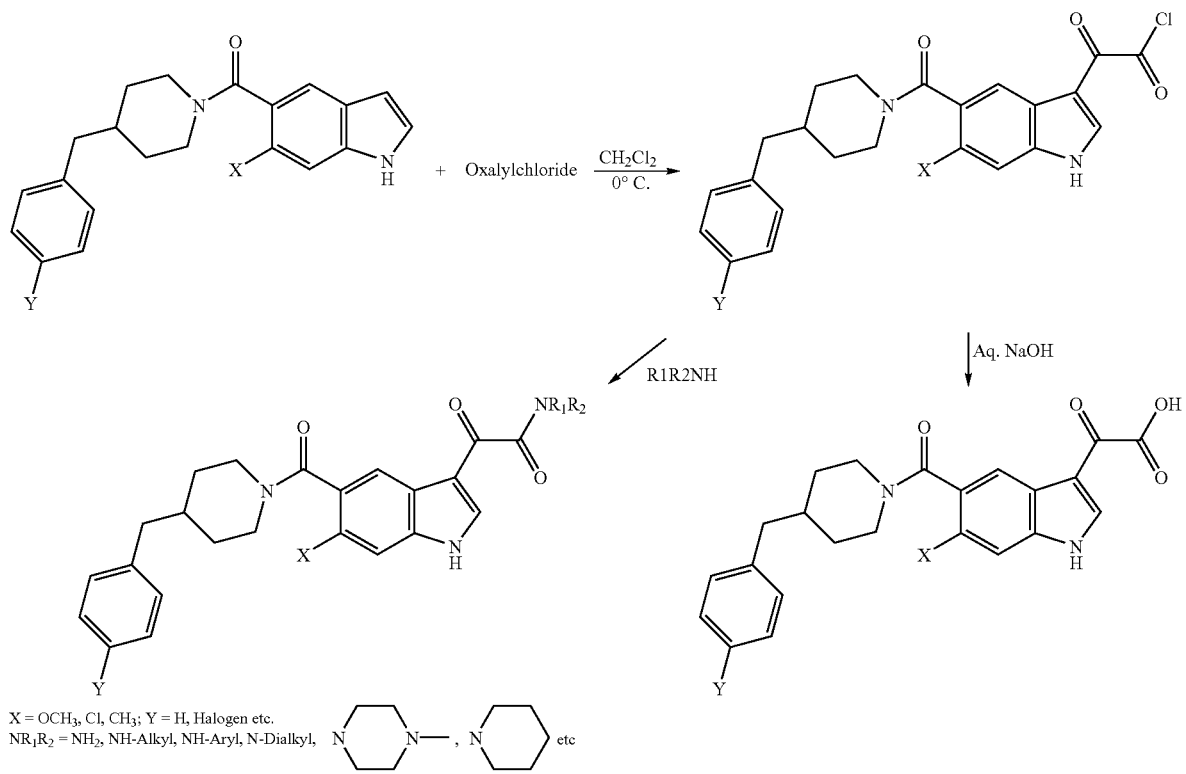

X = OCH₃, Cl, CH₃; Y = H, Halogen etc.
NR₁R₂ = NH₂, NH-Alkyl, NH-Aryl, N-Dialkyl, etc.

Of course, the 4-benzyl piperidinyl carbonyl of the illustration at position 5 may be generalized as

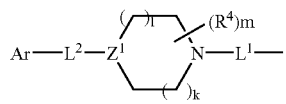

and the glyoxal type substituent at position 3 can be generalized to $W_iCOX_jY$.

Similarly, embodiments wherein the indole-type moiety is

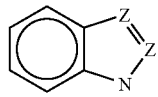

can be used in these schemes. Methods to synthesize the compounds of the invention are, in general, known in the art. The following general schemes illustrate such methods.

Scheme 1

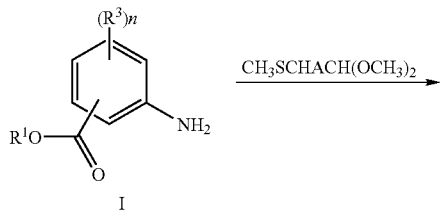

-continued

Substituted amino benzoic acid esters such as I can be treated with reagents such as thiomethylacetaldehyde dimethyl acetal and N-chlorosuccinamide in methylene chloride at low temperature followed by the treatment with a base such as triethylamine at reflux in methylene chloride, dichloroethane or chloroform to give indoles II, Scheme 1. Treatment with reagents such as Raney-Nickel in an appropriate solvent such as ethanol, methanol or isopropanol will yield the corresponding indole carboxylic acid ester which when hydrolyzed under base conditions will give the desired substituted indole carboxylic acid.

Scheme 2

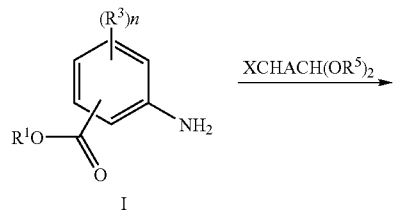

Alternatively, substituted amino benzoic acid esters I can be converted to the ketals IV, Scheme 2, with an appropriate aldehyde under conditions of reductive alkylation with reagents such as sodium triacetoxyborohydride in acetic acid in the presence of sodium sulfate. The amines can then be treated with lewis acids such as aluminum chloride, titanium chloride, $BF_3$-etherate in dichloromethane or dichloroethane, under reflux to give the corresponding substituted indole methyl esters, with appropriate substitutions.

Scheme 3

Another method could involve the treatment of the substituted amino benzoic acid esters I with iodine and sodium periodate in an appropriate solvent such as dimethyformamide, to give the corresponding iodo aniline V, Scheme 3. This can be coupled with an acetylene such as trimethyl silyl acetylene or ethylethynyl ether in the presence of an appropriate catalysts such as palladium and copper and a base such as triethylamine to give the silyl coupled product such as VI. Subsequent cyclization in a solvent such as dimethylformamide and in the presence of a catalyst such as copper iodide would give the appropriately substituted indoles VII.

Scheme 4

Synthesis of the required piperidines can be achieved by treating an appropriate piperidone such as VIII, Scheme 4, with substituted benzyl phosphonate esters in the presence of a base such as sodium hydride to give alkenes which can be reduced to the corresponding substituted 4-benzylpiperidine such as IX. The hydrogenations are typically done in the presence of catalytic metals in solvents such as methanol, ethanol and ethyl acetate.

Scheme 5

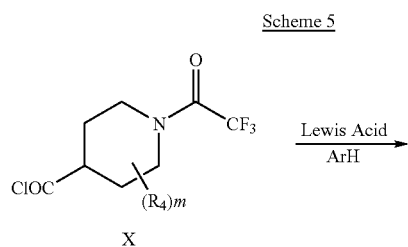

An alternate method could involve isonipecotoyl chlorides such as X which can be used to acylate appropriately substituted benzenes (ArH) in the presence of a lewis acid such as aluminum chloride to give the ketones XI, Scheme 5. Further modifications of the carbonyl moiety of XI using methods and routes generally known can then lead to the desired compounds XII.

Scheme 6

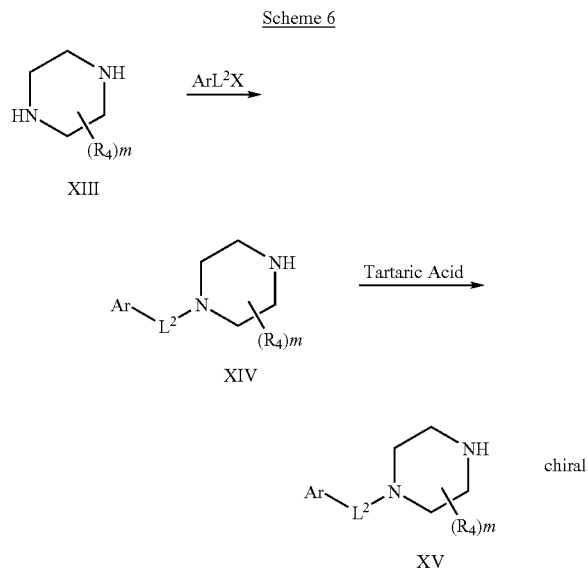

Substituted piperazines can be reacted with various and appropriate ArL²X in the presence or absence of a base or other catalytic reagent to give the substituted piperazines XV, Scheme 6. These can be further resolved to the chiral components with the use a chiral resolving agent such as tartaric acid to give either enantiomers of the substituted piperazines XV.

Scheme 7

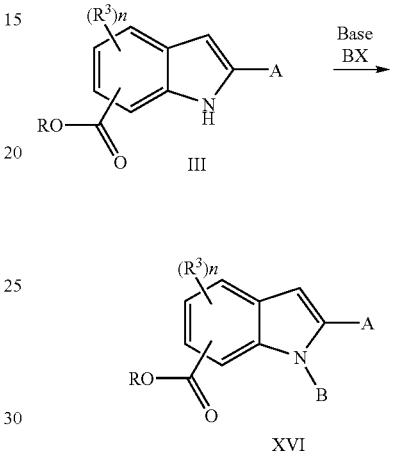

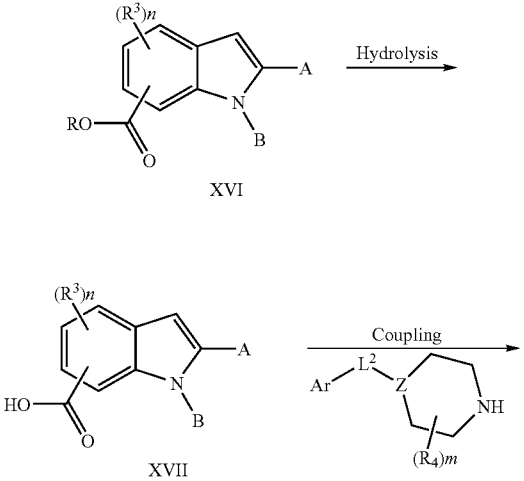

Compounds III can be treated with halides, acid chlorides and other electrophiles (BX), Scheme 7, containing a variety of different substituents, in the presence of a base such as sodium hydride, in a variety of different solvents, to give compounds of type XVI. These can then be converted to the corresponding acids XVII by treatment with appropriate reagents such as an aqueous base. The acids are then coupled to substituted amines IX, XII or XV using a coupling agent such as EDAC.HCl in a variety of solvents including methylene chloride, dimethyl formamide, to give compounds XVIII.

Scheme 8

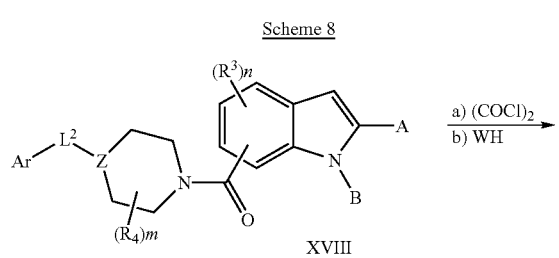

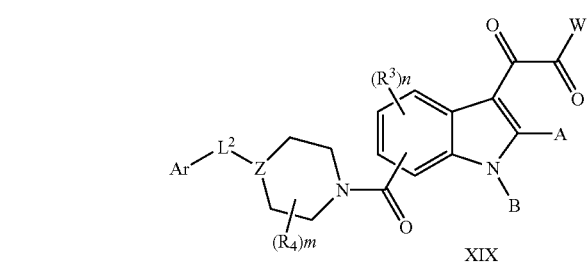

Compounds XVIII can be first treated with acid chlorides such as oxalyl chloride in methylene chloride under anhydrous conditions followed by treatment with a variety of nucelophiles WH to give compounds of type XIX, Scheme 8.

Scheme 9

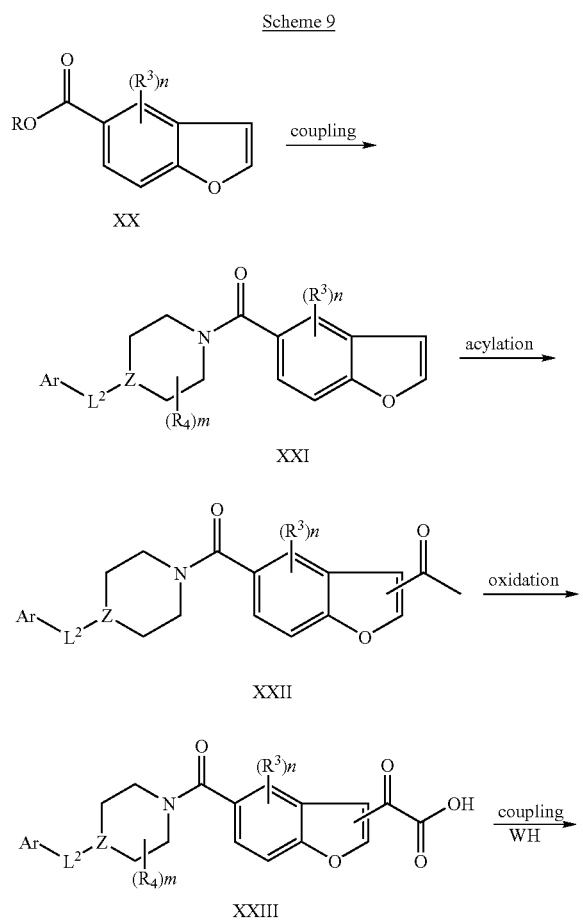

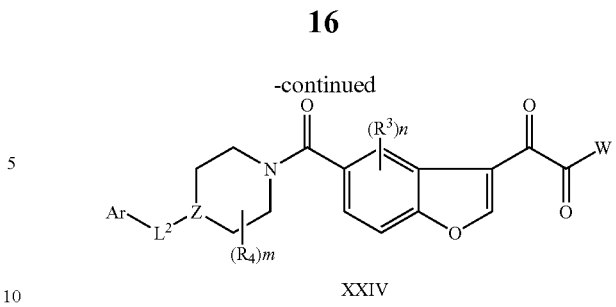

Compounds of type XXIV can be synthesized starting with the appropriately substituted benzofurans of type XX and coupling them with amines IX, XII or XV in the presence of relevant coupling reagents to give compounds XXI, Scheme 9. Subsequent acylation to XXII can be achieved with an acylating agent such as acetic anhydride in the presence of a catalyst such as Fe(III). Oxidation of the acetyl moiety of XXII to the glyoxalic acid moiety of XXIII can be accomplished using an oxidizing agent such as selenium dioxide (Ref: F Da Settimo et al. Eur. J. Med. Chem (1996), 31, 951–956; M. C. Cook, et al. (1975) Br patent 1,399,089; E. Campaigne, et al. J. Med. Chem. (1965), 136–137). Finally coupling of the acid with the appropriate neucleophile in WH can be achieved using any one of the variety of coupling agents known in a variety of solvents to give compounds of type XXIV.

Assays for p38 α Kinase Inhibition

For each of the assay procedures described below, the TNF-α production correlates to the activity of p38-α kinase.

A. Human Whole Blood Assay for p38 Kinase Inhibition

Venous blood is collected from healthy male volunteers into a heparinized syringe and is used within 2 hours of collection. Test compounds are dissolved in 100% DMSO and 1 µl aliquots of drug concentrations ranging from 0 to 1 mM are dispensed into quadruplicate wells of a 24-well microtiter plate (Nunclon Delta SI, Applied Scientific, So. San Francisco, Calif.). Whole blood is added at a volume of 1 ml/well and the mixture is incubated for 15 minutes with constant shaking (Titer Plate Shaker, Lab-Line Instruments, Inc., Melrose Park, Ill.) at a humidified atmosphere of 5% $CO_2$ at 37° C. Whole blood is cultured either undiluted or at a final dilution of 1:10 with RPMI 1640 (Gibco 31800+ $NaHCO_3$, Life Technologies, Rockville, Md. and Scios, Inc., Sunnyvale, Calif.). At the end of the incubation period, 10 µl of LPS (*E. coli* 0111:B4, Sigma Chemical Co., St. Louis, Mo.) is added to each well to a final concentration of 1 or 0.1 µg/ml for undiluted or 1:10 diluted whole blood, respectively. The incubation is continued for an additional 2 hours. The reaction is stopped by placing the microtiter plates in an ice bath and plasma or cell-free supernates are collected by centrifugation at 3000 rpm for 10 minutes at 4° C. The plasma samples are stored at −80° C. until assayed for TNF-α levels by ELISA, following the directions supplied by Quantikine Human TNF-α assay kit (R&D Systems, Minneapolis, Minn.).

$IC_{50}$ values are calculated using the concentration of inhibitor that causes a 50% decrease as compared to a control.

B. Enriched Mononuclear Cell Assay for p38 Kinase Inhibition

The enriched mononuclear cell assay, the protocol of which is set forth below, begins with cryopreserved Human Peripheral Blood Mononuclear Cells (HPBMCs) (Clonetics Corp.) that are rinsed and resuspended in a warm mixture of cell growth media. The resuspended cells are then counted and seeded at $1\times10^6$ cells/well in a 24-well microtitre plate. The plates are then placed in an incubator for an hour to allow the cells to settle in each well.

After the cells have settled, the media is aspirated and new media containing 100 ng/ml of the cytokine stimulatory factor Lipopolysaccharide (LPS) and a test chemical HPBMCs, LPS and a test chemical compound. The cells are then incubated for 2 hours, and the amount of the cytokine Tumor Necrosis Factor Alpha (TNF-α) is measured using an Enzyme Linked Immunoassay (ELISA). One such ELISA for detecting the levels of TNF-α is commercially available from R&D Systems. The amount of TNF-α production by the HPBMCs in each well is then compared to a control well to determine whether the chemical compound acts as an inhibitor of cytokine production.

LPS Induced Cytokine Synthesis in HPBMCs
Cryopreserved HPBMC (cat#CC-2702 Clonetics Corp)
LGM-3 media (cat#CC-3212 Clonetics Corp)
LPS stock 10 µg/ml (Cat. No. L 2630 serotype 0111:B4 Sigma)
Human TNF-α ELISA (R&D Systems)
DNase I (10 mg/ml stock)
Preparation of Cells.
LGM-3 media warmed to 37° C.
5 µl of DNase I stock added to 10 ml media.
Cells thawed rapidly and dispersed into above.
Centrifuge 200×g×10 min @ RT.
Pellet up in 10 ml sterile PBS.
Centrifuge 200×g×10 min @ RT.
Pellet resuspended in 10 ml LGM-3 then diluted to 50 ml with LGM-3.
Perform cell count.
Adjust to 1×E06 cells/well.
Seed 1 ml/well of a 24 well plate.
Place plate in incubator to plate down for 1 hour.
Preparation of Incubation Media.
LGM-3 containing 100 ng/ml LPS (e.g. 50 ml media plus 0.5 ml LPS stock)
Aliquot into 2 ml aliquots and add 1000× inhibitor dilutions.
Incubation
When cells have plated down aspirate media away and overlay with 1 ml relevant incubation media. Return plate to incubator for 2 hours or 24 hours. Remove supernatants after incubation to a labeled tube and either perform TNF (or other) ELISA immediately or freeze for later assay.

$IC_{50}$ values are calculated using the concentration of inhibitor that causes a 50% decrease as compared to a control.

Administration and Use

The compounds of the invention are useful among other indications in treating conditions associated with inflammation. Thus, the compounds of formula (1) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of the invention inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of the invention are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as Alzheimer's, coronary artery disease, congestive heart failure, cardiomyopathy, myocarditis, vasculitis, restenosis, such as occurs following coronary angioplasty, atherosclerosis, IBD, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, Gram-negative sepsis, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs. host disease, bone resorption diseases like osteoporosis, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38-α, p38-β, p38-γ and p38-δ. Jiang, Y., et al., *J Biol Chem* (1996) 271:17920–17926 reported characterization of p38-β as a 372-amino acid protein closely related to p38-α. In comparing the activity of p38-α with that of p38-β, the authors state that while both are activated by proinflammatory cytokines and environmental stress, p38-β was preferentially activated by MAP kinase kinase-6 (MKK6) and preferentially activated transcription factor 2, thus suggesting that separate mechanisms for action may be associated with these forms.

Kumar, S., et al., *Biochem Biophys Res Comm* (1997) 235:533–538 and Stein, B., et al., *J Biol Chem* (1997) 272:19509–19517 reported a second isoform of p38-β, p38-β2, containing 364 amino acids with 73% identity to p38-α. All of these reports show evidence that p38-β is activated by proinflammatory cytokines and environmental stress, although the second reported p38-β isoform, p38-β2, appears to be preferentially expressed in the CNS, heart and skeletal muscle compared to the more ubiquitous tissue expression of p38-α. Furthermore, activated transcription factor-2 (ATF-2) was observed to be a better substrate for p38-β2 than for p38-α, thus suggesting that separate mechanisms of action may be associated with these forms. The physiological role of p38-β1 has been called into question by the latter two reports since it cannot be found in human tissue and does not exhibit appreciable kinase activity with the substrates of p38-α.

The identification of p38-γ was reported by Li, Z., et al., *Biochem Biophys Res Comm* (1996) 228:334–340 and of p38-δ by Wang, X., et al., *J Biol Chem* (1997) 272:23668–23674 and by Kumar, S., et al., *Biochem Biophys Res Comm* (1997) 235:533–538. The data suggest that these two p38 isoforms (γ and δ) represent a unique subset of the MAPK family based on their tissue expression patterns, substrate utilization, response to direct and indirect stimuli, and susceptibility to kinase inhibitors.

Various results with regard to response to drugs targeting the p38 family as between p38-α and either the putative p38-β1 or p38-β2 or both were reported by Jiang, Kumar, and Stein cited above as well as by Eyers, P. A., et al., *Chem and Biol* (1995) 5:321–328. An additional paper by Wang, Y., et al., *J Biol Chem* (1998) 273:2161–2168 suggests the significance of such differential effects. As pointed out by Wang, a number of stimuli, such as myocardial infarction, hypertension, valvular diseases, viral myocarditis, and dilated cardiomyopathy lead to an increase in cardiac workload and elevated mechanical stress on cardiomyocytes. These are said to lead to an adaptive hypertrophic response which, if not controlled, has decidedly negative consequences. Wang cites previous studies which have shown that in ischemia reperfusion treated hearts, p38 MAPK activities are elevated in association with hypertrophy and programmed cell death. Wang shows in the cited paper that activation of p38-β activity results in hypertrophy, whereas activation of p38-α activity leads to myocyte apoptosis. Thus, selective inhibition of p38-α activity as compared to p38-β activity will be of benefit in treating conditions associated with cardiac failure. These conditions include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

Thus, the invention encompasses the use of compounds which selectively inhibit the activity of the p38-α isoform for treating conditions associated with activation of p38-α, in particular those associated with cardiac hypertrophy, ischemia or other environmental stress such as oxidation injury, hyperosmolarity or other agents or factors that activate p38-α kinase, or cardiac failure, for example, congestive heart failure, cardiomyopathy and myocarditis.

The manner of administration and formulation of the compounds useful in the invention and their related compounds will depend on the nature of the condition, the severity of the condition, the particular subject to be treated, and the judgement of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

It should be noted that the compounds of formula (1) can be administered as individual active ingredients, or as mixtures of several embodiments of this formula. In addition, the inhibitors of p38 kinase can be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As implied above, although the compounds of the invention may be used in humans, they are also available for veterinary use in treating animal subjects.

The following examples are intended to illustrate but not to limit the invention, and to illustrate the use of the above Reaction Schemes.

EXAMPLE 1

6-Methoxy-(4-benzylpiperidinyl)-indole-5-carboxamide-3-glyoxalic acid

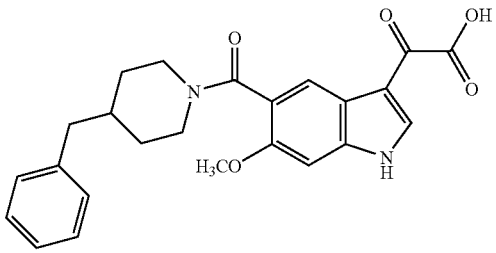

0.348 mg (1 mmol) of 6-methoxy-(4-benzylpiperidinyl)-indole-5-carboxamide was dissolved in 15 mL dry dichloromethane and was cooled to 0° C. in an ice bath. 0.6 mL of a 2 molar solution of oxalylchloride in dichloromethane (Aldrich) was added dropwise using a syringe under inert atmosphere and the mixture was stirred at 0° C. for an h. The ice bath was removed and the mixture stirred further an h. at room temperature. The solvent was evaporated and the residue dried under vacuum for 30 Min. The solid obtained was dissolved in a mixture of THF/water and basified with 20% aq. NaOH. The solvents were removed and the residue dissolved in water and acidified with conc. HCl. The precipitated solid was collected by filtration, dried and recrystallized from ethanol/water to yield 350 mg of the title compound.

ESMS. 421, M+

EXAMPLE 2

6-Methoxy-(4-benzylpiperidinyl)-5-carboxamido-indole-3-glyoxalicacid-4-methylpiperazinamide

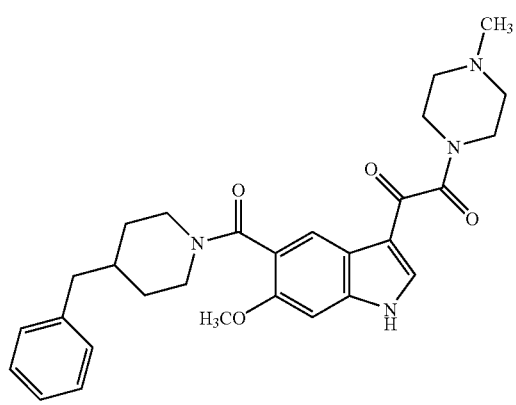

This compound was prepared using the same procedure used above for the corresponding acid, but substituting 4-methylpiperazine for aq. NaOH and carrying out the reaction in dry dichloromethane instead of THF/water.

ESMS. 503, M+

EXAMPLE 3

6-Methoxy-(4-benzylpiperidinyl)-5-carboxamido-indole-3-glyoxalicacid-1-(2-aminoethylpyrrolidine)-amide

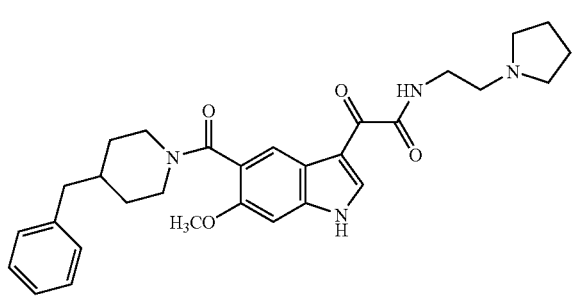

This compound was prepared using the same procedure used above, but substituting 1-(2-aminoethyl)-pyrrolidine for 4-methylpiperazine.

MS. M+, 517,

EXAMPLE 4

4-benzylpiperidinyl-5-carboxamido-indole-3-glyoxalicamide

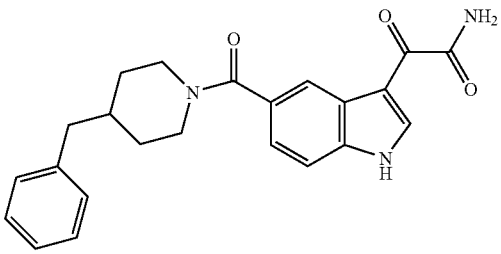

0.31 g, 1 mmol, of 4-benzylpiperidinyl-indole-5-carboxamide was dissolved in dry dichloromethane and was reacted with 0.6 mL 2 molar solution of oxalylchloride at 0° C. for 1 h under nitrogen. Cooling was removed and the mixture was stirred an additional 1 h. At RT. The solvent was evaporated and the residue dried under vacuum for 30 Minutes. The product was redissoved in THF and excess of con. Ammonium hydroxide was added. After stirring for 1 h. The solvent was removed and the residue recrystallized from ethylacetate-hexane.

Yield; 220 mg. MS. M+, 389; 345, M+–$CONH_2$

EXAMPLE 5

6-Chloro-(4'-fluoro-4-benzylpiperidinyl)-5-carboxamido-indole-3-glyoxalicacid, 4-methylpiperazinamide

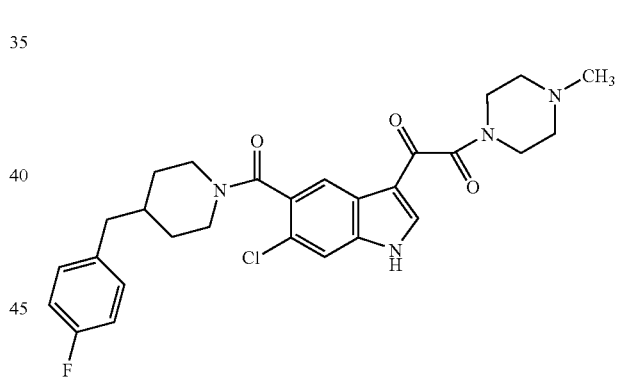

Prepared using similar procedure above described.
MS. M+, 524.

EXAMPLE 6

Preparation of 6-methoxy-(4-benzylpiperidinyl)-indole-5-carboxamide-3-glyoxalicacid methylester

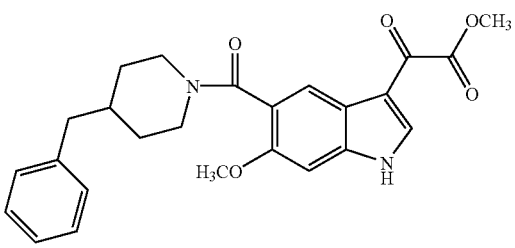

This compound was prepared using the same procedure described for the parent glyoxalic acid, but substituting methanol for sodium hydroxide in THF/water.
ESMS: M+ 435.

EXAMPLE 7

Preparation of 1-methyl-6-methoxy-[4'-fluoro-(4-benzylpiperidinyl)-]-indole-5-carboxamide-3-glyoxalic acid methylester

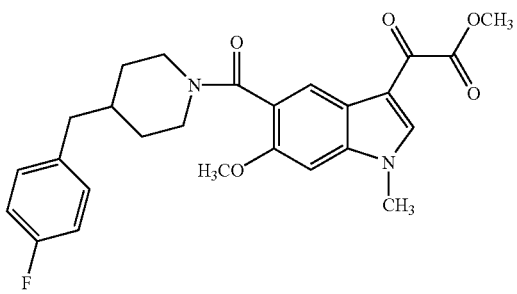

0.435 g of 6-methoxy-[4'-fluoro-(4-benzylpiperidinyl)-]-indole-5-carboxamide-3-glyoxalic acid methylester was dissolved in 10 mL dry DMF and was cooled to 0° C. in an ice-bath. 80 mg NaH (60% dispersion) was added and the mixture stirred for 15 minutes at 0° C. and 30 min. at room temperature under inert atmosphere. The reaction mixture was cooled to 0° C. and 200 μL of iodomethane was added. After 30 Min. at 0° C., it was allowed to warm to room temperature and stirring continued for another 4 h. The reaction mixture was poured in to water and extracted with dichloromethane (3×50 mL). The extract was dried, evaporated and purified by chromatography on silica gel with ethylacetate-hexane (50 to 90% ethylacetate, gradient).
Yield: 70%
MS: M+, 466.

EXAMPLE 8

Preparation of 1-methyl-6-methoxy-[4'fluoro-(4-benzylpiperidinyl)-]-indole-5-carboxamide-3-glyoxalic acid

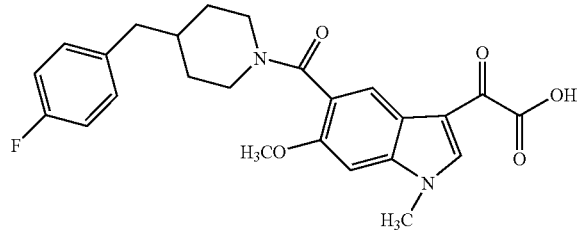

0.24 g (0.51 mmol) of 1-methyl-6-methoxy-[4'fluoro-(4'benzylpiperidinyl)-]-indole-5-carboxamide-3-glyoxalic acid methylester was dissolved in THF (10 mL) and 1 mL 20% aq. sodiumhydroxide was added and stirred for 4 h. It was diluted with water (5 mL) and stirring continued for 1 h. THF was removed under reduced pressure and the remaining solution was diluted with water and acidified with conc. HCl and the product was collected by filtration. It was dried in vacuo and recrystallized from ethylacetate.
Yield: 180 mg
ESMS: M+, 453.

EXAMPLE 9

3-(-Methoxybenzoyl)-(4-benzylpiperidinyl)-indole-5-carboxamide

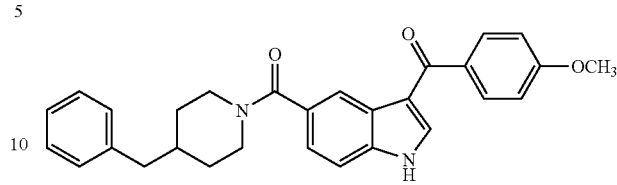

Acylation at 3-position of the indole ring system was achieved by a procedure of C. X. Yang, et al. (Synth. Commun. 27 (12), 2125 (1997). To a solution of 0.318 g (1.0 mmol) of 5(4-benzylpiperidinyl)-indole carboxamide in dichloromethane was added 2.2 mL (2.2 mmol) of 1 M solution of $ZnCl_2$ in ether followed by the dropwise addition of EtMgBr (1.0 mmol). The mixture was stirred for 1 h and p-anisoyl chloride (180 mg, 1,1 mmol) was added. The suspension was stirred for 1 h and $AlCl_3$ (0.05 mmol) was added. The resultant mixture was stirred for 2 h and was quenched with Sat. $NH_4Cl$ solution. The organic layer was washed with aq. $NaHCO_3$ and brine, dried over $MgSO_4$ and filtered. The solvent was evaporated and the product was purified by Silica gel chromatography.
MS. M+, 452.

EXAMPLE 10

3-Benzoyl-5-(4-benzylpiperidinyl)-indole carboxamide

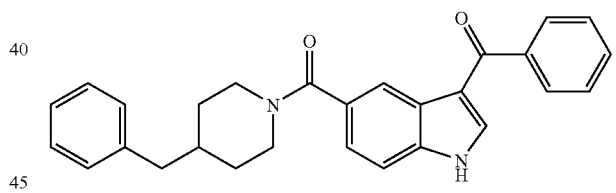

Prepared using the same procedure described above, but substituting benzoyl chloride for p-anisoyl chloride.
MS: M+, 422.

EXAMPLE 11

3-acetyl-5-(4-benzylpiperidinyl)-indole-5-carboxamide

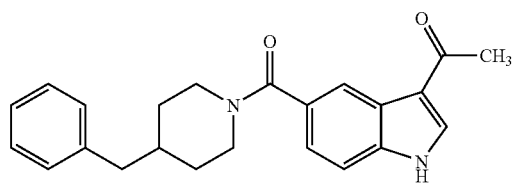

Prepared using the same procedure described above, but substituting acetyl chloride for p-anisoyl chloride.

MS: M+, 360.

EXAMPLE 12

Preparation of 3-(2-hydroxyacetyl)-5-(4-benzylpiperidinyl)-indole carboxamide

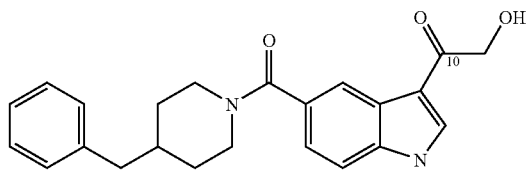

3-(2-chloroacetyl)-5-(4-benzylpiperidinyl)-indole carboxamide was prepared using the same procedure described before, but substituting chloroacetyl chloride for p-anisoyl chloride.

Hydrolysis of the chloroacetyl moiety to the hydroxyacetyl was achieved by using published procedure. (J. Org. Chem. 1988, 53, 5446). To a solution of 50 mg (0.13 mmol) of 3-(2-chloroacetyl)-5-(4-benzylpiperidine)-indole-carboxamide in dioxane (3 mL) was added 5 mL of formamide-water (10:1). The reaction mixture was heated at 110° C. for 5 h and cooled to RT. The reaction mixture was quenched with sat. $NH_4Cl$ solution, extracted with dichloromethane, dried (MgSO4) and concentrated. The residue was purified by preparative TLC developed with dichloromethane-methanol (20:1) to give 20 mg (42%) of the title compound.

MS. M+, 376.

EXAMPLE 13

5-(4-Benzylpiperidinyl)-carboxyamido-indole-3-(3'-oxo)-ethylpropionate

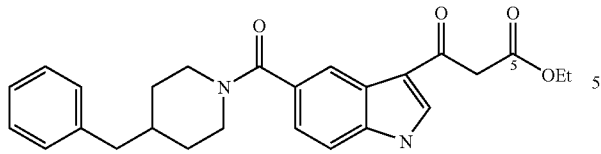

The acylation of 3-position was obtained by published method. [Synth. Commun. 1977, 27 (12), 2125]. To a solution of 3.6 mL of $ZnCl_2$ (3.6 mmol, 1M solution in diethyl ether) in THF (15 mL) was added n-BuLi (2.2 mL, 3.6 mmol) dropwise at 0° C. A white suspension was formed during the addition. The reaction mixture was warmed to RT, stirred for 1 h, and a solution of 5-(4-benzylpiperidinyl)-indolecarboxamide in dichloromethane (10 mL) was added. The resulting mixture was stirred for 1 h and ethyl 3-chloro-3-oxopropionate (585 mg, 3.9 mmol) was added. After 1 h, the reaction mixture was quenched with saturated $NH_4Cl$, extracted with dichloromethane, dried (MgSO$_4$) and concentrated. The residue was purified by silica gel chromatography to yield 200 mg of the desired product.

MS>M+, 431.

Compounds 1–55 of FIG. 2 were similarly prepared.

EXAMPLE 14

Synthesis of (2S,5R)N-4-Fluorobenzyl-trans-2,5-dimethylpiperazine (+/−)N-Benzyl-trans-2,5-dimethylpiperazine was synthesized as follows

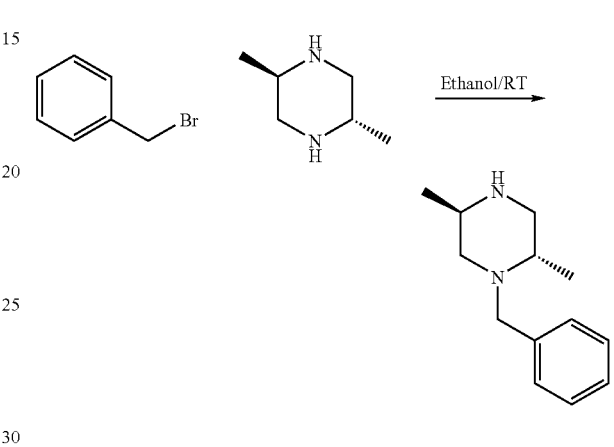

50 g trans-2,5 dimethylpiperazine was dissolved in 300 mL ethanol and treated with 26.36 mL (1/2 equivalents) benzylbromide. The mixture was stirred at room temperature for 12 hours and concentrated. The residue was taken up in ethyl acetate and washed with 10% aqueous sodium bicarbonate and saturated sodium chloride; dried over anhydrous magnesium sulfate and concentrated to give crude 1-benzyl-trans-2,5-dimethylpiperazine, as an oil.

This material was chromatographed using DCM/MeOH 95/5 to remove the di-alkylated product and then with DCM/MeOH/TEA 90/10/0.1 to elute the benzyl-trans-2,5-dimethylpiperazine. 19.6 g of the pure product was obtained as an oil.

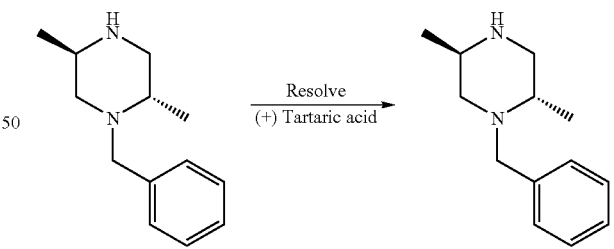

To a solution of (+/−)N-benzyl-trans-2,5-dimethylpiperazine (59 g, 0.29 mol) in Methanol (150 mL) was added a solution of (+) tartaric acid (87 g, 0.58 mol) in Methanol (250 mL) dropwise over 5 min. Crystallization is effected by keeping the resulting mixture at 0° C. for 48–72 hours. Scratching of the solution after 12–16 hours facilitates the crystallization process. The mixture was filtered and washed with cold Methanol and dried to give the ditartaric acid salt (73.9 g) as white crystals. A single recrystallization from Methanol, cooling to room temperature afforded the salt as white crystals. (58 g) $[\alpha]_D=+47$, (c=1.00, Methanol).

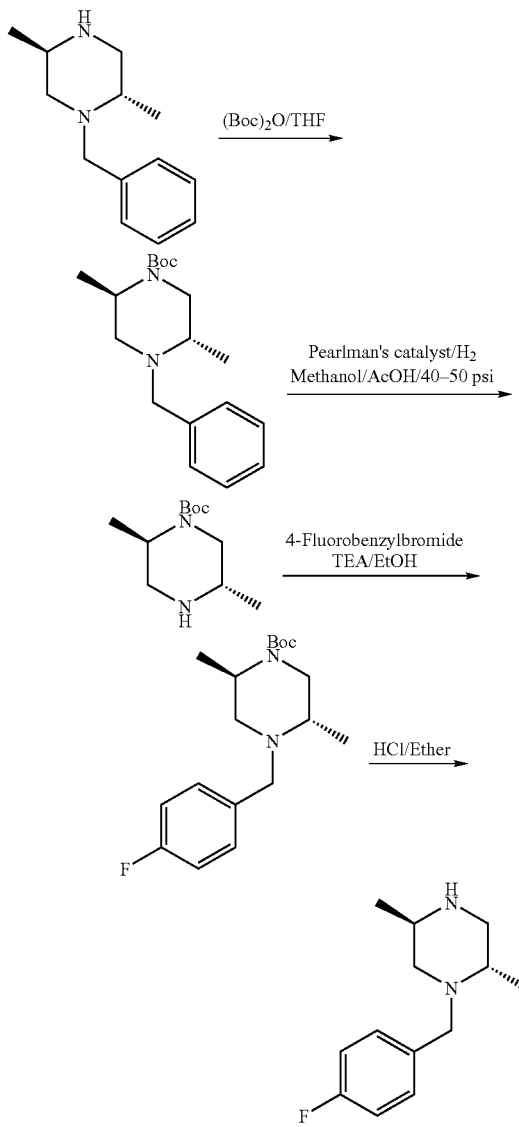

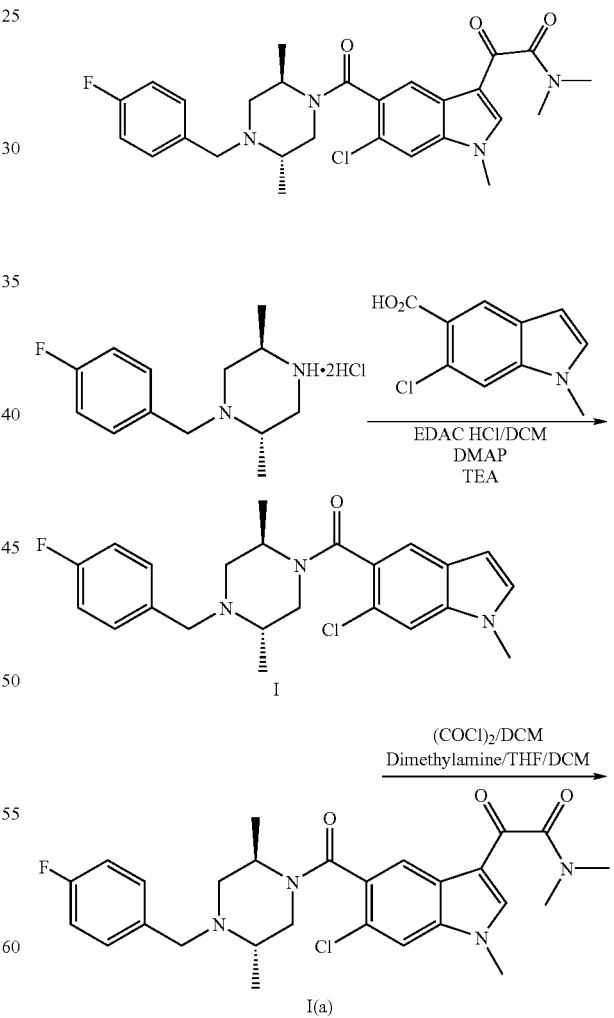

31 g, 15.27 mmol, dimethylbenzylpiperazine was treated with 43 g, 19.85 mmol of di-tert-butyl-dicarbonate in 250 mL THF for 4 hours. The reaction was monitored by TLC and is essentially complete when the addition of (BOC)₂O is complete. The solvent was removed and the residue was taken up in ethyl acetate and washed with 10% aqueous sodium carbonate and saturated sodium chloride, dried over anhydrous sodium sulfate and concentrated to give 39.3 g of the Boc-protected compound. This material was used for the next step without further purification.

39.3 g, 131 mmol, of the Boc-protected benzylpiperazine was treated with 3.93 g of Pearlman's catalyst, in 150 mL methanol with 3 mL acetic acid for 4 hours at 40 psi, hydrogen pressure in a parr shaker. The reaction mixture was filtered through celite and concentrated to give a residue that was dried under high vacuum and then dissolved in 250 mL dry ethanol and treated with 1.2 equivalents, 158 mmol of 4-Fluorobenzylbromide, and 2 equivalents, 262 mmol of triethylamine for 5 hours. The reaction mixture was monitored by TLC and found to be complete at that time. The solvent was removed and the residue was taken up in ethyl acetate and washed with 10% aqueous sodium carbonate and saturated sodium chloride, dried over anhydrous sodium sulfate and concentrated to give 47 g of crude product. This crude material was chromatographed on silica gel using Hexane/Ethyl acetate 95/5 to elute the product. After chromatography 29 g of the 4-Fluorobenzyl-trams-2,5-dimethylpiperazine was obtained.

20 g of the 1-(4-Fluoro)benzyl-trams-2,5-dimethylpiperazine, 62 mmol was treated with a mixture 200 mL 4 N HCl/Dioxane/2 M HCl/Ether (1:3) for 1 hour. Electron impact mass spectroscopy confirmed the formation of product and the disappearance of starting material at that time. The reaction mixture was concentrated to give a white solid. This material was repeatedly washed with hexane and ether to remove residual dioxane, and then dried under vacuum extensively before use. 17.6 g of the final product was obtained as a white fluffy solid.

EXAMPLE 15

Synthesis of Chiral Compounds

The 5-carboxylic-6-chloro indole acid (1.56 g, 7.44 mmol) was dissolved in dry methylene chloride 60 mL to this was added the EDAC.HCl (1.57 g, 8.18 mmol) and DMAP(10% mol). After stirring under nitrogen for 10 min. the amine (2.19 g, 7.5 mmol) was added, followed by triethylamine (3 mL, 21.52 mmol). After overnight at room temperature, the reaction mixture was concentrated and the residue was taken up in ethyl acetate and washed with 10% aq. sodium carbonate, saturated sodium chloride, dried over anhydrous sodium sulfate and filtered. Concentration gives the crude product that was chromatographed on silica gel using a gradient of EtOAc/Hexane 2/8–6/4. TLC $R_f$ 0.435 (EtOAc:Hexane, 1:1), EIMS M$^+$ 413.

1.02 g of the product from the above step was dissolved in 30 mL dry DCM. The reaction mixture was purged with nitrogen and placed in an ice bath. To this was added 4 mL of 2M oxalyl chloride in DCM. The reaction mixture was stirred at room temperature for 1 hour and then at room temperature for 2 hours. Reaction mixture was concentrated on a rotary evaporator. After drying on a vacuum pump for 15 min. the residue (a yellow solid) was dissolved in dry DCM, 30 mL, to which was added 4 mL of a 2M solution of dimethylamine in THF. 30 minutes later the reaction mixture was concentrated and the residue was taken up in ethyl acetate and washed with 10% aq. sodium carbonate, saturated sodium chloride, dried over anhydrous sodium sulfate and filtered. Concentration gives the crude product that was chromatographed on silica gel using a gradient of EtOAc 100%–EtOAc/MeOH 9:1. TLC $R_f$ 0.5 (EtOAc: MeOH, 9:1), EIMS M$^+$ 513.

The white solid from the above step was dissolved in 10 mL dry DCM. To this was added sufficient 2 M HCl in ether, till a precipitate persists. The mixture was then concentrated on a rotary evaporator to dryness and then dried overnight under high vacuum to give the final product (1.08 g).

ADDITIONAL EXAMPLES

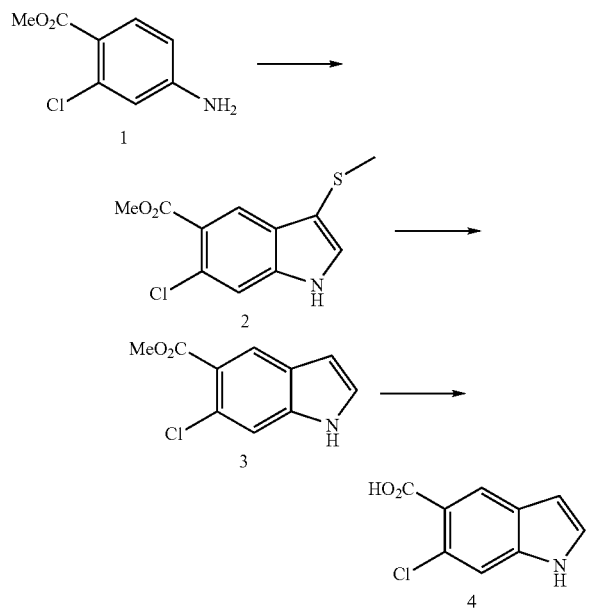

Synthesis of 2: Methyl 4-amino-2-chlorobenzoate (1) (18.5 g) was dissolved in dichloromethane (350 ml) and methyl thioacetaldehyde dimethylacetal (13.6 g) was added. The mixture was cooled to −45° C. (dry ice/acetonitrile bath). N-chlorosuccinimide (16.0 g) in 350 ml dichloromethane was added dropwise over 1 hr 30 min while maintaining bath temp at −45° C. The reaction mixture was stirred additional 1 hr, then triethylamine (16 mL, 100 mmols) in 30 ml dichloromethane was added dropwise over 5 min, reaction was warmed to room temp, then refluxed for 16 h. Solvent was removed and residue taken up in 500 ml carbon tetrachloride, triethylamine-hydrochloric acid was removed by filtration, filtrate was heated to reflux for 2 h. Solvent was removed by rotary evaporation.

The residue was dissolved in 250 ml tetrahydrofuran and 250 ml 10% hydrochloric acid was added. The mixture was stirred overnight at room temperature until the complete disappearance of the starting material was observed. Solvent was removed under vacuum, acidic aqueous solution was extracted with ethyl acetate (3×25 ml). The combined ethyl acetate extracts were washed with 10% hydrochloric acid, water and dried over anhydrous sodium sulfate. Solvent was removed under vacuum. Crude product mixture was purified on a silica column eluting with ethyl acetate:hexanes (15:85) to give 6.4 g of the desired product 2.

Synthesis of 3: Methyl 6-Chloro-3-thiomethyl-5-indole carboxylate (5.2 g) was dissolved in 150 ml ethanol:tetrahydrofuran (9:3) and treated with Raney-Nickel. Reaction was monitored by mass spec at 30 min intervals, with subsequent addition of Raney-Nickel until reaction was complete. When reaction was complete reaction was carefully filtered through celite and the celite washed with methanol several times and filtrate evaporated. Residue was taken up in ethyl acetate, washed with water, dried over anhydrous sodium sulfate. The solvent was removed to give 3 (3.2 g).

Synthesis of 4: Methyl ester 1.5 g was dissolved in 30 ml methanol/water 50:50. The reaction mixture was heated at 50° C. for 2 h with 4 Mol. equivalent sodium hydroxide. The reaction mixture was cooled in ice-bath, acidified to pH 3 with 5M hydrochloric acid. Removed methanol by rotary evaporation and extracted with ethyl acetate. The extract was washed with saturated sodium chloride and dried over anhydrous sodium sulfate. Evaporation of the solvent gave the desired acid 4 (1.48 g).

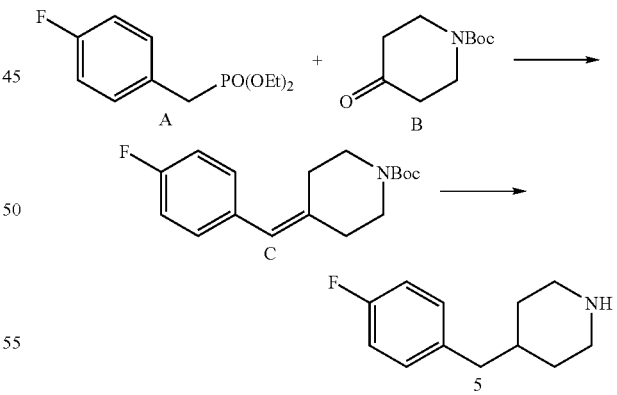

Synthesis of 5:

STEP A: The phosphonate A (38.4 g) and the piperidone B (35.4) were dissolved in anhydrous dimethylformamide (400 mL). To this sodium hydride (60% suspension in oil) was added in portions while the reaction is maintained at 0° C. After the addition of sodium hyride was complete the reaction mixture was stirred for 30 min. and then the ice bath was removed, the reaction was allowed to stir for 6 h as it slowly warmed to ambient temperature. The reaction was again cooled in an ice bath and quenched with methanol. Water was added to the reaction mixture, and the product extracted with ethyl acetate. The ethyl acetate layer was washed with saturated sodium chloride and dried over anhydrous magnesium sulfate. The solvent was removed to gives the crude alkene, which is purified by column chromatography eluting with ethyl acetate/hexane (1:9) to give 21.8 g of the desired product C.

STEP B: 10.1 g of C was dissolved in 50 mL methanol. After purging the solution with nitrogen, 5% Palladium on carbon (1 g) catalyst was added followed by 1 mL acetic acid. The parr container containing the reaction mixture was hydrogenated for 4 h at 40–50 psi. The reaction mixture was filtered through celite and concentrated. The residue was treated with 2 M hydrochloric acid in ether to convert to the hydrochloric acid salt. The white solid that was obtained was dried under vacuum, extensively, to give 7.8 g of 5 as the hydrochloric acid salt.

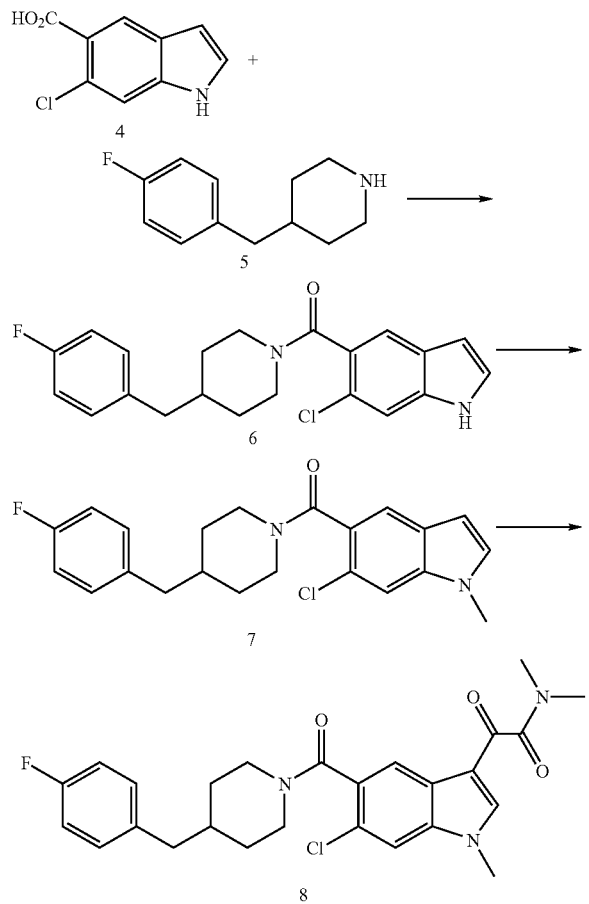

Synthesis of 6: A mixture of 6-chloro-indole-5-carboxylic acid (1.95 g), 4-fluoro-benzylpiperidine hydrochloric acid salt (2.76 g) was taken in 50 mL dry dichloromethane and was treated with triethylamine (1.7 mL). The mixture was stirred until a clear solution was obtained. 1-ethyl-3-(3-dimethylaminopropyl)carbodiimide (2.3 g) and dimethylaminopyridine (0.25 g) was added and the mixture was stirred for 20 h at ambient temperature. The mixture was poured in to water and the organic layer separated. The aq. Solution was further extracted twice with dichloromethane. The combined extract was washed with 10% hydrochloric acid. The organic layer was dried over magnesium sulfate and evaporated. The product was purified by chromatography on silica gel eluting with ethylacetate:hexane (3:7) to give 6 (2.78 g).

Synthesis of 7: 8.61 g of 6-chloro-(4-F-benzylpiperidinyl)-indole-5-carboxamide (6) was dissolved in about 100 mL dry DMF and the solution was cooled in an ice-bath. To the cold solution was added 30 mL of 1M solution of sodium bis-(trimethylsilyl)-amide in tetrahydrofuran under inert atmosphere. The reaction was allowed to stir at 0° C. for 15 min and at ambient temperature for another 30 min. The reaction mixture was cooled again in ice-bath and 2.5 mL of iodomethane was added. After stirring for 30 min. at 0° C., it was allowed to warm to AMBIENT TEMPERATURE and stirring continued for 18 h at AMBIENT TEMPERATURE. The mixture was diluted with water (or brine) and the product was extracted with ethylacetate (4×75 mL). The combined extract was washed with water and dried over anh. MgSO$_4$. The solvent was removed and the product was purified by column chromatography on silica gel eluting with ethylacetate:hexane (1:4) to yield 8.0 g of the desired product 7.

Synthesis of 8: 8 g of 7 was dissolved in about 100 mL of anhydrous dichloromethane and was cooled in an ice-bath. To this a 2M solution of oxalylchloride (20.8 mL) in dichloromethane was added slowly via a syringe and the mixture was allowed to stir at 0° C. for 1 h. The ice-bath was removed and stirring continued for an additional 2 h at AMBIENT TEMPERATURE. The solvent was removed under reduced pressure and the residue was pumped for 15 min. to remove any excess oxalylchloride present. The product was immediately redissolved in anh. dichloromethane (150 mL), cooled in an ice-bath, 30 mL of a 2M solution of dimethylamine in tetrahydrofuran was added rapidly via a syringe. After 15 min. stirring it was allowed to stir for another 15 min. at ambient temperature. The solution was washed with water to remove the salt, and dried. After evaporation, the residue was purified on silica gel, eluting with chloroform:methanol (99:1) to yield 9.3 g of 8.

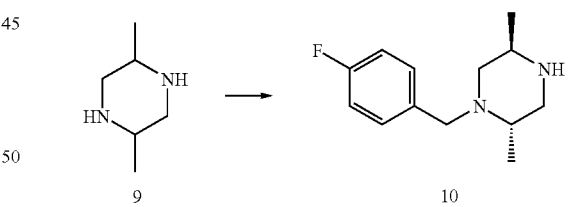

Synthesis of 10:

Synthesis of 10:

STEP A: To a solution of dimethyl piperazine 9 (25 g) in 300 ml of absolute ethanol was added 400 ml of 2N hydrogen chloride in diethyl ether. The solution was warmed to 70° C. in an oil bath for 20 minutes. The solution was then cooled to room temperature and set at 6° C. overnight. The solid obtained, was collected by filtration. Yield 39.8 g (dihydrochloride salt of trans-2,5 dimethylpiperazine) after drying overnight under high vacuum.

STEP B: An ethanol solution of 42.9 g of dimethyl piperazine dihydrochloride the from STEP A and 26.1 g trans-2,5 dimethylpiperazine was vigorously stirred in an oil bath at 80° C. until all starting materials were dissolved. The temperature of oil bath was reduced to 65° C. and 33.1 g of 4-fluro benzylchloride was added. After stirring at this temperature for 30 min., the solution was placed in a 6° C. refrigerator overnight. The solid was removed from the solution by filtration and excess of 2N hydrogen chloride in diethyl ether was added to the filtrate. The filtrate was kept at 6° C. overnight and the solid collected. The solid was suspended in 5% sodium hydroxide aqueous solution and extracted three times with ethyl acetate. The organic layer was dried over sodium sulfate and dried down to give a yellow oil.

STEP C: A solution of 50.7 g (L)-tartaric acid in 130 ml of boiling methanol was added to 70 ml of hot methanol solution of 37.5 g of the product from STEP B. The solution was set at 6° C. for 96 hours before collection of white fine crystals by filtration. This material was recrystallized from boiling methanol. The product was collected by filtration after being kept at a 6° C. overnight. Yield 30.5 g of ditartaric acid salt ([α]=+43.2°, c=1).

obtained, 0.7 g. Column chromatography on silica with ethyl acetate:hexane (2:8) gave methyl ester of 11 as a white solid. 0.52 g. 0.52 g of this product was dissolved in 50 mL methanol and treated with 5 mL 10 N sodium hydroxide, the reaction mixture was heated at 50° C. for 2 h. The reaction mixture was cooled to room temperature and concentrated to a solid on a rotary evaporator. The residue was taken in 50 mL water, washed with ether and placed in an ice bath. The basic solution was acidified with 10% hydrochloric acid to pH 2. The precipitate was extracted with ethyl acetate and the ethyl acetate layer was washed with saturated sodium chloride solution. Drying over anhydrous sodium sulfate, filtration and concentration on a rotary evaporator to gave 11 (0.48 g) as a white solid.

Synthesis of 12: 1.56 g of the acid (11) was dissolved in dry methylene chloride 10 mL and to this was added the 1-ethyl-3-(3-dimethylaminopropyl)carbodiimide (1.57 g) and dimethylaminopyridine (catalytic). After stirring under nitrogen for 10 min., 2.19 g of the amine (10) was added, followed by triethylamine (3 mL). After stirring overnight at room temperature, the reaction mixture was concentrated and the residue was taken up in ethyl acetate and washed with 10% aq. sodium carbonate, aq. saturated sodium chloride, dried over anhydrous sodium sulfate and filtered. Concentration gave the crude product which was chromatographed on silica gel using ethyl acetate:hexane (4:6) as eluent to give 1.02 g of the desired product.

Synthesis of 13: 1.02 g of 12 from the previous step was dissolved in 30 mL dry dichloromethane. The reaction mixture was purged with nitrogen and placed in an ice bath. To this was added 4 mL of 2M oxalyl chloride in dichloromethane. The reaction mixture was stirred at 0° C. for 1 hour and then at room temperature for 2 h. Reaction mixture was concentrated on a rotary evaporator. After drying on a vacuum pump for 15 min. the residue (a yellow solid) was dissolved in dry dichloromethane (30 mL) to which was added 4 mL of a 2M solution of dimethylamine in tetrahydrofuran. 30 minutes later the reaction mixture was concentrated and the residue was taken up in ethyl acetate and washed with 10% aq. sodium carbonate, saturated sodium chloride, dried over anhydrous sodium sulfate and filtered. Concentration gives the crude product that was chromatographed on silica gel with ethyl acetate:methanol (9:1). The white solid obtained was dissolved in 10 mL dry dichloromethane. To this was added sufficient 2 M hydrochloric acid in ether, till a precipitate persisted. The mixture was then concentrated on a rotary evaporator to dryness and then further dried overnight under high vacuum to give 13 (1.08 g).

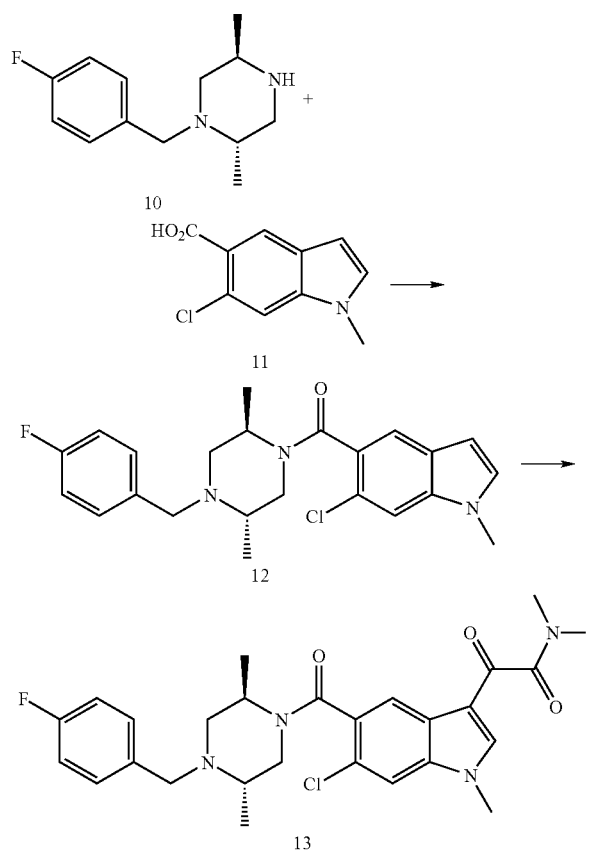

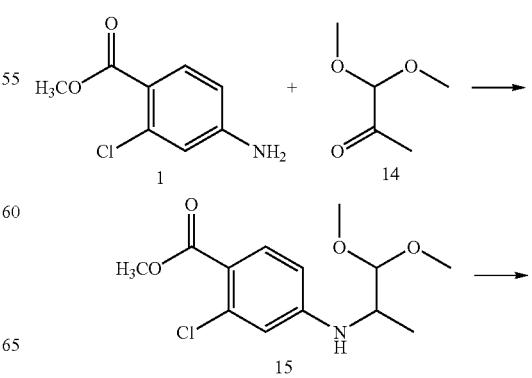

Synthesis of 11: The indole ester 3 (0.526 g) was dissolved in 10 mL acetone (dry) and placed in an ice bath. To this was added crushed potassium hydroxide (0.7 g, 12.5 mmol), after stirring for five minutes at 0° C., methyl iodide (400 μL, 6.272 mmol) was added to the reaction mixture. The reaction mixture was stirred at 0° C. for 10 minutes and then at room temperature for 30 minutes. After removal of the solvent, the residue was taken up in ethyl acetate and washed with saturated sodium chloride. After drying over anhydrous sodium sulfate, filtration and rotary evaporation, a solid was

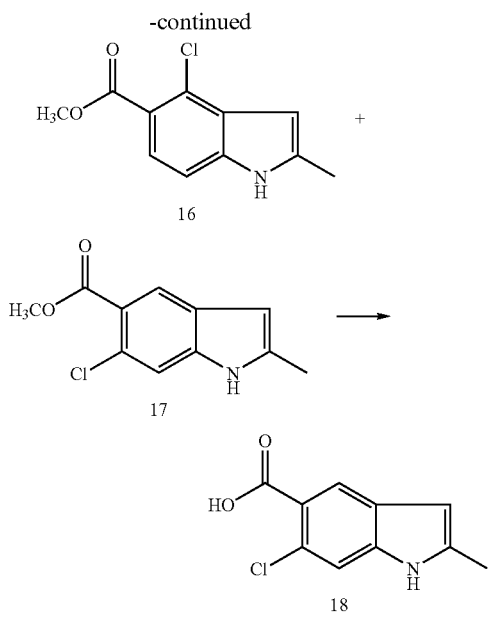

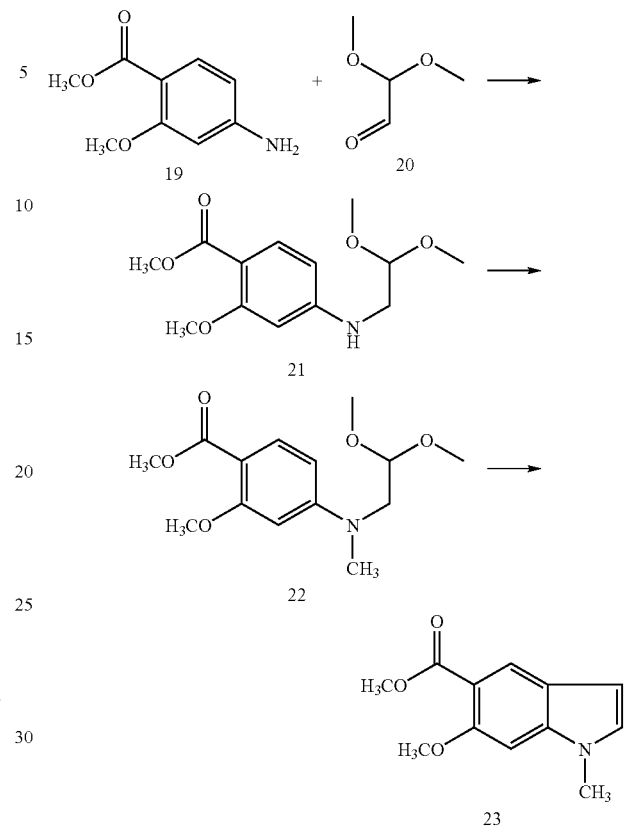

Synthesis of 15: To a solution of aniline 1 (9.25 g, 0.05 mol) and pyruvic aldehyde dimethyl acetal 14 (11.8 g, 0.1 mol) in 200 mL glacial acetic acid was added anhydrous sodium sulfate (71.0 g, 0.5 mol) and the mixture was stirred for 30 min. Powdered sodium triacetoxy borohydride (31.8 g, 0.15 mol) was then added in portions for a period of 5 min. The reaction mixture was stirred for an additional 2 h. Acetic acid was removed under reduced pressure and the residue was made basic by adding sufficient amount of saturated sodium bicarbonate solution. The product was then extracted with ethyl acetate, dried with sodium sulfate and evaporated to get an oil. This was chromatographed on silica gel column using ethyl acetate:hexane (3:7) to give 15 (14 g) as colorless oil.

Synthesis of 16 and 17: To a suspension of fresh aluminum chloride (18.5 g) in 200 ml dry chloroform at 0° C. was added a solution of ketal 15 (13.3 g) in 100 ml chloroform slowly and the mixture was allowed to warm up to the room temperature and stirred overnight. Ice-cold water was added carefully to quench the aluminum chloride and the organic layer was separated and washed with sodium bicarbonate solution, dried and evaporated to get a white solid. The isomers were separated using silica gel column chromatography using ethyl acetate:hexane (1:9). The 6-cholo indole 17 (2.0 g) eluted first followed by 4-chloro isomer 16 (3.8 g).

Synthesis of 18. To a solution of 1.3 g of indole 17 in 15 mL of methanol was added a solution of 0.9 g of sodium hydroxide in 20 mL of water. The reaction mixture was heated at 50° C. for 4 h where upon a clear solution resulted. Cooled and evaporated off methanol and the residue was diluted with water and acidified with 10% hydrochloric acid. The product was extracted with ethyl acetate. The organic layer was dried over sodium sulfate, filtered and evaporated to obtain indole acid 18 (1.2 g) as white solid.

2-Methyl-6-methoxyindole-5-carboxylic acid was also synthesized using the above synthetic procedure.

Synthesis of 21: To a solution of methyl 4-amino-6-methoxy 5-benzoate (19) (6.0 g, 0.033 mol) and dimethyl acetal 20 (7.0 g, 0.066 mol) in 150 mL glacial acetic acid was added anhydrous sodium sulfate (47.0 g, 0.33 mol) and the mixture was stirred for 30 min. Powdered sodium triacetoxy borohydride (20.1 g, 0.099 mol) was then added in portions for a period of 5 min. The reaction mixture was stirred for an additional 2 h. Acetic acid was removed under reduced pressure and the residue was made basic by adding sufficient amount of saturated sodium bicarbonate solution. The product was then extracted with ethyl acetate, washed with saturated sodium chloride, dried over sodium sulfate and evaporated to get an oil. This was chromatographed on silica gel column using ethyl acetate:hexane (3:7) as eluent and the desired product 21 was obtained (5.2 g) as an oil.

Synthesis of 22: To a solution of 21 (3.6 g) and iodomethane (5.7 g) in 50 mL anhydrous dimethylforamide was added potassium t-butoxide (1.0 M in tetrahydrofuran, 20 mL) at ambient temperature. The reaction mixture was stirred at ambient temperature for 0.5 h and poured into 250 mL ethyl acetate, washed with water (4×100 mL), brine (50 mL) and dried over magnesium sulfate. Evaporation of solvent afforded 3.26 g of 22. The product was used for next step without purification.

Synthesis of 23: To a suspension of anhydrous aluminum chloride (0.71 g) in 20 mL anhydrous 1,2-dichloroethane was added, dropwise a solution of 22 (1 g) in 10 mL 1,2-dichloroethane with stirring. The reaction was heated to 80° C. for 0.5 h. At the end of this time, the reaction mixture was quenched with methanol, solvents evaporated, then ethyl acetate (100 mL) was added. The organic phase was washed with water, aq. sodium bicarbonate and brine and concentrated. The crude product was purified by silica chromatography using ethyl acetate:hexane (3:7) to give 23 0.22 g.

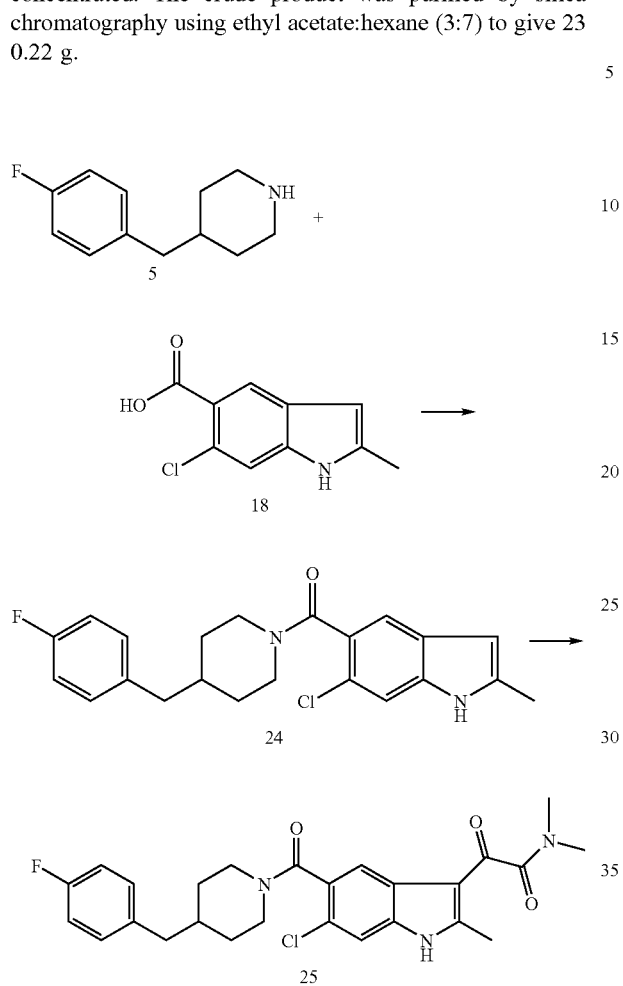

Synthesis of 24. To a suspension of 1.2 g of indole acid 18 and 1.6 g of 5 in 30 mL dichloromethane was added 0.7 g of triethylamine followed by 1.4 g of 1-ethyl-3-(3-dimethylaminopropyl)carbodiimide. The clear solution obtained was stirred for 4 h. The solvent was evaporated and the residue was taken up in ethyl acetate and washed with water, dil. hydrochloric acid, and brine. The organic layer was then dried with sodium sulfate and evaporated. The product was isolated (1.3 g) as white solids after silica gel chromatography using ethyl acetate:hexane (1:4).

Synthesis of 25: A solution of 1.3 g of 24 in 20 mL dichloromethane was cooled to 0° C. and a solution of 2 M oxalyl chloride in dichloromethane (3.4 ml, 6.8 mmol) was added and the reaction mixture was stirred at 0° C. for 1 h. The temperature was allowed to come to room temperature and continued stirring for an additional 1 h. The solvent was evaporated and the residue was dried under vacuum. The acid chloride was dissolved in dichloromethane (25 mL) and a solution of 6.8 mL (13.6 mmol) of 2 M N,N-dimethylamine in tetrahydrofuran was added all at once. The solvent was removed and the product was purified by silica gel column chromatography using methanol:chloroform (2:98). The product was obtained as white solid (1.4 g).

Synthesis of 27: A solution of 26 (130 mg) in anhydrous dimethylfor (5 ml) was stirred at 0° C. under nitrogen. Sodium hydride (25 mg, 60% dispersion in oil) was added and stirred for 5 min., then room temp for 30 min. The mixture was cooled at 0° C. and chloromethyl methyl sulfide (70 μl) was added. The reaction mixture was stirred for 20 h at room temp, and then was extracted with ethyl acetate. The organic layer was dried over sodium sulfate, concentrated under vacuum. The residue was purified by chromatotron using methanol:chloroform (2:98) to give 100 mg of 27.

Synthesis of 28: A solution of oxone (120 mg) in water (1 ml) was added to the suspension of 27 (100 mg) in glacial acetic acid (4 ml). The reaction mixture was stirred at room temp. for 18 h, washed with water, and concentrated under vacuum. The residue was purified by chromatotron using methanol:chloroform (2:98) to give 60 mg of 28.

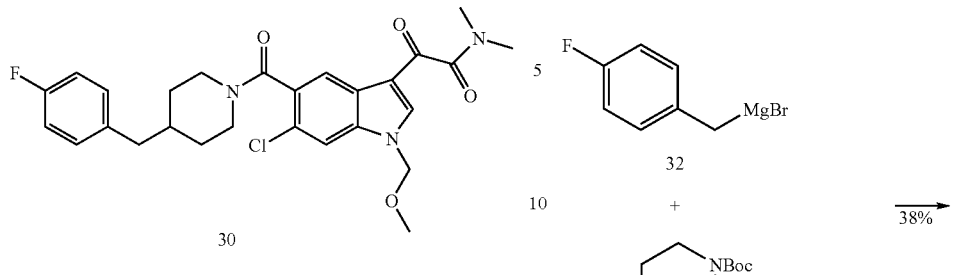

Synthesis of 30: To a solution of 29 (200 mg) in tetrahydrofuran (20 mL) was added sodium bis(trimethylsilyl) amide (0.51 mL, 0.51 mmol) dropwise at 0° C. The mixture became light yellow solution, warmed to ambient temperature slowly and was stirred for 30 min. Then methoxy methyl chloride was added and the reaction mixture was stirred overnight. The reaction mixture was quenched with ammonium chloride and extracted with dichloromethane. The combined organic layer was washed with brine, dried and concentrated. The residue was purified by chromatography on silica gel and eluted with methanol:dichloromethane (5:95) to give 190 mg of 30.

Synthesis of 31: To a solution of 29 (200 mg) in tetrahydrofuran (10 mL) was added sodium bis(trimethylsilyl) amide (0.56 mL, 0.56 mmol) dropwise at 0° C. The reaction mixture was warmed to ambient temperature slowly, stirred for 30 min, and then added to the solution of tosyl cyanide (115 mg) in tetrahydrofuran (10 mL). The resulting mixture was stirred for 2 h at rt, quenched with ammonium chloride and extracted with dichloromethane. The combined organic layer was washed with brine, dried and concentrated. The residue was purified by chromatography on silica gel and eluted with methanol:dichloromethane (5:95) to give 90 mg of 31.

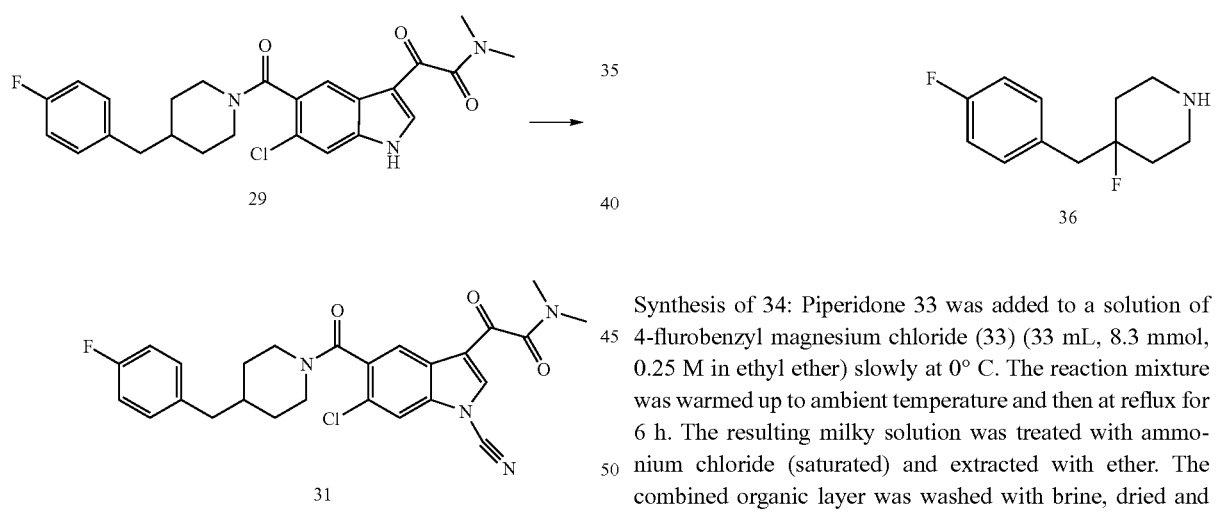

Synthesis of 34: Piperidone 33 was added to a solution of 4-flurobenzyl magnesium chloride (33) (33 mL, 8.3 mmol, 0.25 M in ethyl ether) slowly at 0° C. The reaction mixture was warmed up to ambient temperature and then at reflux for 6 h. The resulting milky solution was treated with ammonium chloride (saturated) and extracted with ether. The combined organic layer was washed with brine, dried and concentrated. The residue was purified by chromatography on silica gel eluting with hexane:ethyl acetate (4:1) to give 990 mg of 34.

Synthesis of 35: The alcohol 34 (670 mg) in dichloromethane (10 mL) was added to the solution of diethylaminosulfur trifluride (0.57 mL, 4.34 mmol) in dichloromethane (20 mL) at −78° C. The reaction mixture was warmed up to ambient temperature slowly and stirred for 2 h, and then treated with sodium carbonate (saturated) and extracted with dichloromethane. The combined organic layer was washed with brine, dried and concentrated. The residue was purified by chromatography on silica gel eluting with hexane:ethyl acetate (8:1) to give 300 mg of 35.

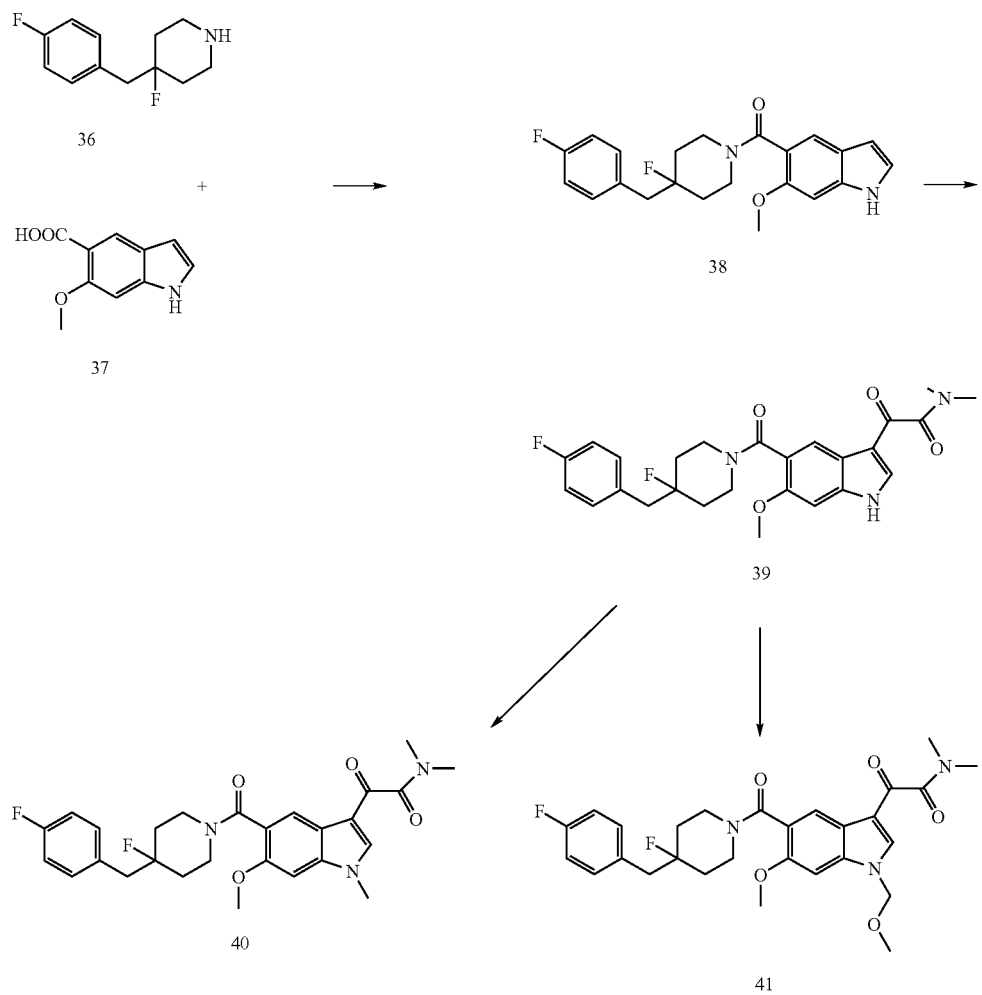

Synthesis of 36: A mixture of the 35 (456 mg) and 4 M of hydrochloric acid in dioxane (10 mL) was stirred for 4 h. The reaction mixture was neutralized with sodium carbonate, extracted with ethyl acetate. The combined organic layer was washed with brine, dried and concentrated. The crude product was used in the next reaction without further purification.

Synthesis of 38: To the suspension of indole carboxlic acid 37 (475 mg) in anhydrous dichloromethane (20 mL) was added piperidine 36 (350 mg, 1.66 mmol). The mixture was stirred for 10 min and then 1-[3-(dimethylaminopropyl]3-ethylcarbodiimide hydrochloride (475 mg) and dimethylaminopyridine (202 mg) were added. The reaction mixture became clear and was continually stirred for overnight. Then the reaction mixture was treated with 10% of hydrochloric acid solution, and extracted with dichloromethane. The combined organic extracts were washed with sodium bicarbonate, brine, dried and concentrated. The residue was purified by chromatography on silica gel eluting with dichloromethane:ethyl acetate (9:1) to give 300 mg of 38 as a white foam.

Synthesis of 39: To the suspension of 38 (200 mg) was added oxaly chloride (0.52 mL, 1.04 mmol, 2 M in dichloromethane) dropwise at 0° C. The reaction mixture was stirred at 0° C. for 30 min, and then warmed up to rt. and stirred for 5 h. The yellow suspension was formed. The solvent and excess oxaly chloride were removed under the reduced pressure. The yellow solid formed was dried under vacuum, and dissolved in dichloromethane then cooled in ice bath. Dimethyl amine (1.04 mL, 2.08 mmol, 2 M in tetrahydrofuran) was added. After 30 min, the reaction mixture was treated with water and extracted with dichloromethane. The organic extracts were washed with water, brine, dried and concentrated. The residue was purified by chromatography on silica gel eluting with 3% of MeOH in dichloromethane to give 190 mg of 39 as a white solid.

Synthesis of 40: To a solution of 39 (75 mg) in tetrahydrofuran (10 mL) was added KHMDS (0.46 mL, 0.23 mmol, 0.5 M in toluene) dropwise at 0° C. The mixture was warmed to rt. slowly and stirred for 30 min. Then methyl iodide (33 mg, 0.23 mmol) was added slowly to the reaction mixture, then stirred for 2 h. The reaction mixture was quenched with ammonium chloride and extracted with dichloromethane. The combined organic extracts were washed with brine, dried and concentrated. The residue was purified by chromatography on silica gel eluting with methanol:dichloromethane (2:98) to give 50 mg of 40.

Synthesis of 41: To a solution of 40 (75 mg) in tetrahydrofuran (10 mL) was added KHMDS (0.46 mL, 0.23 mmol, 0.5 M in toluene) dropwise at 0° C. The mixture was warmed to rt. slowly and stirred for 30 min. Then methoxy methyl chloride (18 mg, 0.23 mmol) was added slowly to the reaction mixture, then stirred overnight. The reaction mixture was quenched with ammonium chloride and extracted with dichloromethane. The combined organic extracts were washed with brine, dried and concentrated. The residue was purified by chromatography on silica gel eluting with methanol:dichloromethane (2:98) to give 65 mg of 41.

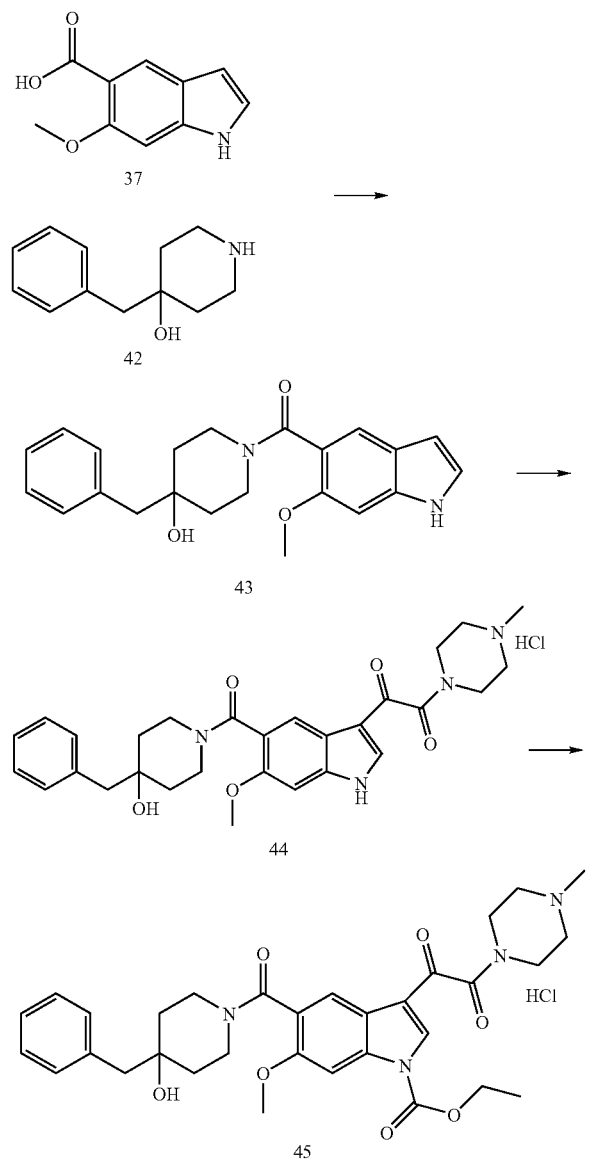

Synthesis of 43: To a suspension of 6-methoxy-5-indolecarboxylic acid (37) (200 mg) in dichloromethane (5 mL) was added 1-[3-(dimethylaminopropyl]3-ethylcarbodiimide hydrochloride (258 mg, 1.35 mmol) in one portion. The reaction mixture was stirred till all of the solid was dissolved. 4-Benzyl-4-hydroxypiperidine (42) (258 mg), obtained by removal of the protecting group from 34 as outlined in the synthesis of 36, was added and stirred at ambient temperature. The reaction mixture became cloudy. A catalytic amount of dimethylaminopyridine (10 mg) was added and stirred at ambient temperature overnight. The reaction mixture was treated with water, and extracted with dichloromethane. The combined organic layer was washed with 10% of hydrochloric acid solution, sodium bicarbonate (saturated) and brine, then dried and concentrated to give 300 mg (82%) of 43 as a yellow foam.

Synthesis of 44: Oxalyl chloride (0.41 mL, 1.65 mmol, 2 M in dichloromethane) was added to a solution of 6-methoxy-(4-benzyl-4-hydroxypiperidinyl)-indole-5-carboxamide (300 mg) in dichloromethane (20 mL) at 0° C. dropwise. The reaction mixture was stirred at 0° C. for 30 min, and then warmed up to ambient temperature slowly. After 2 h., a yellow precipitation was formed. The reaction mixture was concentrated under the reduced pressure and dried for 1 h under reduced pressure. The resulting yellow solid was suspended in dichloromethane (20 mL). Methyl piperazine (0.2 mL) and diisopropyl ethyl amine (0.2 mL) were added at rt. The mixture was stirred for 1 h, treated with water, and extracted with dichloromethane. The residue was purified by chromatography on silica gel eluting with dichloromethane:methanol (10:1) to give 180 mg of a white solid. 20 mg of this white solid was dissolved in methanol (1 mL). To this a saturated hydrochloric acid solution in methanol was added dropwise till the pH value was around 3. Then the solvents were removed and the product was dried to give 44.

Synthesis of 45: To a solution of 44 (65 mg) in anhydrous tetrahydrofuran (10 mL) was added sodium bis(trimethylsilyl)amide (0.25 mL, 0.25 mmol, 1.0 M solution in tetrahydrofuran) dropwise at ambient temperature. The mixture was stirred at ambient temperature for 30 min, and then ethyl chloroformate (0.024 mL, 0.25 mmol) was added to the reaction mixture. After 1 h, the reaction mixture was quenched with ammonium chloride (saturated), and extracted with ethyl acetate. The combined organic layer was washed with brine, dried (magnesium sulfate) and concentrated under reduced pressure. The residue was purified by chromatography on silica gel, eluting with dichloromethane:methanol (10:1) to give 15 mg of the title compound 45 as a white solid. This was dissolved in methanol (1 mL) and to this was added saturated hydrochloric acid solution in methanol dropwise till the pH value is around 3. Then the solvent was removed and the product was dried to give the hydrochloric acid salt of 45.

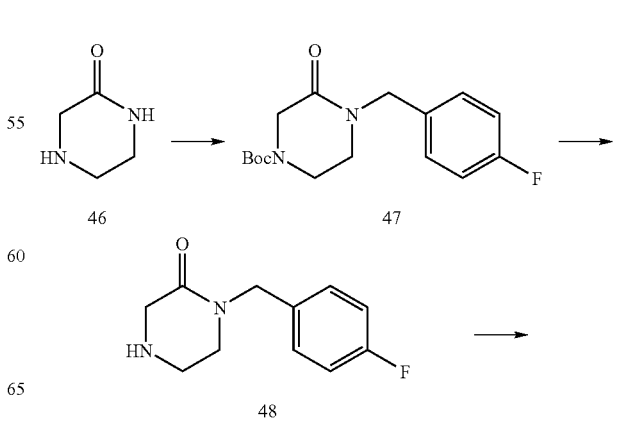

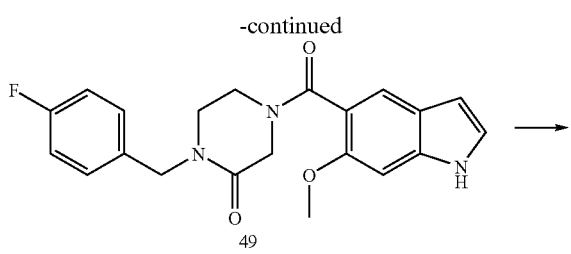

49

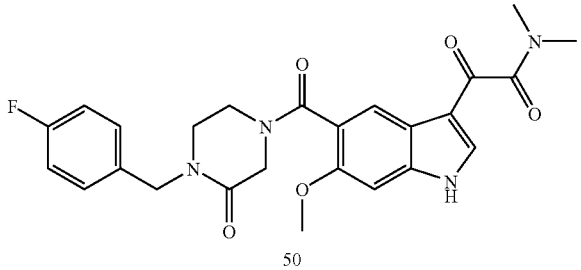

50

Synthesis of 47:

STEP A: Piperizinone 46 (5.0 g) was dissolved in 15 mL tetrahydrofuran, to this was added a solution of di-tertbutyl-dicarbonate (12.04 g in 50 mL tetrahydrofuran). After stirring at room temperature for 4 h. The reaction mixture was concentrated to dryness on a rotary evaporator and the solid obtained used for the next reaction without further purification.

STEP B: 10 g of product from STEP A was dissolved in anhydrous acetone and the reaction mixture was cooled in an ice bath. To this was added crushed potassium hydroxide (14.02 g). After stirring at 0° C. for 10 min. 4-fluoroben-zylbromide (23.5 g) was added and the reaction mixture stirred at 0° C. for 20 min and at room temperature for 1 h. After removal of the solvent on a rotary evaporator the residue was taken up in ethyl acetate and washed with 10% aqueous sodium carbonate, brine and dried over anhydrous sodium sulfate. Filtration and concentration gave crude material that was purified by chromatography on silica gel using ethyl acetate/hexanes gave 14 g of 47.

Synthesis of 48: 14 g of 47 was dissolved in 100 mL methylene chloride and treated with 100 mL 2 M Hydrochloric acid in ether for 2 h. The solvent was removed and the solid obtained was washed with ether and hexanes and dried under high vacuum to give 48 (11.3 g) as the hydrochloride salt.

Synthesis of 49: 1 g of 48, was dissolved in 20 mL methylene chloride and treated with 6-methoxy-5-indole carboxylic acid (37) (0.87 g), 1-ethyl-3-(3-dimethylamino-propyl)carbodiimide (0.95 g), triethylamine (700 μL) and dimethyaminopyridine (catalytic) and the reaction mixture stirred overnight. The reaction mixture was concentrated and the residue taken up in ethyl acetate, washed with 10% aqueous sodium carbonate, brine and dried over anhydrous sodium sulfate. Filtration and concentration gave crude material that was purified by chromatography on silica gel using ethyl acetate/hexanes to give 49 (1.6 g).

Synthesis of 50: 1.6 g of 49 was dissolved in 25 mL dry dichloromethane. The reaction mixture was purged with nitrogen and placed in an ice bath. To this was added, 5 mL 2M oxalyl chloride in dichloromethane. The reaction mixture was stirred at room temperature for 1 h and then at room temperature for 2 h. Reaction mixture was concentrated on a rotary evaporator and after drying on a vacuum pump for 15 min. the residue (a yellow solid) was dissolved in dry dichloromethane. To this residue a 2M solution of dimethylamine in THF (5 mL) was added and the reaction mixture stirred for 0.5 h. The reaction mixture was then concentrated and the residue was taken up in ethyl acetate and washed with 10% aq. sodium carbonate, saturated sodium chloride, dried over anhydrous sodium sulfate and filtered. Concentration gives the crude product that was chromatographed on silica gel using ethyl acetate/hexanes to give 50 (1.45 g).

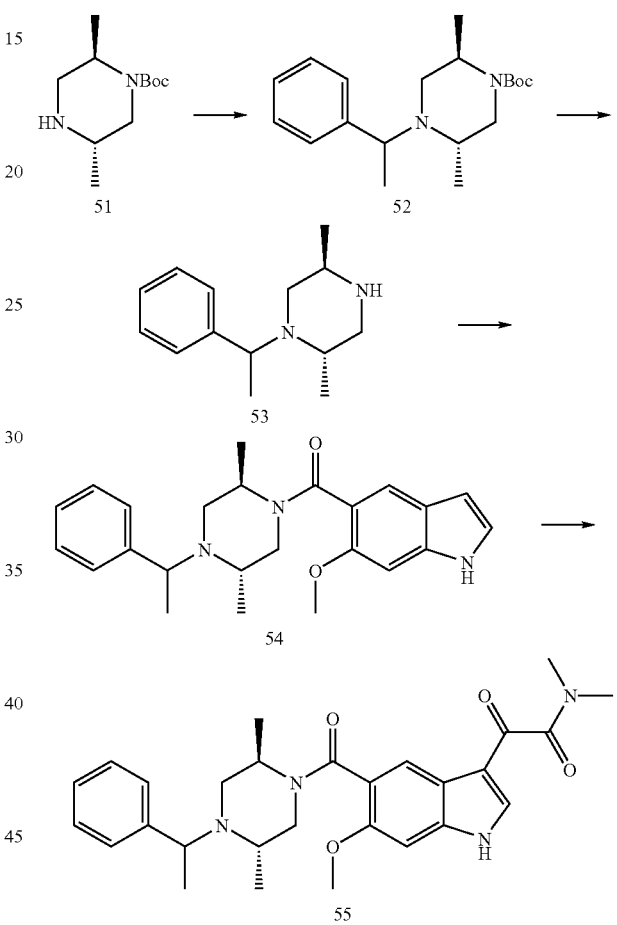

Synthesis of 52: 2R,5S-transdimethyl piperazine 51 (5.0 g) was dissolved in 15 mL ethanol, to this was aded 2-bromo-ethylbenzene (4.4 g). Thereaction mixture was stirred at 40° C. for 30 min., cooled to room tempeature and concentrated to dryness on a rotary evaporator. The residue was taken up in ethyl acetate and washed with 10% aqueous sodium carbonate, brine and dried over anhydrous sodium sulfate. Filtration and concentration gave crude material that was purified by chromatography on silica gel using ethyl acetate/hexanes gave 52 (5.4 g).

Synthesis of 53: 5 g of 52 was dissolved in 60 mL methylene chloride and treated with 60 mL 2 M hydrochloric acid in ether for 3 h. The solvent was removed and the solid obtained was washed with ether and hexanes and dried under high vacuum to give 53 as the hydrochloride salt, 3.6 g.

Synthesis of 54: 53 (1.32 g), was dissolved in 20 mL methylene chloride and treated with 6-methoxy-5-indole carboxylic acid (37) (0.9 g) in the presence of 1-ethyl-3-(3-dimethylaminopropyl)carbodiimide (1.04 g), 800 µL triethylamine and catalytic DMAP, overnight. The reaction mixture was concentrated and the residue taken up in ethyl acetate, washed with 10% aqueous sodium carbonate, brine and dried over anhydrous sodium sulfate. Filtration and concentration gave crude material that was purified by chromatography on silica gel using ethyl acetate/hexanes to give 54 (0.95 g).

Synthesis of 55: 0.6 g of 54 was dissolved in 20 mL dry methylene chloride. The reaction mixture was purged with nitrogen and placed in an ice bath. To this was added, 2 mL of a 2M oxalyl chloride in methylene chloride. The reaction mixture was stirred at room temperature for 1 h and then at room temperature for 2 h. Reaction mixture was concentrated on a rotary and after drying on a vacuum pump for 15 min. the residue (a yellow solid) was dissolved in 15 mL dry methylene chloride, to which was added 2 mL of a 2M solution of dimethylamine in tetrahydrofuran. 30 minutes later the reaction mixture was concentrated and the residue was taken up in ethyl acetate and washed with 10% aq. sodium carbonate, saturated sodium chloride, dried over anhydrous sodium sulfate and filtered. Concentration gives the crude product that was chromatographed on silica gel using ethyl acetate/hexanes to give 55 (0.78 g).

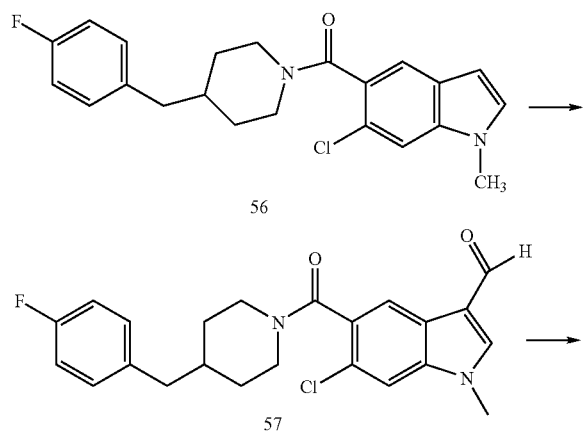

-continued

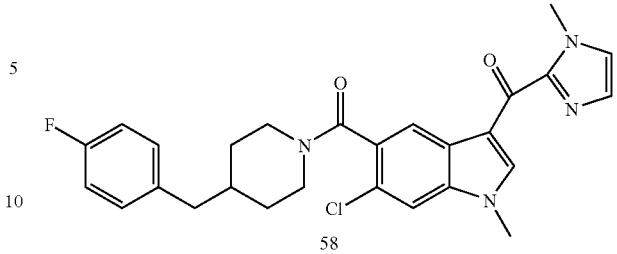

Synthesis of 57: 7.65 g (19.97 mmol) of the indole 56 was dissolved in 80 mL anhydrous dimethylformamide and was cooled in an ice-bath. Under an inert atmosphere, 40 mL (2M solution in dichloromethane) of oxalylchloride was added dropwise over 20 min. After stirring for 15 min. at 0° C., the reaction was allowed to warm up to ambient temperature and stirring continued for 1 h. The reaction mixture was poured in to water and extracted with ethylacetate (3×100 mL). The combined extract was washed with water and dried over sodium sulfate and evaporated. The product was further purified by column chromatography with ethylacetate:hexane (30:70) to yield 8 g (97.5%) of the aldehyde 57.

Synthesis of 58: To a solution of 1-methylimidazole (149 mg) in tetrahydrofuran (10 mL) was added n-butyl lithium (1.14 mL, 1.82 mmol, 1.6 M in hexane) dropwise at −78° C. The reaction mixture was stirred at −40° C. for 30 min. 57 (500 mg) in tetrahydrofuran (10 mL) was added. The reaction mixture was warmed to ambient temperature and stirred overnight. The reaction mixture was quenched with ammonium chloride (saturated), extracted with ethyl acetate. The combined organic layer was washed with brine, dried and concentrated. The crude mixture was reflux with phenyl hydrazine (0.6 mL) in ethanol (10 mL) to remove 57, which was not consumed in the reaction. Removal of the solvent, the residue was purified by chromatography on silica gel eluting with ethyl acetate:hexane (4:1) to give 120 mg of 58

Using the foregoing procedures, the compounds of Tables 2 and 3 were prepared and many tested for their ability to inhibit p38-α kinase. It was found that the compounds in Tables 2 and 3 provide $IC_{50}$ values for inhibition of p38-α in the range of 0.1–1.5 µMol.

TABLE 2

| Compd. # | STRUCTURE | MW (Calcd.) | MW (Obsd.) |
|---|---|---|---|
| 1 | 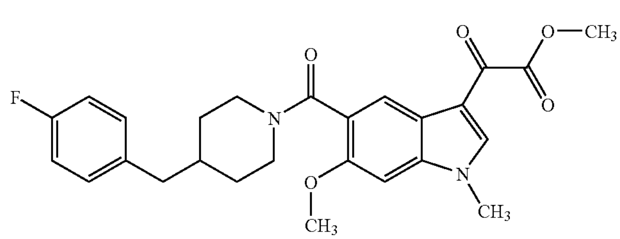 | 466 | 466 |

TABLE 2-continued

| Compd. # | STRUCTURE | MW (Calcd.) | MW (Obsd.) |
| --- | --- | --- | --- |
| 2 | 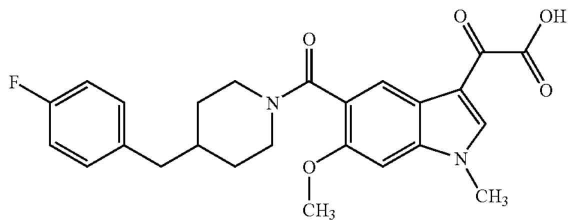 | 452 | 453 |
| 3 | 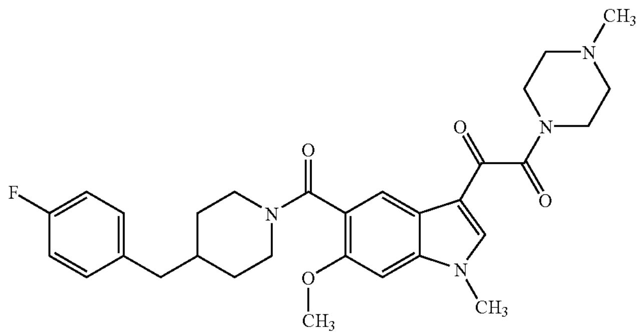 | 535 | 534 |
| 4 | 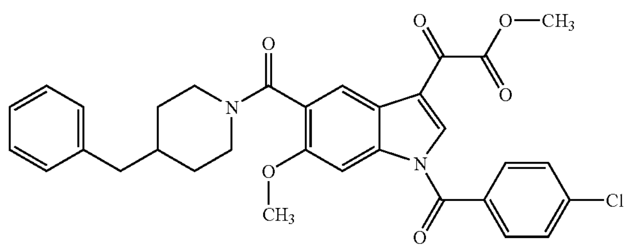 | 573 | 573 |
| 5 | 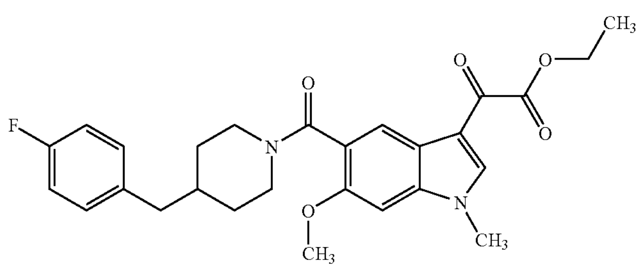 | 480 | 480 |
| 6 | 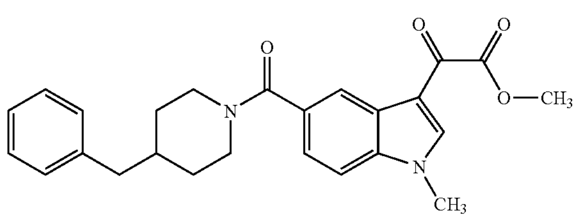 | 418 | 418 |

TABLE 2-continued

| Compd. # | STRUCTURE | MW (Calcd.) | MW (Obsd.) |
|---|---|---|---|
| 7 | 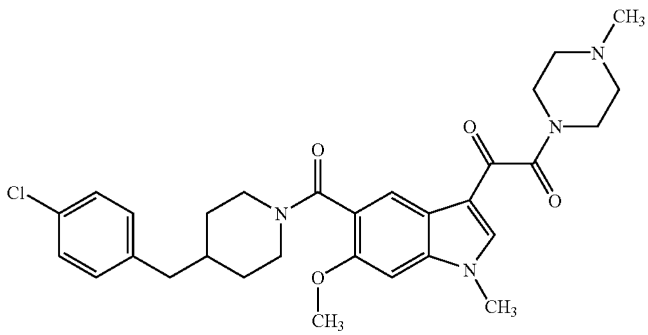 | 551 | 551 |
| 8 | 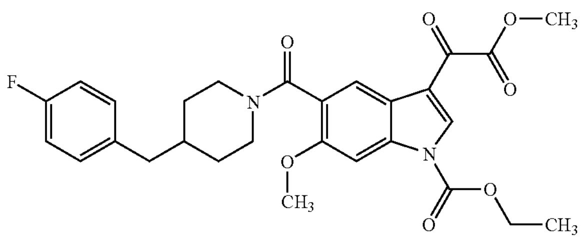 | 524 | 523 |
| 9 | 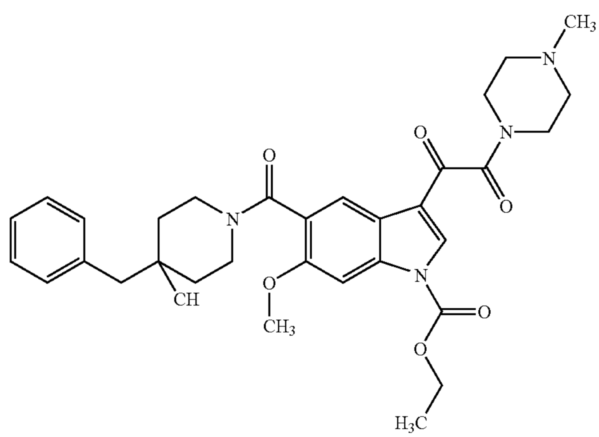 | 590 | 590 |
| 10 | 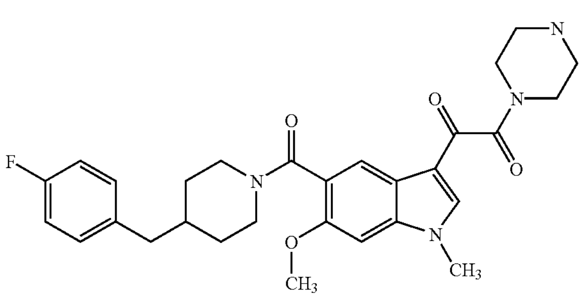 | 521 | 520 |

TABLE 2-continued

| Compd. # | STRUCTURE | MW (Calcd.) | MW (Obsd.) |
|---|---|---|---|
| 11 | 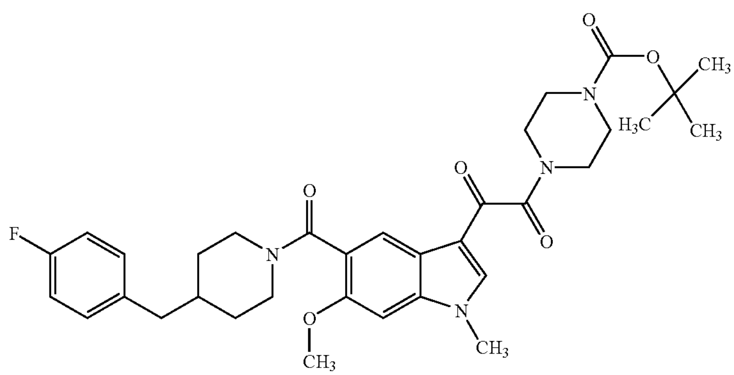 | 620 | 620 |
| 12 | 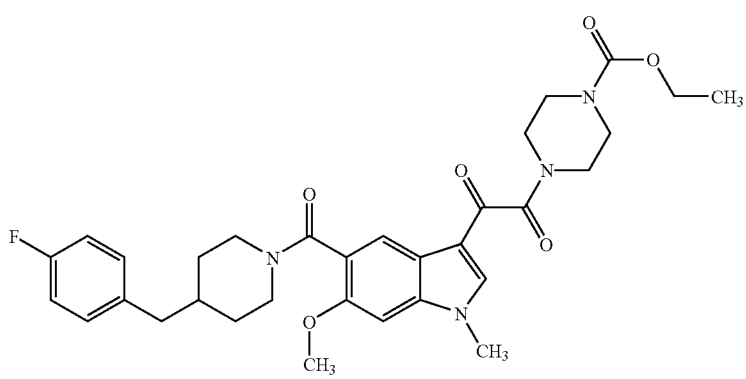 | 592 | 592 |
| 13 | 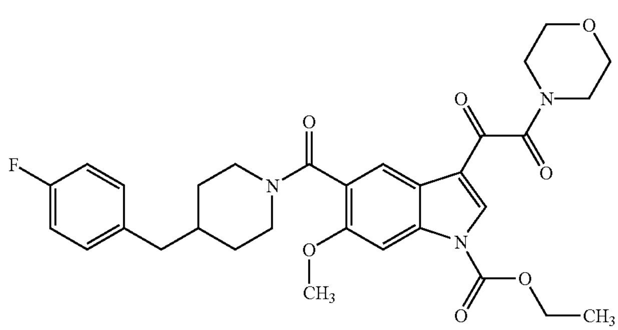 | 579 | 580 |
| 14 | 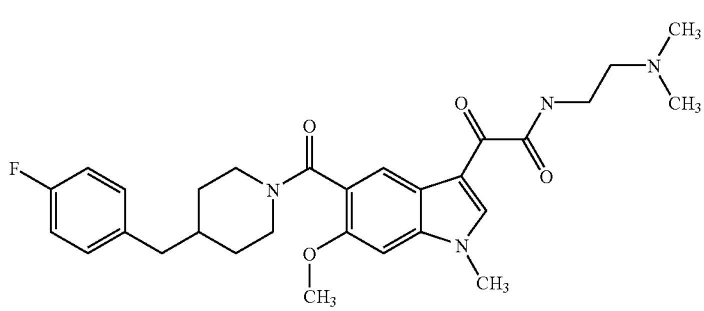 | 523 | 522 |

TABLE 2-continued

| Compd. # | STRUCTURE | MW (Calcd.) | MW (Obsd.) |
| --- | --- | --- | --- |
| 15 | 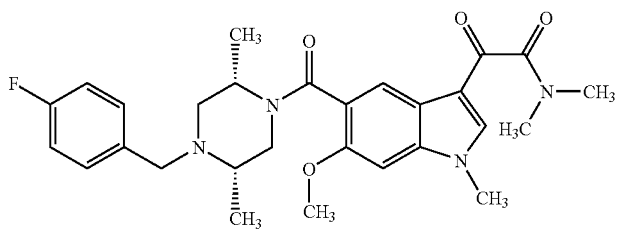 | 509 | 509 |
| 16 | 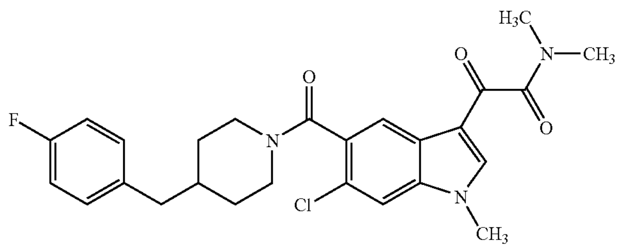 | 484 | 484 |
| 17 | 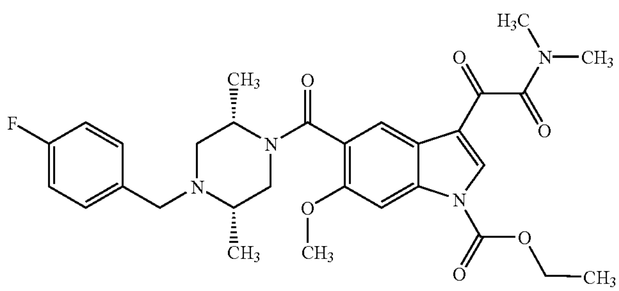 | 567 | 567 |
| 18 | 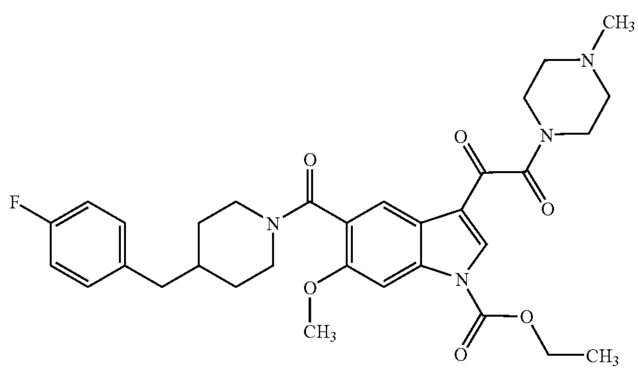 | 593 | 592 |
| 19 | 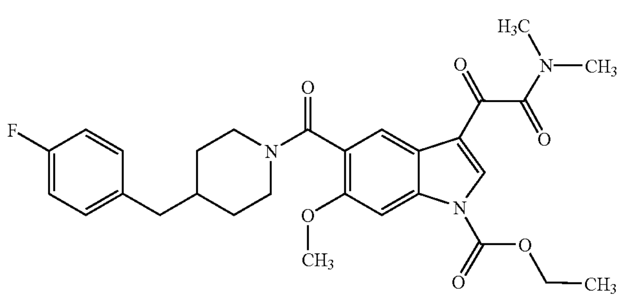 | 537 | 537 |

TABLE 2-continued

| Compd. # | STRUCTURE | MW (Calcd.) | MW (Obsd.) |
|---|---|---|---|
| 20 | 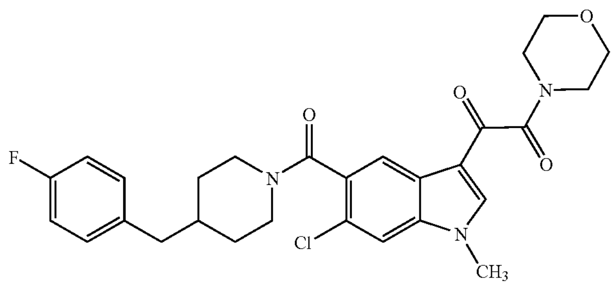 | 526 | 525 |
| 21 | 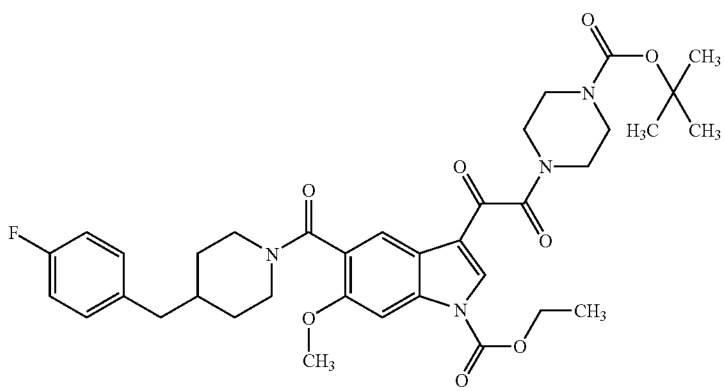 | 678 | 678 |
| 22 | 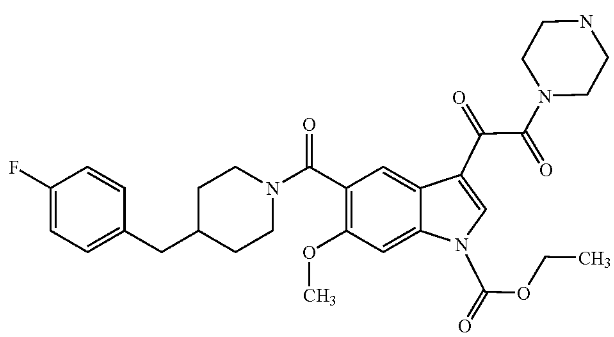 | 579 | 578 |
| 23 | 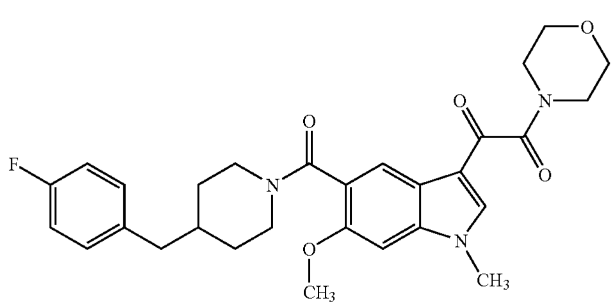 | 522 | 522 |

TABLE 2-continued

| Compd. # | STRUCTURE | MW (Calcd.) | MW (Obsd.) |
|---|---|---|---|
| 24 | 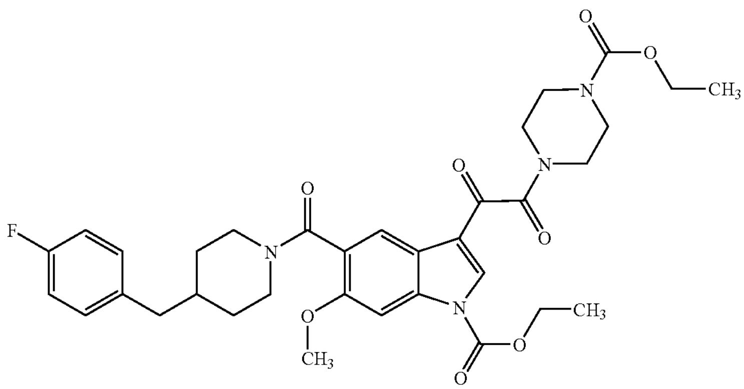 | 650 | 650 |
| 25 | 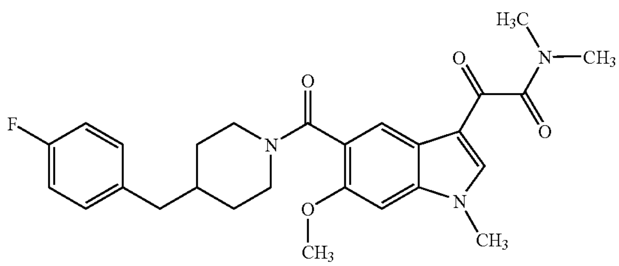 | 480 | 480 |
| 26 | 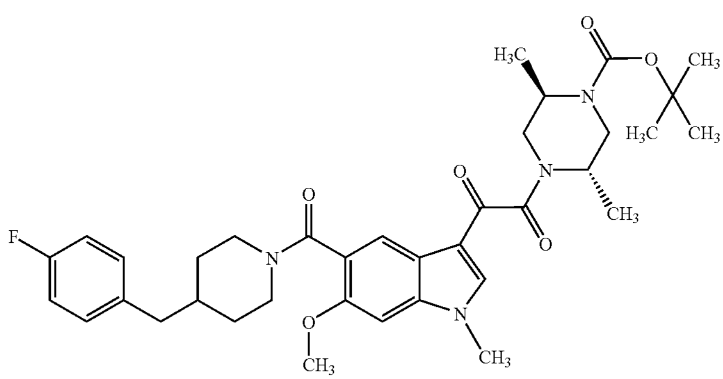 | 648 | 648 |
| 27 | 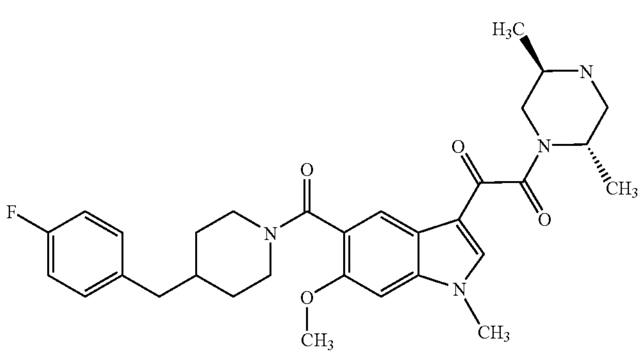 | 549 | 548 |

TABLE 2-continued

| Compd. # | STRUCTURE | MW (Calcd.) | MW (Obsd.) |
|---|---|---|---|
| 28 | 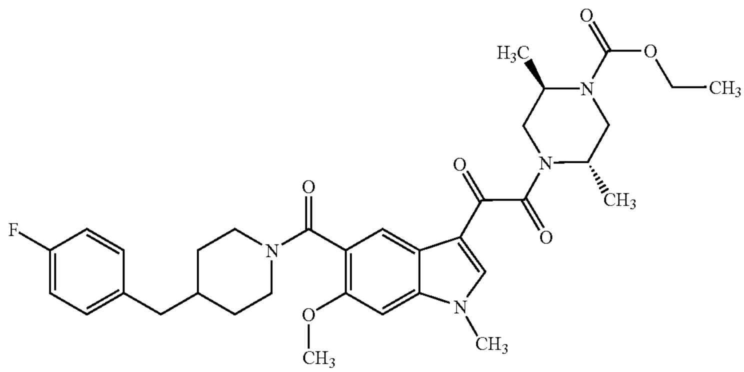 | 620 | 620 |
| 29 | 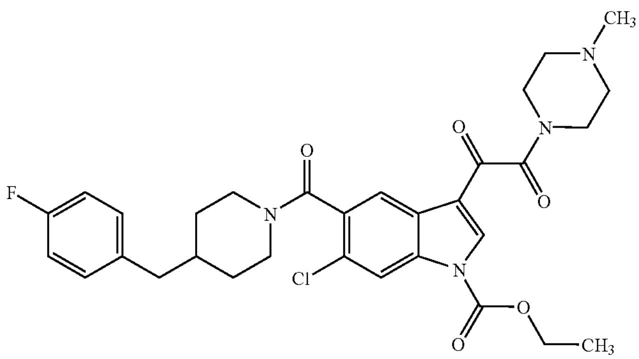 | 597 | 596 |
| 30 | 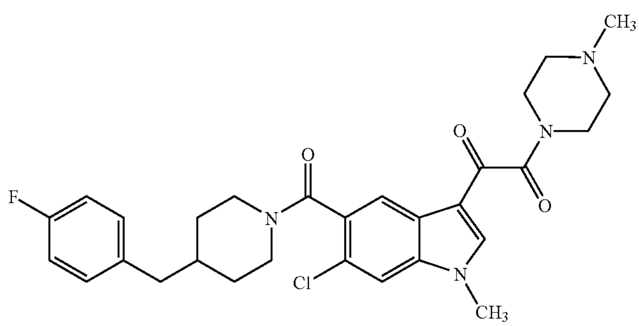 | 539 | 538 |
| 31 | 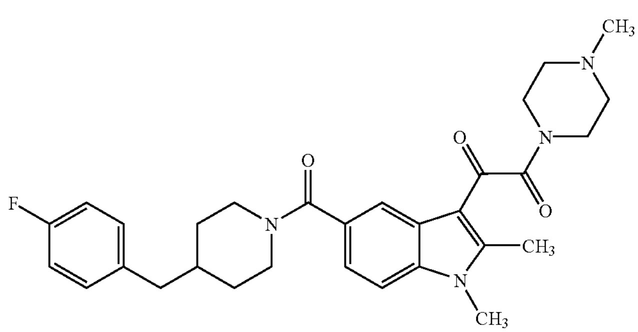 | 519 | 519 |

TABLE 2-continued
| Compd. # | STRUCTURE | MW (Calcd.) | MW (Obsd.) |
| --- | --- | --- | --- |
| 32 | 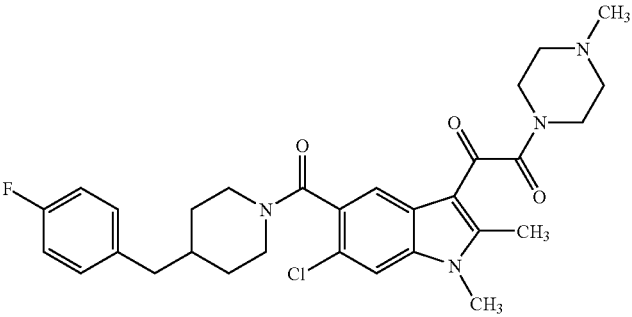 | 553 | 553 |
| 33 | 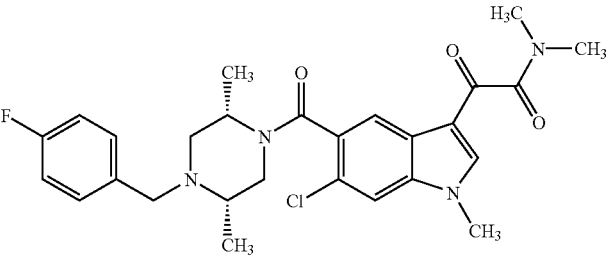 | 513 | 513 |
| 34 | 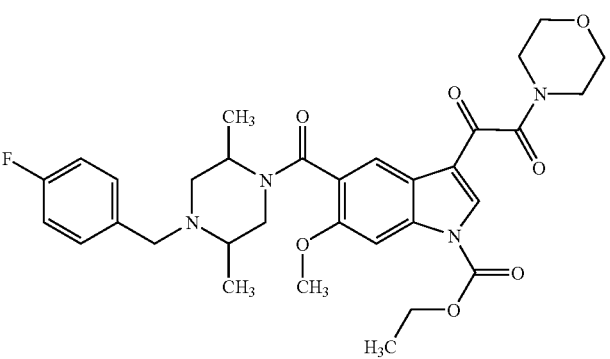 | 609 | 609 |
| 35 | 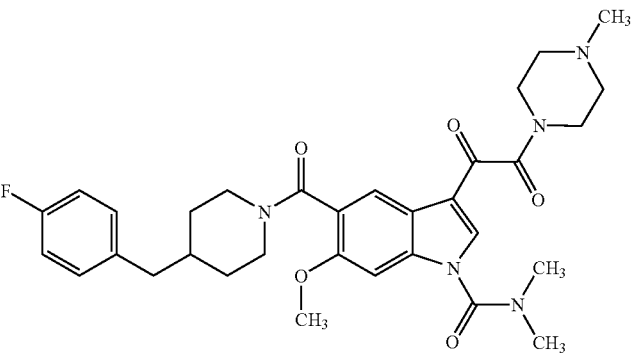 | 592 | 591 |

TABLE 2-continued

| Compd. # | STRUCTURE | MW (Calcd.) | MW (Obsd.) |
| --- | --- | --- | --- |
| 36 | 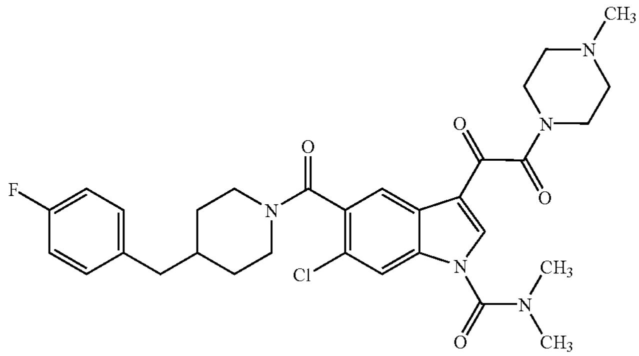 | 596 | 595 |
| 37 | 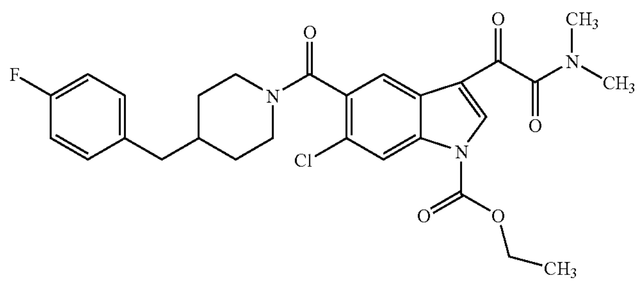 | 542 | 541 |
| 38 | 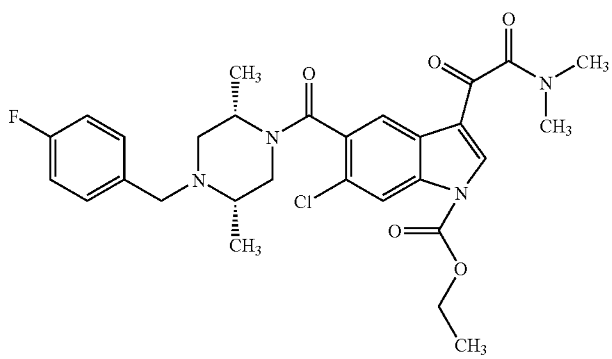 | 571 | 571 |
| 39 | 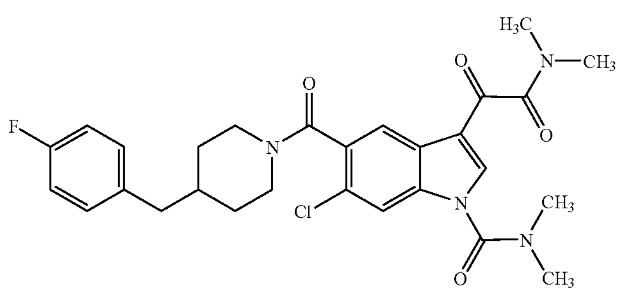 | 541 | 541 |
| 40 | 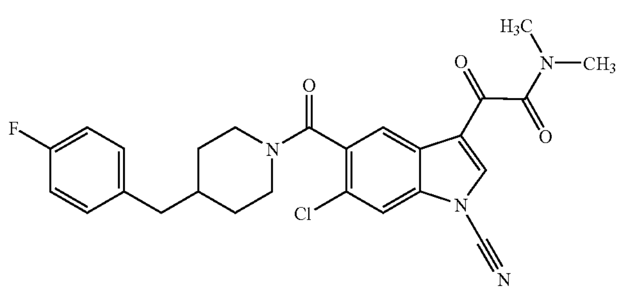 | 494 | 494 |

TABLE 2-continued

| Compd. # | STRUCTURE | MW (Calcd.) | MW (Obsd.) |
|---|---|---|---|
| 41 | 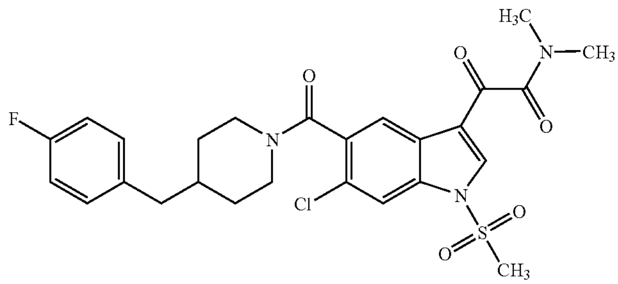 | 548 | 548 |
| 42 | 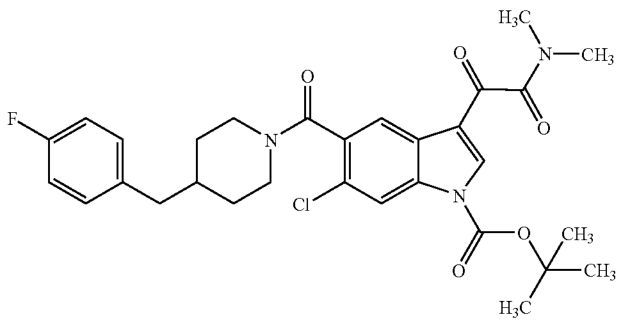 | 570 | 570 |
| 43 | 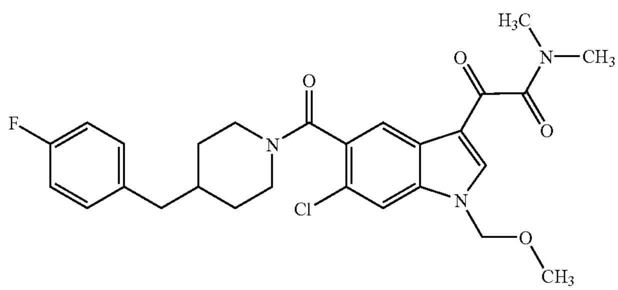 | 514 | 513 |
| 44 | 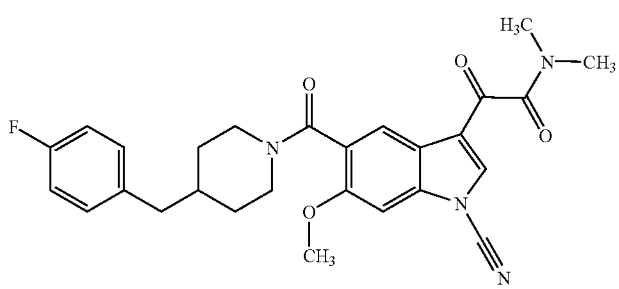 | 490 | 490 |
| 45 | 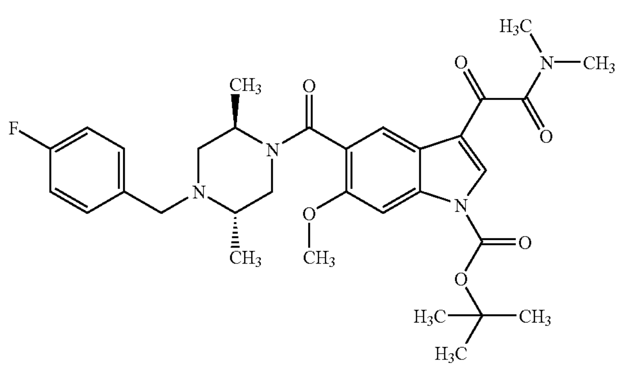 | 595 | 595 |

TABLE 2-continued

| Compd. # | STRUCTURE | MW (Calcd.) | MW (Obsd.) |
|---|---|---|---|
| 46 | 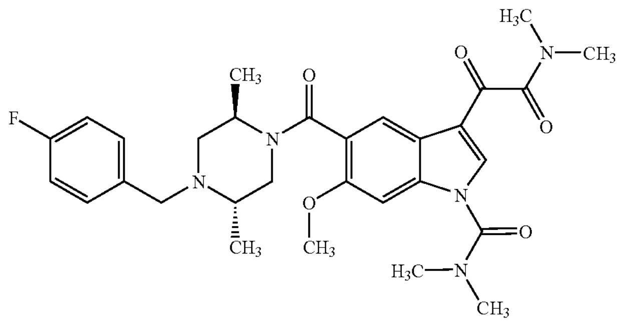 | 566 | 566 |
| 47 | 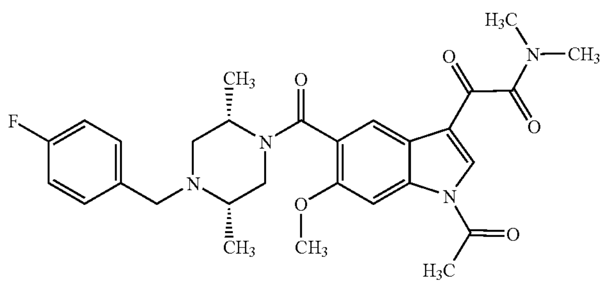 | 537 | 537 |
| 48 | 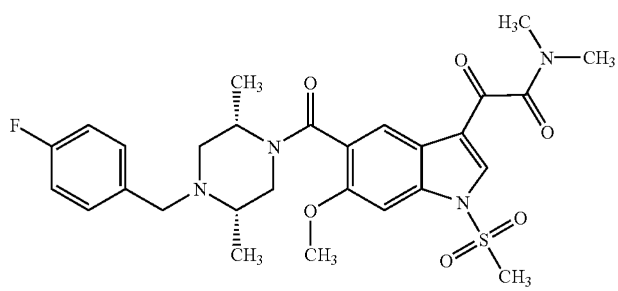 | 573 | 573 |
| 49 | 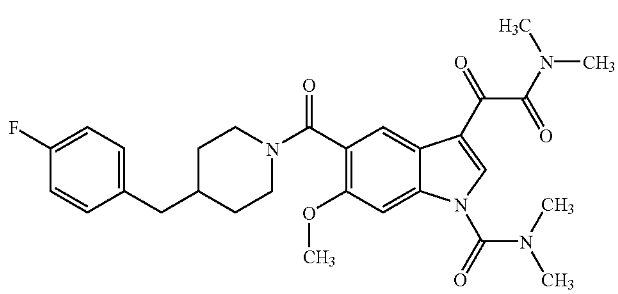 | 536 | 536 |
| 50 | 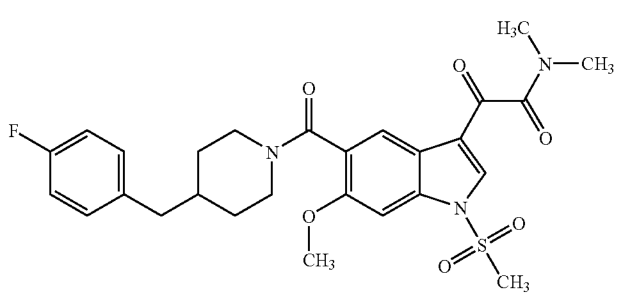 | 543 | 543 |

TABLE 2-continued

| Compd. # | STRUCTURE | MW (Calcd.) | MW (Obsd.) |
|---|---|---|---|
| 51 | 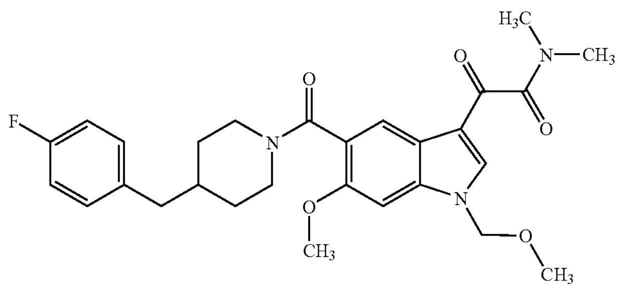 | 509 | 509 |
| 52 | 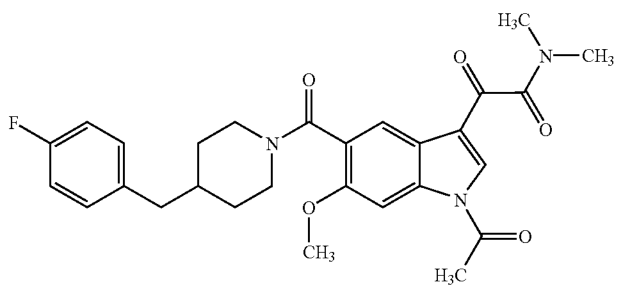 | 507 | 507 |
| 53 | 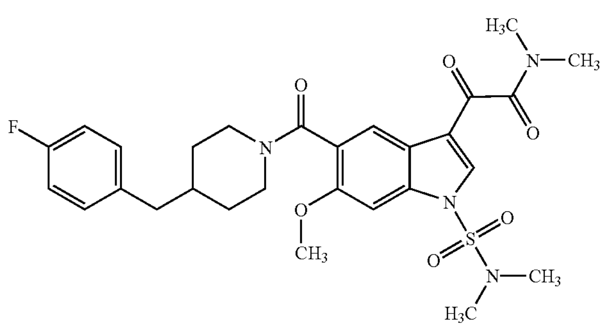 | 572 | 572 |
| 54 | 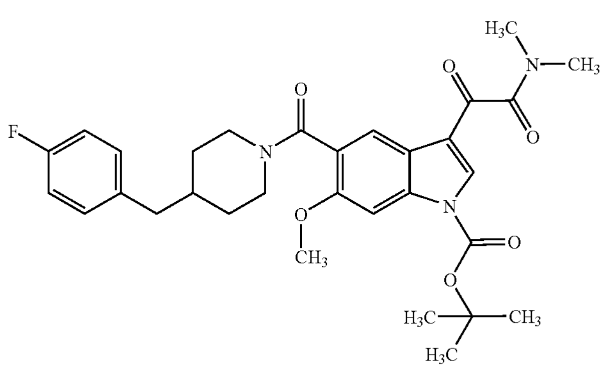 | 565 | 565 |

TABLE 2-continued

| Compd. # | STRUCTURE | MW (Calcd.) | MW (Obsd.) |
| --- | --- | --- | --- |
| 55 | 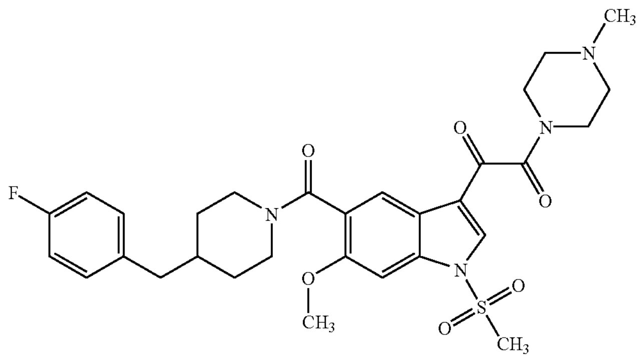 | 599 | 599 |
| 56 | 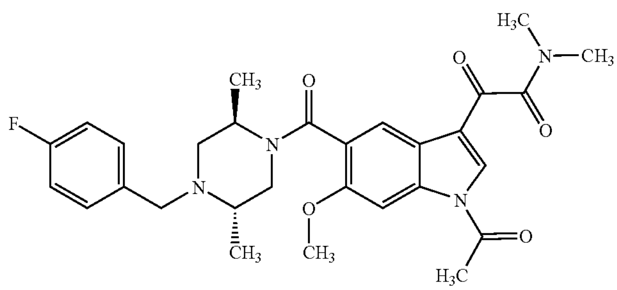 | 537 | 537 |
| 57 | (Chiral) | 513 | 513 |
| 58 | 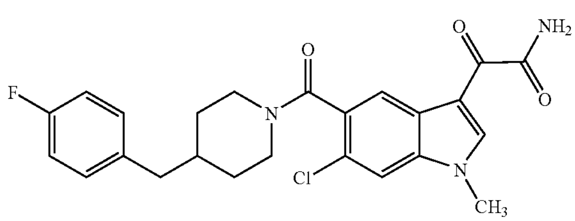 | 456 | 456 |
| 59 | 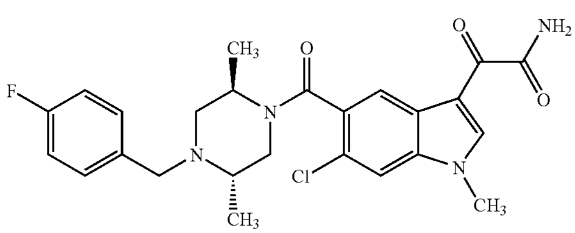 | 485 | 485 |

TABLE 2-continued

| Compd. # | STRUCTURE | MW (Calcd.) | MW (Obsd.) |
|---|---|---|---|
| 60 | 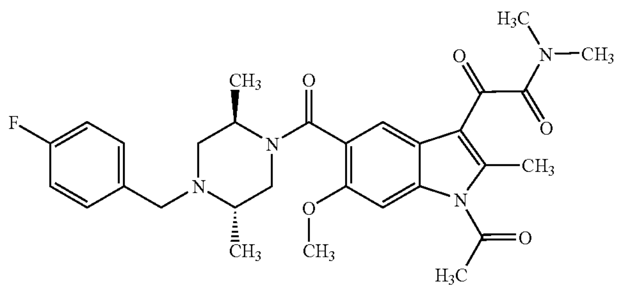 | 551 | 551 |
| 61 | 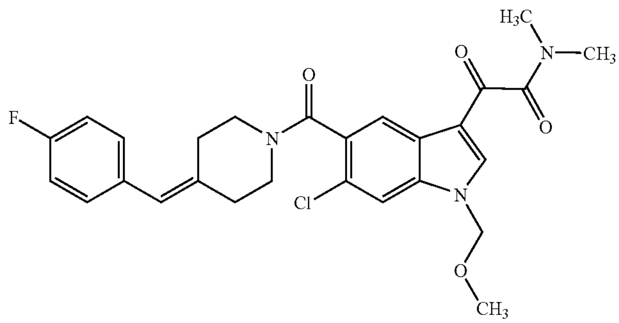 | 511 | 511 |
| 62 | 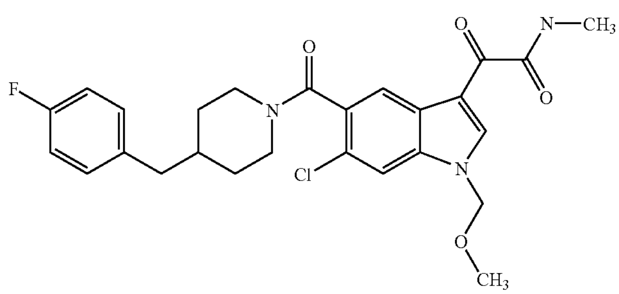 | 499 | 500 |
| 63 | 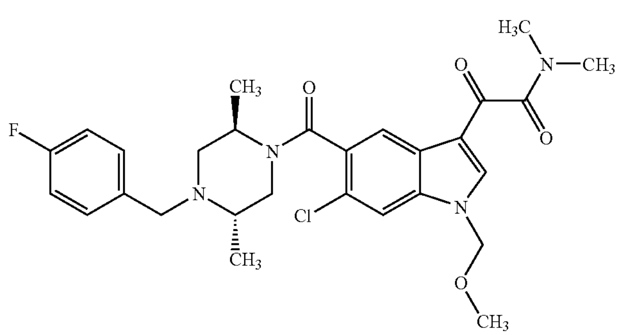 | 543 | 543 |

TABLE 2-continued

| Compd. # | STRUCTURE | MW (Calcd.) | MW (Obsd.) |
| --- | --- | --- | --- |
| 64 | 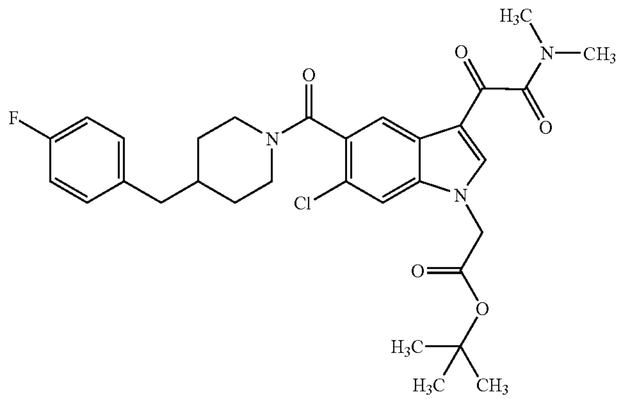 | 584 | 584 |
| 65 | 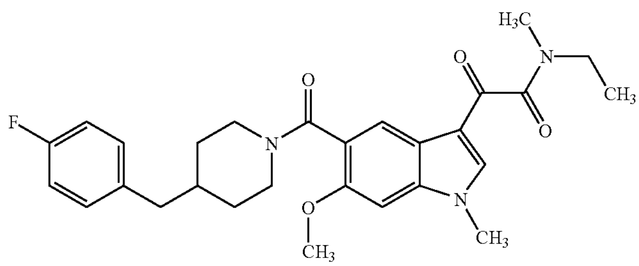 | 493 | 493 |
| 66 | 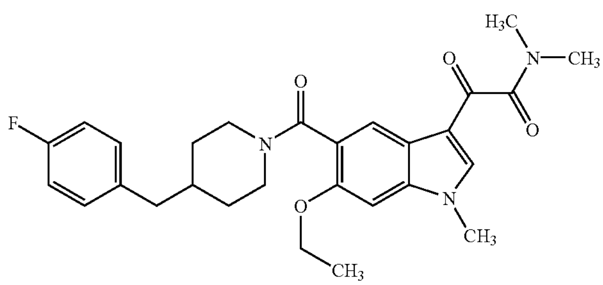 | 494 | 494 |
| 67 | 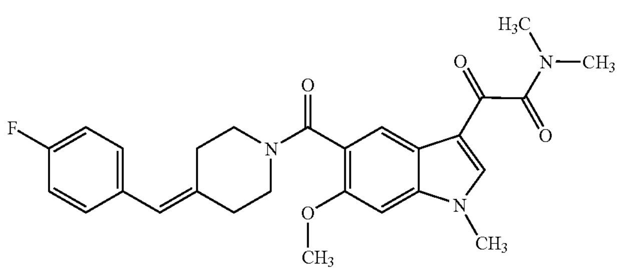 | 477 | 477 |
| 68 | 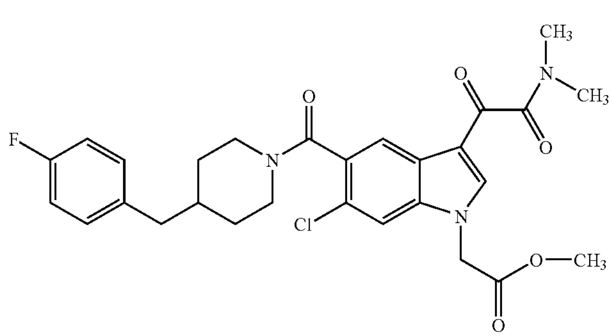 | 542 | 542 |

TABLE 2-continued

| Compd. # | STRUCTURE | MW (Calcd.) | MW (Obsd.) |
|---|---|---|---|
| 69 | 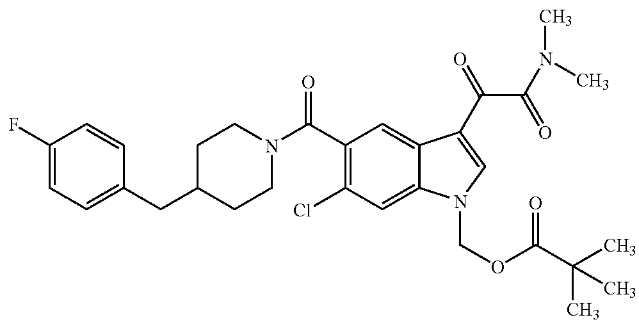 | 584 | 584 |
| 70 | 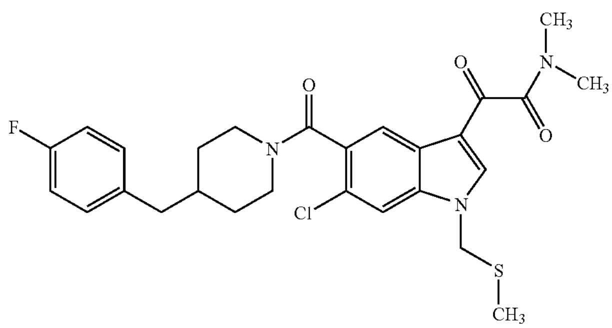 | 530 | 529 |
| 71 | 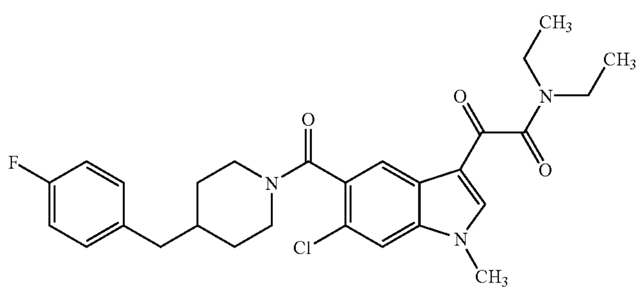 | 512 | 511 |
| 72 | 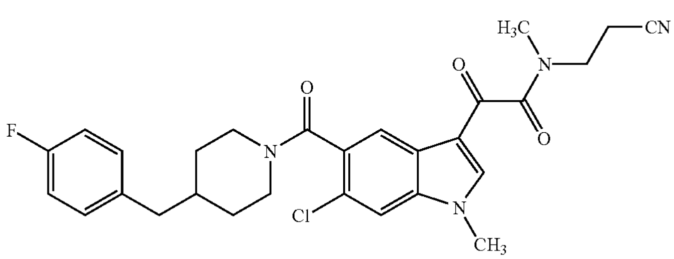 | 523 | 522 |
| 73 | 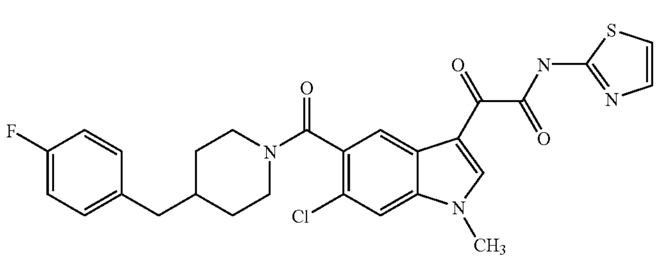 | 539 | 539 |

TABLE 2-continued

| Compd. # | STRUCTURE | MW (Calcd.) | MW (Obsd.) |
|---|---|---|---|
| 74 | 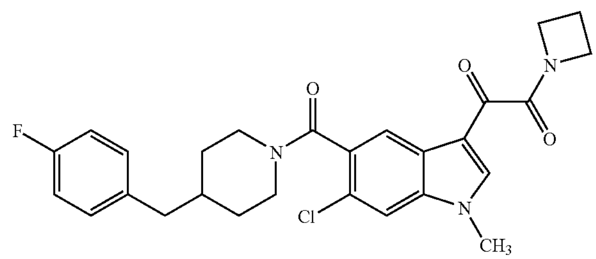 | 495 | 495 |
| 75 | 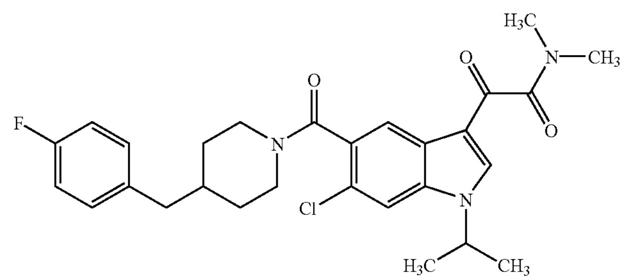 | 512 | 511 |
| 76 | 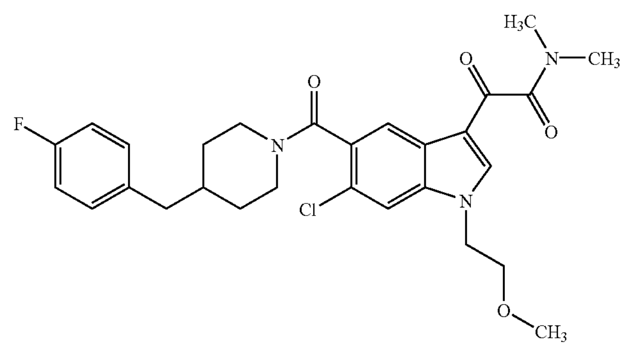 | 528 | 528 |
| 77 | 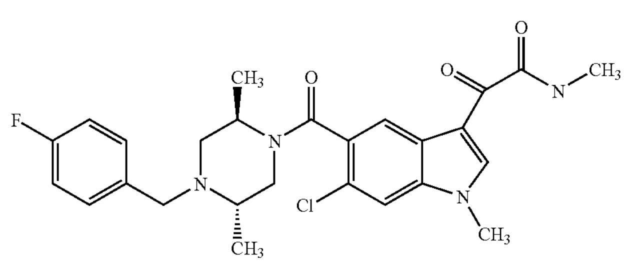 | 499 | 499 |
| 78 | 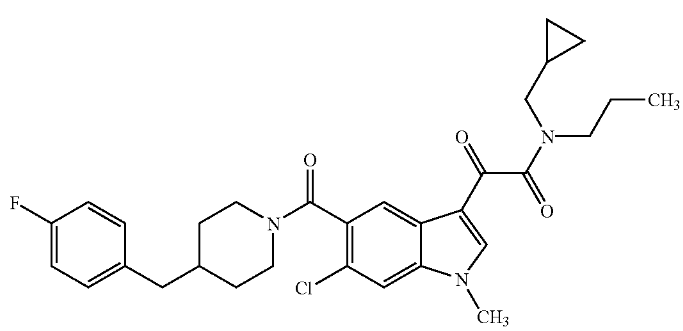 | 552 | 551 |

TABLE 2-continued

| Compd. # | STRUCTURE | MW (Calcd.) | MW (Obsd.) |
|---|---|---|---|
| 79 | 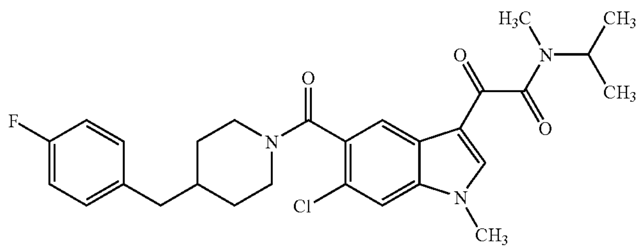 | 512 | 511 |
| 80 | 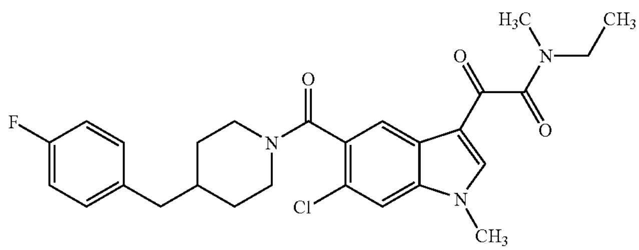 | 498 | 497 |
| 81 | 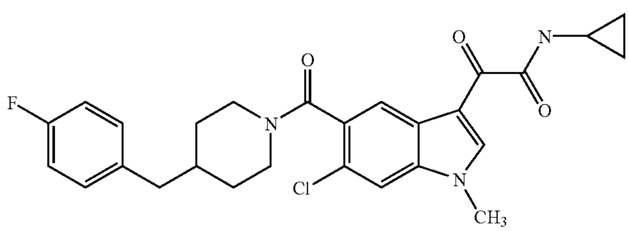 | 496 | 495 |
| 82 | 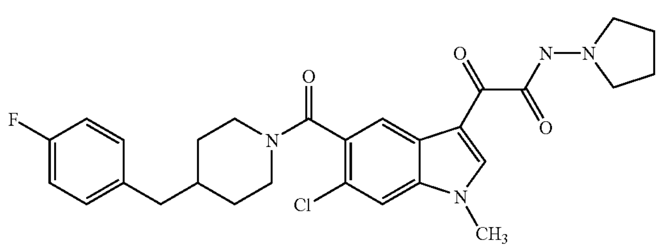 | 525 | 525 |
| 83 | 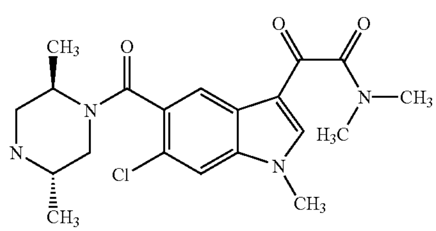 | 405 | 405 |
| 84 | 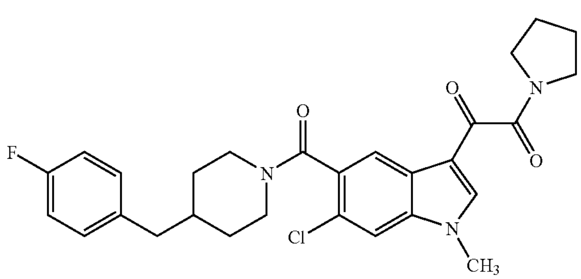 | 510 | 509 |

TABLE 2-continued

| Compd. # | STRUCTURE | MW (Calcd.) | MW (Obsd.) |
| --- | --- | --- | --- |
| 85 | 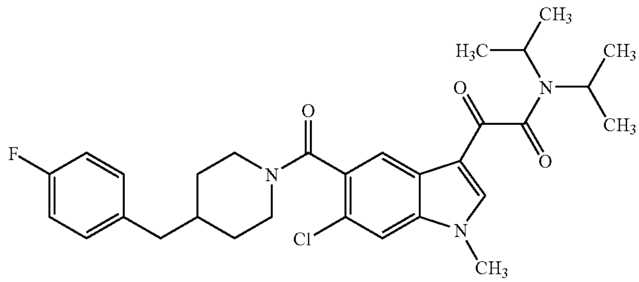 | 540 | 539 |
| 86 | 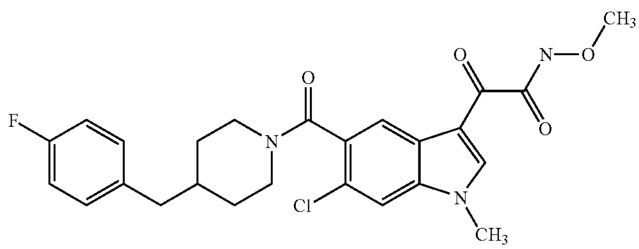 | 485 | 486 |
| 87 | 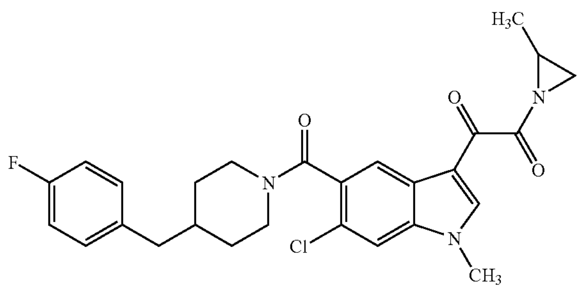 | 495 | 495 |
| 88 | 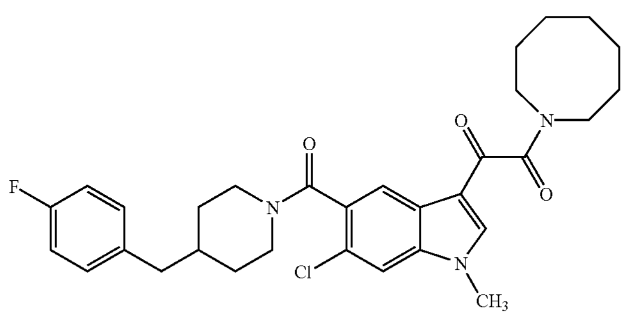 | 552 | 551 |
| 89 | 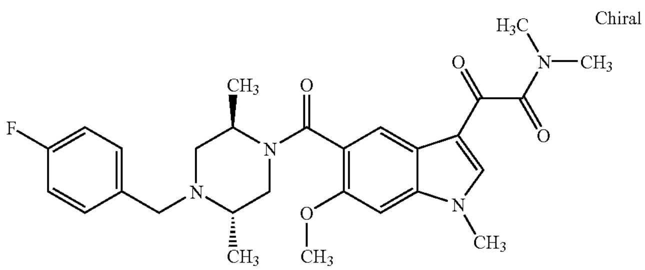 | 508 | 508 |

TABLE 2-continued

| Compd. # | STRUCTURE | MW (Calcd.) | MW (Obsd.) |
|---|---|---|---|
| 90 | 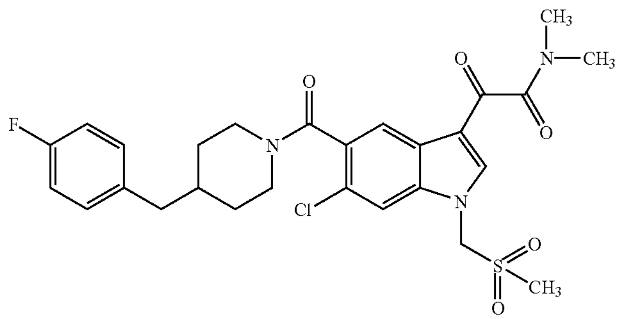 | 562 | 562 |
| 91 | 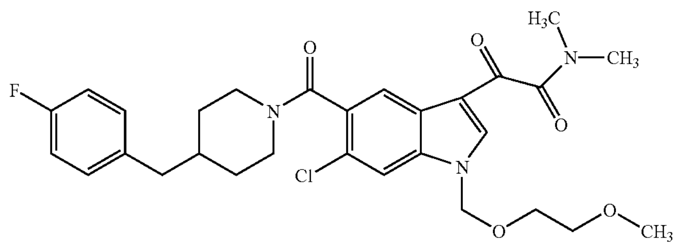 | 558 | 558 |
| 92 | 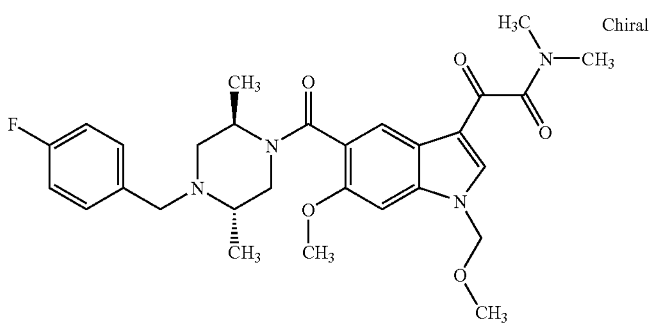 | 539 | 539 |
| 93 | 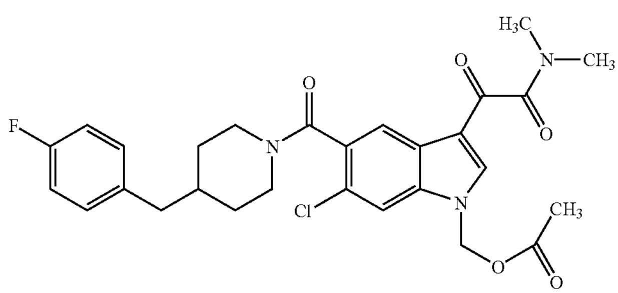 | 542 | 542 |
| 94 | 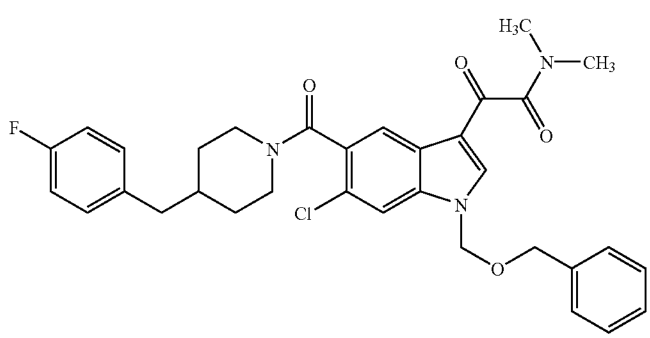 | 590 | 590 |

TABLE 2-continued

| Compd. # | STRUCTURE | MW (Calcd.) | MW (Obsd.) |
|---|---|---|---|
| 95 | 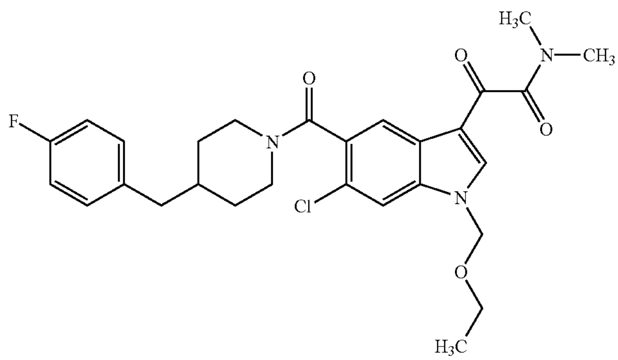 | 528 | 528 |
| 96 | Chiral | 555 | 555 |
| 97 | 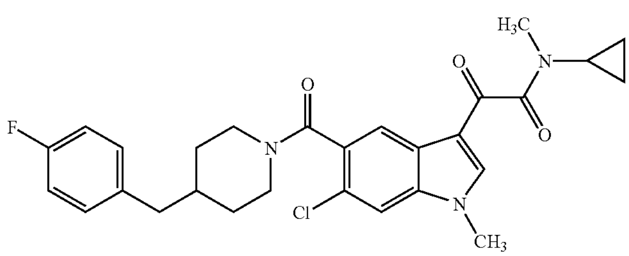 | 510 | 509 |
| 98 | 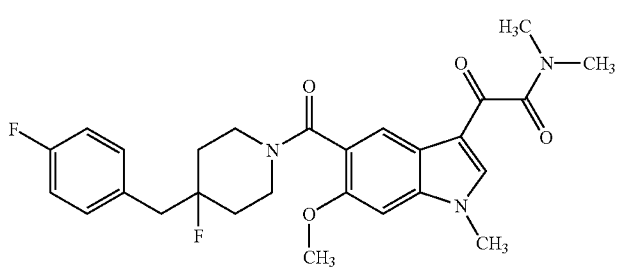 | 497 | 497 |
| 99 | 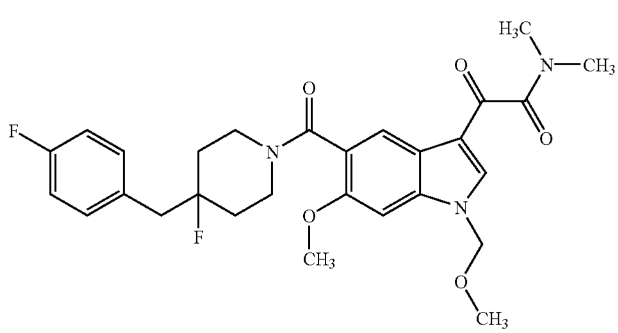 | 527 | 527 |

TABLE 2-continued
| Compd. # | STRUCTURE | MW (Calcd.) | MW (Obsd.) |
|---|---|---|---|
| 100 | 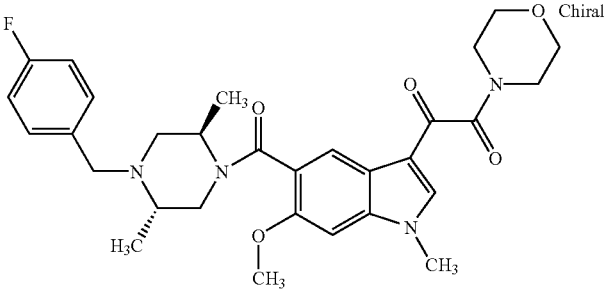 | 550 | 550 |
| 101 | 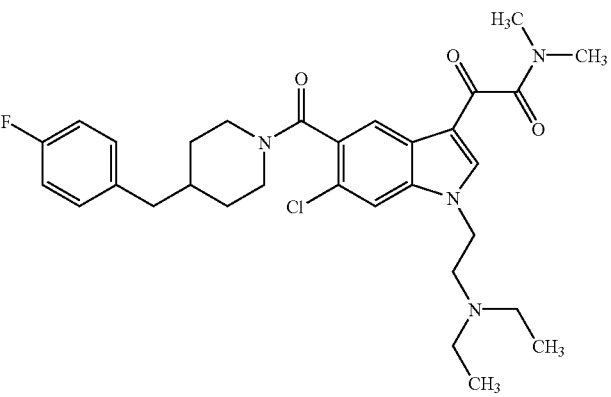 | 569 | 569 |
| 102 | 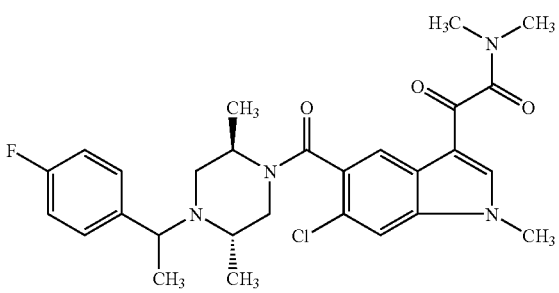 | 527 | 527 |
| 103 | 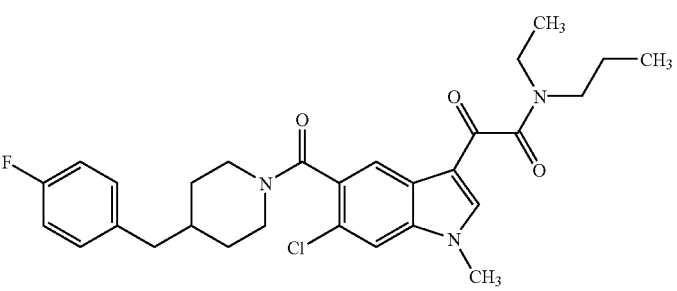 | 526 | 525 |
| 104 | 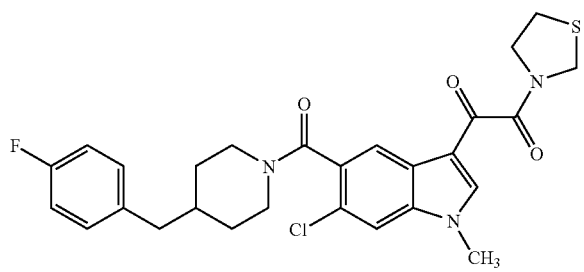 | 528 | 528 |

TABLE 2-continued

| Compd. # | STRUCTURE | MW (Calcd.) | MW (Obsd.) |
|---|---|---|---|
| 105 | 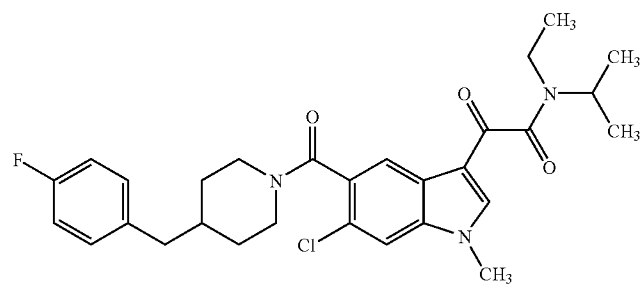 | 526 | 525 |
| 106 | 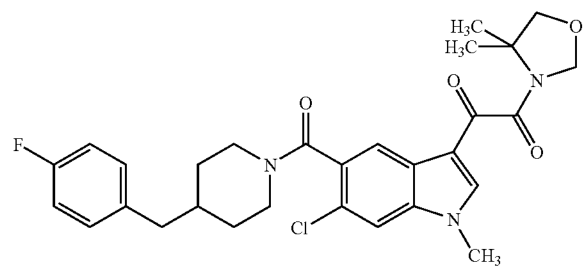 | 540 | 539 |
| 107 | 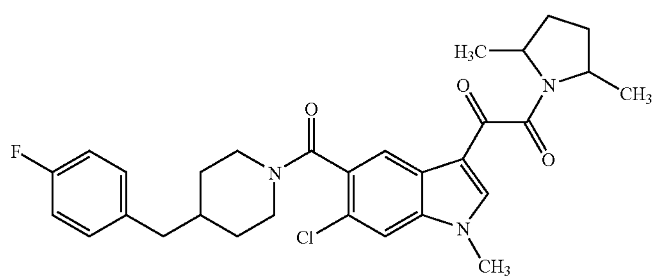 | 538 | 537 |
| 108 | 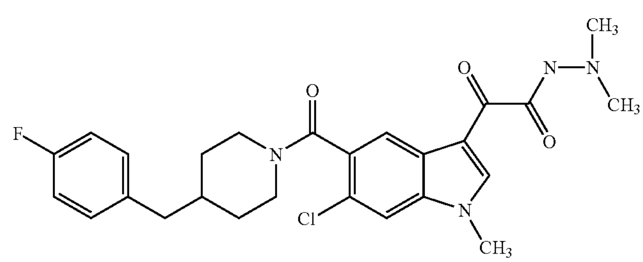 | 498 | 498 |
| 109 | 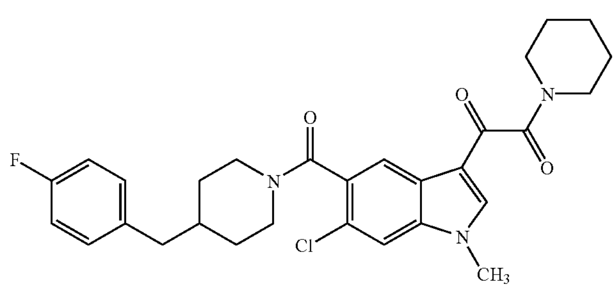 | 524 | 523 |

TABLE 2-continued

| Compd. # | STRUCTURE | MW (Calcd.) | MW (Obsd.) |
| --- | --- | --- | --- |
| 110 | 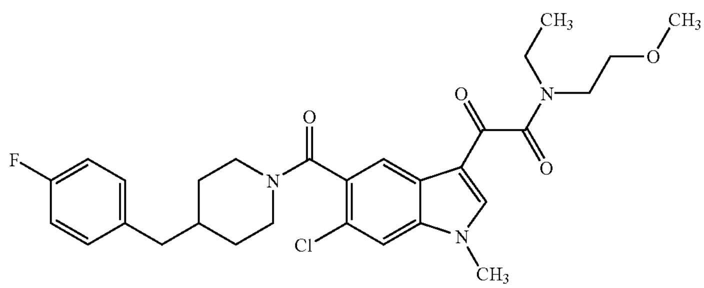 | 542 | 541 |
| 111 | 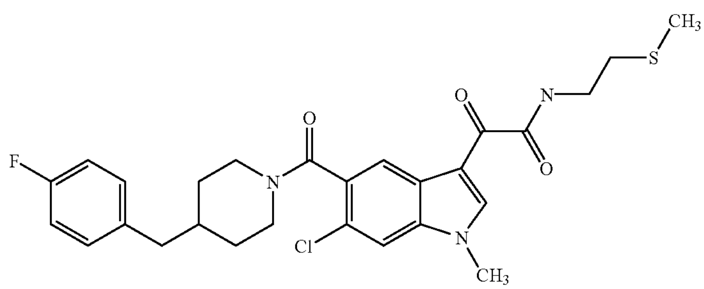 | 530 | 529 |
| 112 | 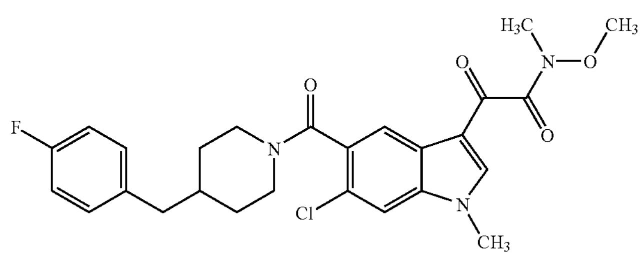 | 499 | 500 |
| 113 | 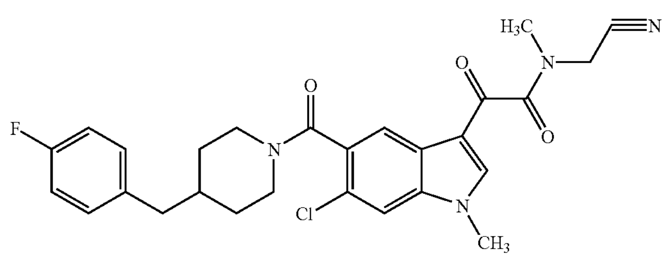 | 508 | 508 |
| 114 | 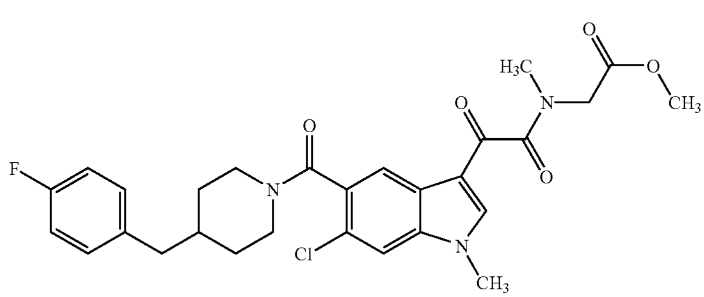 | 542 | 541 |

TABLE 2-continued

| Compd. # | STRUCTURE | MW (Calcd.) | MW (Obsd.) |
| --- | --- | --- | --- |
| 115 | 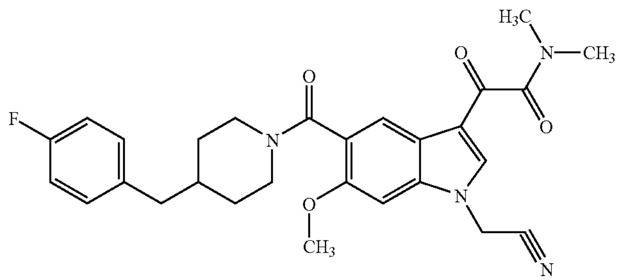 | 504 | 504 |
| 116 | 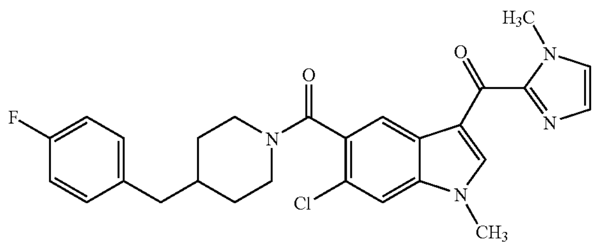 | 492 | 504 |

TABLE 3

| Compd. # | MOLSTRUCTURE | MW (Calcd.) | MW (Obs.) |
| --- | --- | --- | --- |
| 117 | | 472.5858 | 472.5858 |
| 118 | | 404.4636 | 404.4636 |
| 119 | | 390.4368 | 390.4368 |

TABLE 3-continued
| Compd. # | MOLSTRUCTURE | MW (Calcd.) | MW (Obs.) |
|---|---|---|---|
| 120 | 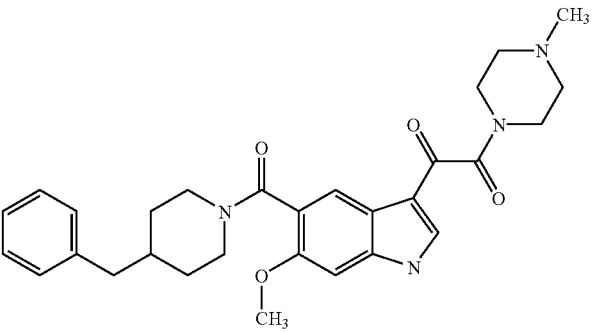 | 502.6116 | 502.6116 |
| 121 | 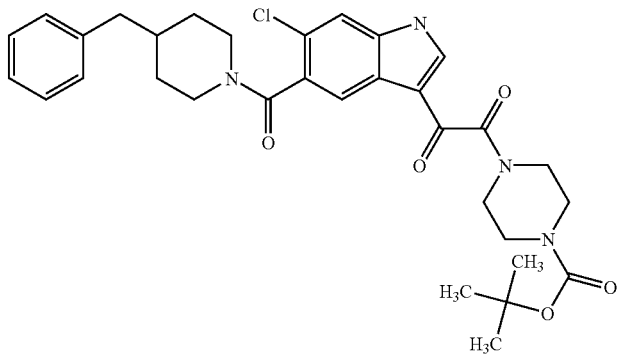 | 558.6752 | 558.6752 |
| 122 | 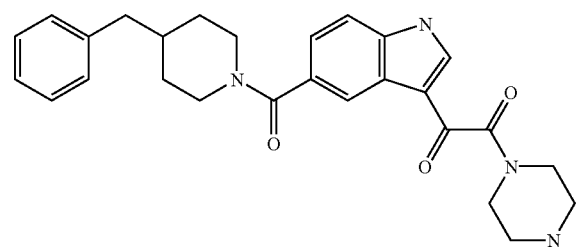 | 458.559 | 458.559 |
| 123 | 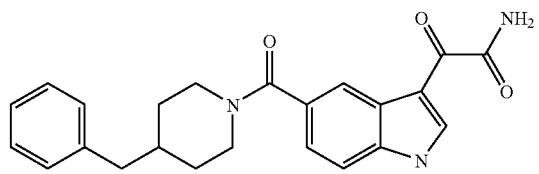 | 389.4527 | 389.4527 |
| 124 | 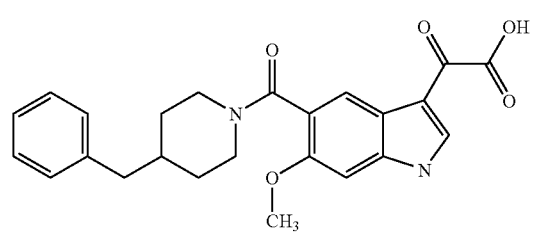 | 420.4626 | 420.4626 |

TABLE 3-continued

| Compd. # | MOLSTRUCTURE | MW (Calcd.) | MW (Obs.) |
|---|---|---|---|
| 125 | | 516.6384 | 516.6384 |
| 126 | | 504.6027 | 504.6027 |
| 127 | | 422.4537 | 422.4537 |
| 128 | | 525.021 | 525.021 |
| 129 | | 434.4894 | 343.4894 |
| 130 | | 422.4537 | 422.4537 |

TABLE 3-continued

| Compd. # | MOLSTRUCTURE | MW (Calcd.) | MW (Obs.) |
|---|---|---|---|
| 131 | | 438.4527 | 438.4527 |
| 132 | | 452.4795 | 452.4795 |
| 133 | | 408.4269 | 408.4269 |
| 134 | | 420.4626 | 420.4626 |
| 135 | | 391.4249 | 391.4249 |
| 136 | | 528.5582 | 528.5582 |
| 137 | | 435.4775 | 435.4775 |

TABLE 3-continued

| Compd. # | MOLSTRUCTURE | MW (Calcd.) | MW (Obs.) |
| --- | --- | --- | --- |
| 138 | | 419.4785 | 419.4785 |
| 139 | | 486.6126 | 486.6126 |
| 140 | | 511.547 | 511.547 |
| 141 | | 507.559 | 507.559 |
| 142 | | 505.5868 | 505.5868 |

TABLE 3-continued

| Compd. # | MOLSTRUCTURE | MW (Calcd.) | MW (Obs.) |
| --- | --- | --- | --- |
| 143 | | 574.6931 | 574.6931 |
| 144 | | 465.5222 | 465.5222 |
| 145 | | 437.4686 | 437.4686 |
| 146 | | 480.9931 | 480.9931 |
| 147 | | 518.6106 | 518.6106 |

TABLE 3-continued

| Compd. # | MOLSTRUCTURE | MW (Calcd.) | MW (Obs.) |
| --- | --- | --- | --- |
| 148 | | 535.0845 | 535.0845 |
| 149 | | 460.5748 | 460.5748 |
| 150 | | 548.6553 | 548.6553 |
| 151 | | 520.6017 | 520.6017 |
| 152 | | 446.548 | 446.548 |

TABLE 3-continued

| Compd. # | MOLSTRUCTURE | MW (Calcd.) | MW (Obs.) |
| --- | --- | --- | --- |
| 153 | | 450.4677 | 450.4677 |
| 154 | | 494.5639 | 494.5639 |
| 155 | | 511.0189 | 511.0189 |
| 156 | | 606.6911 | 606.6911 |
| 157 | | 521.5858 | 521.5858 |

TABLE 3-continued
| Compd. # | MOLSTRUCTURE | MW (Calcd.) | MW (Obs.) |
|---|---|---|---|
| 158 | 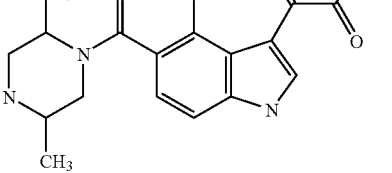 | 490.6006 | 490.6006 |
| 159 | 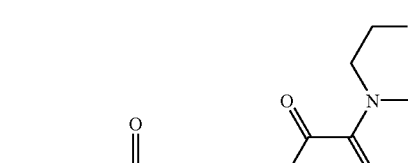 | 506.5749 | 506.5749 |
| 160 | 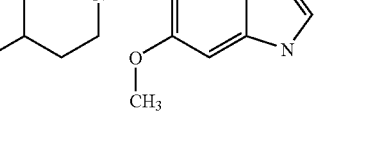 | 490.6006 | 490.6006 |
| 161 | 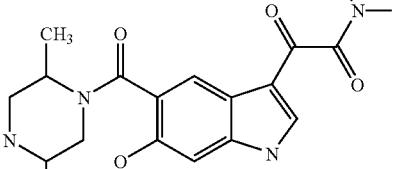 | 536.6007 | 536.6007 |
| 162 | 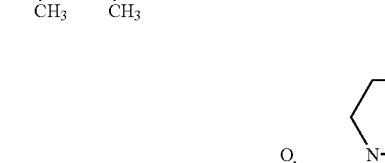 | 498.9832 | 498.9832 |

TABLE 3-continued

| Compd. # | MOLSTRUCTURE | MW (Calcd.) | MW (Obs.) |
| --- | --- | --- | --- |
| 163 | | 469.9415 | 469.9415 |
| 164 | | 541.02 | 541.02 |
| 165 | | 51.9783 | 511.9783 |
| 166 | | 497.9951 | 497.9951 |
| 167 | | 497.9951 | 497.9951 |
| 168 | | 483.9683 | 483.9683 |

TABLE 3-continued

| Compd. # | MOLSTRUCTURE | MW (Calcd.) | MW (Obs.) |
| --- | --- | --- | --- |
| 169 | | 539.0478 | 539.0478 |
| 170 | | 549.6434 | 549.6434 |
| 171 | | 476.5738 | 476.5738 |
| 172 | | 476.5738 | 476.5738 |
| 173 | | 476.5738 | 476.5738 |

TABLE 3-continued
| Compd. # | MOLSTRUCTURE | MW (Calcd.) | MW (Obs.) |
|---|---|---|---|
| 174 | 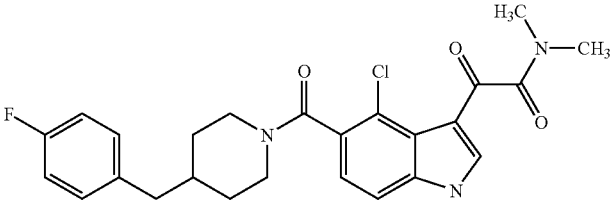 | 469.9415 | 469.9415 |
| 175 | 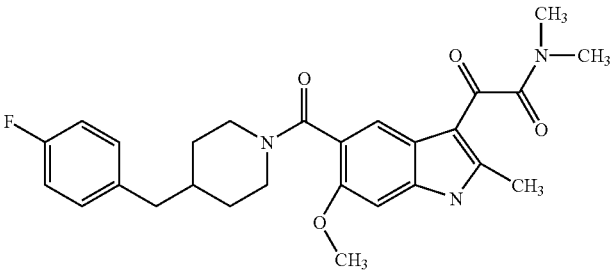 | 479.549 | 479.549 |
| 176 | 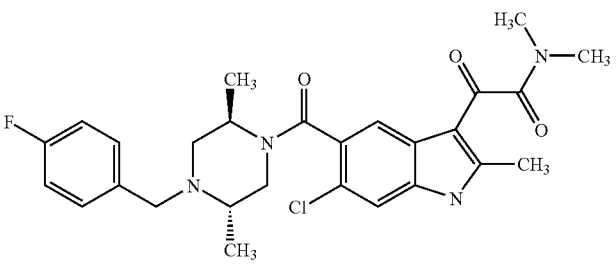 | 513.01 | 513.01 |
| 177 | 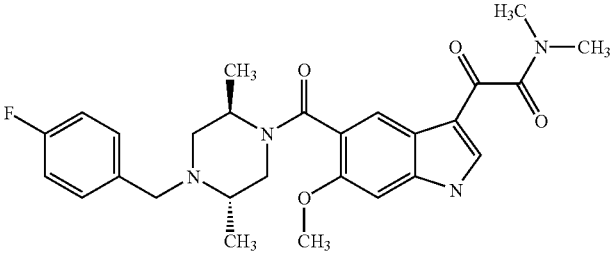 | 494.5639 | 494.5639 |
| 178 | 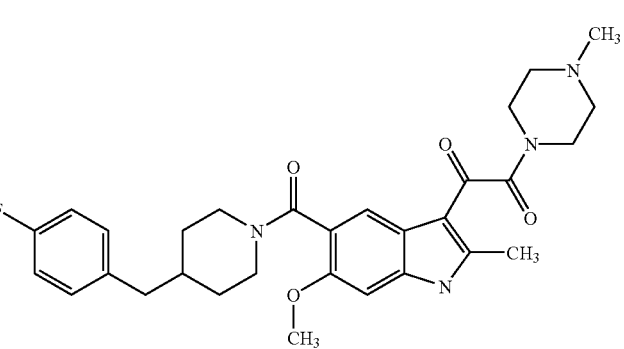 | 534.6285 | 534.6285 |

TABLE 3-continued

| Compd. # | MOLSTRUCTURE | MW (Calcd.) | MW (Obs.) |
|---|---|---|---|
| 179 | | 508.5907 | 508.5907 |
| 180 | | 522.6175 | 522.6175 |
| 181 | | 483.5123 | 483.5123 |
| 182 | | | |

The invention claimed is:

1. A compound of the formula:

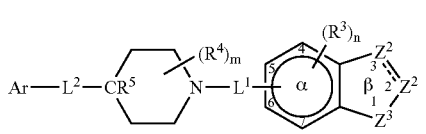

(1)

or a pharmaceutically acceptable salt thereof, wherein

⁝⁝⁝ represents a single or double bond;

one $Z^2$ is CA or $CR^8A$ and the other is $CR^1$, $CR^1{}_2$, $NR^6$ or N wherein each $R^1$ is independently hydrogen or is alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl, aryl, heteroalkyl, heteroalkenyl or heteroaryl;

$R^6$ is H, alkyl, alkenyl, alkynyl, aryl, arylalkyl, acyl, aroyl, heteroaryl, heteroalkyl, heteroalkenyl, heteroalkynyl, heteroalkylaryl, or is SOR, $SO_2R$, RCO, COOR, alkyl-COR, $SO_3R$, $CONR_2$, $SO_2NR_2$, CN, $CF_3$, or $R_3Si$ wherein each R is independently H, alkyl, alkenyl, aryl, heteroalkyl, heteroalkenyl or heteroaryl;

$R^8$ is H, halo, alkyl or alkenyl;

A is $—W_i—COX_jY$ wherein Y is $COR^2$ wherein $R^2$ is hydrogen or is straight or branched chain alkyl, alkenyl, alkynyl, aryl, arylalkyl, heteroalkyl, heteroaryl, or heteroarylalkyl, each optionally substituted with halo, alkyl, SR, OR, $NR_2$, OCOR, NRCOR, $NRCONR_2$, $NRSO_2R$, $NRSO_2NR_2$, $OCONR_2$, CN, COOR, $CONR_2$, COR, or $R_3Si$ wherein each R is independently H, alkyl, alkenyl aryl, heteroalkyl, heteroalkenyl or heteroaryl; or wherein $R^2$ is OR, $NR_2$, $NRCONR_2$, $OCONR_2$, $NRSO_2NR_2$, heteroarylalkyl, COOR, $NRNR_2$, heteroaryl, heteroaryloxy, heteroaryl-NR or NROR wherein each R is independently H, alkyl, alkenyl, aryl, heteroalkyl, heteroalkenyl or heteroaryl, and wherein two R attached to the same N atom may form a 3–8 member ring and wherein said ring may be further substituted by alkyl, alkenyl, alkynyl, aryl, arylalkyl, heteroalkyl, heteroaryl, heteroarylalkyl, each optionally substituted with halo, SR, OR, $NR_2$, OCOR, NRCOR, $NRCONR_2$, $NRSO_2R$, $NRSO_2NR_2$, $OCONR_2$, or $R_3Si$ wherein each R is independently H, alkyl, alkenyl, aryl, heteroalkyl, heteroalkenyl or heteroaryl wherein two R attached to the same N atom may form a 3–8 member ring, optionally substituted as above defined, or Y is tetrazole; 1,2,3-triazole; 1,2,4-triazole; or imidazole, and each of W and X is substituted or unsubstituted alkylene, alkenylene or alkynylene, each of 2–6 Å and each of i and j is independently 0 or 1;

$Z^3$ is $NR^7$ or O;

$R^7$ is H or is alkyl, alkenyl, alkynyl, aryl, arylalkyl, acyl, aroyl, heteroaryl, heteroalkyl, heteroalkenyl, heteroalkynyl, heteroalkylaryl, or is SOR, $SO_2R$, RCO, COOR, alkyl-COR, $SO_3R$, $CONR_2$, $SO_2NR_2$, CN, $CF_3$, $NR_2$, OR, alkyl-SR, alkyl-SOR, alkyl-$SO_2R$, alkyl-OCOR, alkyl-COOR, alkyl-CN, alkyl-$CONR_2$, or $R_3Si$, wherein each R is independently H, alkyl, alkenyl, aryl, heteroalkyl, heteroalkenyl or heteroaryl;

each $R^3$ is independently halo, alkyl, OCOR, OR, NRCOR, SR, or $NR_2$, wherein R is H, alkyl, aryl, heteroalkyl, heteroalkenyl or heteroaryl;

n is 0–3;

$L^1$ is CO, $SO_2$ or alkylene (1–4C)

$L^2$ is alkylene (1–4C) or alkenylene (2–4C) optionally substituted with one or two moieties selected from the group consisting of alkyl, alkenyl, alkynyl, aryl, arylalkyl, acyl, aroyl, heteroalkyl, heteroalkenyl, heteroalkynyl, heteroalkylaryl, heteroaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-COOR, $SO_3R$, $CONR_2$, $SO_2NR_2$, $NRSO_2NR_2$, CN, $CF_3$, and $R_3Si$, wherein each R is independently H, alkyl, alkenyl, aryl, heteroalkyl, heteroalkenyl or heteroaryl, and wherein two substituents on $L^2$ can be joined to form a non-aromatic saturated or unsaturated ring that includes 0–3 heteroatoms which are O, S and/or N and which contains 3 to 8 members or said two substituents can be joined to form a carbonyl moiety or an oxime, oximeether, oximeester or ketal of said carbonyl moiety;

each $R^4$ is independently selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl, aryl, heteroalkyl, heteroalkenyl or heteroaryl, and two of $R^4$ on adjacent positions can be joined to form a fused, optionally substituted aromatic or non-aromatic, saturated or unsaturated ring which contains 3–8 members, or $R^4$ is =O or an oxime, oximeether, oximeester or ketal thereof;

m is 0–4;

$R^5$ is hydrogen or is halo, alkyl, an amine, a thioalkoxy, aryl, arylalkyl, aryloxy, heteroaryl, acyl, carboxy or hydroxy; and Ar is an aryl group substituted with 0–5 substituents selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl, aryl, heteroalkyl, heteroalkenyl or heteroaryl, and wherein two of said optional substituents on adjacent positions can be joined to form a fused, optionally substituted aromatic or nonaromatic, saturated or unsaturated ring which contains 3–8 members.

2. The compound of claim 1 wherein i is 0.

3. The compound of claim 1 wherein Y is tetrazole; 1,2,3-triazole; 1,2,4-triazole; or imidazole.

4. The compound of claim 2 wherein j is 0.

5. The compound of claim 1 wherein $Z^3$ is $NR^7$.

6. The compound of claim 1 wherein $R^7$ is H, or is optionally substituted alkyl or acyl.

7. The compound of claim 1 wherein $L^1$ is CO.

8. The compound of claim 1 wherein $R^5$ is H, OR, $NR_2$, SR or halo, wherein each R is independently H, alkyl, alkenyl or aryl.

9. The compound of claim 1 wherein $L^2$ is unsubstituted alkylene.

10. The compound of claim 1 wherein $L^2$ is unsubstituted methylene, methylene substituted with alkyl, or —CH=.

11. The compound of claim 1 wherein Ar is optionally substituted phenyl.

12. The compound of claim 11 wherein said optional substitution is by halo, OR, or alkyl.

13. The compound of claim 12 wherein said phenyl is unsubstituted or has a single substituent.

14. The compound of claim 1 wherein each $R^4$ is halo, OR, or alkyl.

15. The compound of claim 14 wherein m is 0, 1, or 2.

16. The compound of claim 15 wherein m is 2 and both $R^4$ are alkyl.

17. The compound of claim 1 wherein $R^3$ is halo or alkoxy.

18. The compound of claim 17 wherein n is 0, 1 or 2.

19. The compound of claim 1 wherein $L^1$ is coupled to the a ring at the 4-, 5- or 6-position.

20. The compound of claim 1 wherein $Z^2$ position 3 is CA or $CH^1A$.

21. The compound of claim 20 wherein the $Z^2$ at position 2 is $CR^1$ or $CR^1{}_2$.

22. The compound of claim 21 wherein each $R^1$ is selected from the group consisting of H, alkyl, acyl, aryl, arylalkyl, heteroaryl, halo, OR, $NR_2$, SR, NRCOR, alkyl-COOR, RCO, COOR, and CN, wherein each R is independently H, alkyl, or aryl.

23. The compound of claim 20 wherein $Z^2$ at position 2 is N or $NR^6$.

24. The compound of claim 1 wherein  represents a double bond.

25. The compound of claim 1 wherein $R^2$ is hydrogen or is straight or branched chain alkyl, alkenyl, alkynyl, aryl, arylalkyl, heteroaryl, or heteroarylalkyl, each optionally substituted with halo, alkyl, SR, OR, $NR_2$, OCOR, NRCOR, $NRCONR_2$, $NRSO_2R$, $NRSO_2NR_2$, $OCONR_2$, CN, COOR, $CONR_2$, COR, or $R_3Si$ wherein each R is independently H, alkyl, alkenyl or aryl; or wherein $R^2$ is OR, $NR_2$, $NRCONR_2$, $OCONR_2$, $NRSO_2NR_2$, heteroarylalkyl, COOR, $NRNR_2$, heteroaryl, heteroaryloxy, heteroaryl-NR or NROR wherein each R is independently H, alkyl, alkenyl or aryl, and wherein two R attached to the same N atom may form a 3–8 member ring selected from the group consisting of a piperazine ring, a morpholine ring, a thiazolidine ring, an oxazolidine ring, a pyrrolidine ring, a piperidine ring, an azacyclopropane ring, an azacyclobutane ring and an azacyclooctane ring; and wherein said ring may further be substituted by alkyl, alkenyl, alkynyl, aryl, arylalkyl, heteroaryl, or heteroarylalkyl, each optionally substituted with halo, SR, OR, $NR_2$, OCOR, NRCOR, $NRCONR_2$, $NRSO_2R$, $NRSO_2NR_2$, $OCONR_2$, or $R_3Si$ wherein each R is independently H, alkyl, alkenyl or aryl wherein two R attached to the same N atom may form a 3–8 member ring, optionally substituted as above defined.

26. The compound of claim 1 wherein $Z^3$ is $NR^7$ and $R^7$ is H or is alkyl, alkenyl, alkynyl, aryl, arylalkyl, acyl, aroyl, heteroaryl, or is SOR, $SO_2R$, RCO, COOR, alkyl-COR, $SO_3R$, $CONR_2$, $SO_2NR_2$, CN, $CF_3$, $NR_2$, OR, alkyl-SR, alkyl-SOR, alkyl-$SO_2R$, alkyl-OCOR, alkyl-COOR, alkyl-CN, alkyl-$CONR_2$, or $R_3Si$, wherein each R is independently H, alkyl, alkenyl or aryl or $R^7$ is methoxymethyl, methoxyethyl, ethoxymethyl, benzyloxymethyl or 2-methoxyethoxymethyl.

27. The compound of claim 5 wherein $R^2$ is hydrogen or is straight or branched chain alkyl, alkenyl, alkynyl, aryl, arylalkyl, heteroaryl, or heteroarylalkyl, each optionally substituted with halo, alkyl, SR, OR, $NR_2$, OCOR, NRCOR, $NRCONR_2$, $NRSO_2R$, $NRSO_2NR_2$, $OCONR_2$, CN, COOR, $CONR_2$, COR, or $R_3Si$ wherein each R is independently H, alkyl, alkenyl or aryl; or
    wherein $R^2$ is OR, $NR_2$, $NRCONR_2$, $OCONR_2$, $NRSO_2NR_2$, heteroarylalkyl, COOR, $NRNR_2$, heteroaryl, heteroaryloxy, heteroaryl-NR or NROR wherein each R is independently H, alkyl, alkenyl or aryl, and wherein two R attached to the same N atom may form a 3–8 member ring selected from the group consisting of a piperazine ring, a morpholine ring, a thiazolidine ring, an oxazolidine ring, a pyrrolidine ring, a piperidine ring, an azacyclopropane ring, an azacyclobutane ring and an azacyclooctane ring; and wherein said ring may further be substituted by alkyl, alkenyl, alkynyl, aryl, arylalkyl, heteroaryl, or heteroarylalkyl, each optionally substituted with halo, SR, OR, $NR_2$, OCOR, NRCOR, $NRCONR_2$, $NRSO_2R$, $NRSO_2NR_2$, $OCONR_2$, or $R_3Si$ wherein each R is independently H, alkyl, alkenyl or aryl wherein two R attached to the same N atom may form a 3–8 member ring, optionally substituted as above defined.

28. The compound of claim 1 wherein the compound of formula (1) is selected from the group consisting of compounds shown in Tables 2 and 3 herein as compounds 1–14, 16, 18–32, 35–37, 39–44, 49–55, 58, 62, 64–66, 68–76, 78–82, 84–88, 90–91, 93–95, 97–99, 101, 103–134, 136, 140–145, 147, 150–151, 156–157, 159, 163, 165–169, 174–175, 178 and 181–182, i.e., 1: {5-[4-(4-Fluoro-benzyl)-piperidine-1-carbonyl]-6-methoxy-1-methyl-1H-indol-3-yl}-oxo-acetic acid methyl ester;

2: {5-[4-(4-Fluoro-benzyl)-piperidine-1-carbonyl]-6-methoxy-1-methyl-1H-indol-3-yl}-oxo-acetic acid;

3: 1-{5-[4-(4-Fluoro-benzyl)-piperidine-1-carbonyl]-6-methoxy-1-methyl-1H-indol-3-yl}-2-(4-methylpiperazin-1-yl)-ethane-1,2-dione;

4: [5-(4-Benzyl-piperidine-1-carbonyl)-1-(4-chloro-benzoyl)-6-methoxy-1H-indol-3-yl]-oxo-acetic acid methyl ester;

5: {5-[4-(4-Fluoro-benzyl)-piperidine-1-carbonyl]-6-methoxy-1-methyl-1H-indol-3-yl}-oxo-acetic acid ethyl ester;

6: [5-(4-Benzyl-piperidine-1-carbonyl)-1-methyl-1H-indol-3-yl]-oxo-acetic acid methyl ester;

7: 1-{5-[4-(4-Chloro-benzyl)-piperidine-1-carbonyl]-6-methoxy-1-methyl-1H-indol-3-yl}-2-(4-methylpiperazin-1-yl)-ethane-1,2-dione;

8: 5-[4-(4-Fluoro-benzyl)-piperidine-1-carbonyl]-6-methoxy-3-methoxyoxalyl-indole-1-carboxylic acid ethyl ester;

9: 5-(4-Benzyl-4-hydroxy-piperidine-1-carbonyl)-6-methoxy-3-[2-(4-methyl-piperazin-1-yl)-2-oxo-acetyl]-indole-1-carboxylic acid ethyl ester;

10: 1-{5-[4-(4-Fluoro-benzyl)-piperidine-1-carbonyl]-6-methoxy-1-methyl-1H-indol-3-yl}-2-piperazin-1-yl-ethane-1,2-dione;

11: 4-(2-{5-[4-(4-Fluoro-benzyl)-piperidine-1-carbonyl]-6-methoxy-1-methyl-1H-indol-3-yl}-2-oxo-acetyl)-piperazine-1-carboxylic acid tert-butyl ester;

12: 4-(2-{5-[4-(4-Fluoro-benzyl)-piperidine-1-carbonyl]-6-methoxy-1-methyl-1H-indol-3-yl}-2-oxo-acetyl)-piperazine-1-carboxylic acid ethyl ester;

13: 5-[4-(4-Fluoro-benzyl)-piperidine-1-carbonyl]-6-methoxy-3-(2-morpholin-4-yl-2-oxo-acetyl)-indole-1-carboxylic acid ethyl ester;

14: N-(2-Dimethylamino-ethyl)-2-{5-[4-(4-fluoro-benzyl)-piperidine-1-carbonyl]-6-methoxy-1-methyl-1H-indol-3-yl}-2-oxo-acetamide;

16: 2-{6-Chloro-5-[4-(4-fluoro-benzyl)-piperidine-1-carbonyl]-1-methyl-1H-indol-3-yl}-N,N-dimethyl-2-oxo-acetamide;

18: 5-[4-(4-Fluoro-benzyl)-piperidine-1-carbonyl]-6-methoxy-3-[2-(4-methyl-piperazin-1-yl)-2-oxo-acetyl]-indole-1-carboxylic acid ethyl ester;

19: 3-Dimethylaminooxalyl-5-[4-(4-fluoro-benzyl)-piperidine-1-carbonyl]-6-methoxy-indole-1-carboxylic acid ethyl ester;

20: 1-{6-Chloro-5-[4-(4-fluoro-benzyl)-piperidine-1-carbonyl]-1-methyl-1H-indol-3-yl}-2-morpholin-4-yl-ethane-1,2-dione;

21: 3-[2-(4-tert-Butoxycarbonyl-piperazin-1-yl)-2-oxo-acetyl]-5-[4-(4-fluoro-benzyl)-piperidine-1-carbonyl]-6-methoxy-indole-1-carboxylic acid ethyl ester;

22: 5-[4-(4-Fluoro-benzyl)-piperidine-1-carbonyl]-6-methoxy-3-(2-oxo-2-piperazin-1-yl-acetyl)-indole-1-carboxylic acid ethyl ester;

23: 1-{5-[4-(4-Fluoro-benzyl)-piperidine-1-carbonyl]-6-methoxy-1-methyl-1H-indol-3-yl}-2-morpholin-4-yl-ethane-1,2-dione;

24: 3-[2-(4-Ethoxycarbonyl-piperazin-1-yl)-2-oxo-acetyl]-5-[4-(4-fluoro-benzyl)-piperidine-1-carbonyl]-6-methoxy-indole-1-carboxylic acid ethyl ester;

25: 2-{5-[4-(4-Fluoro-benzyl)-piperidine-1-carbonyl]-6-methoxy-1-methyl-1H-indol-3-yl}-N,N-dimethyl-2-oxo-acetamide;

26: 4-(2-{5-[4-(4-Fluoro-benzyl)-piperidine-1-carbonyl]-6-methoxy-1-methyl-1H-indol-3-yl}-2-oxo-acetyl)-2,5-trans-dimethyl-piperazine-1-carboxylic acid tert-butyl ester;

27: 1-(2,5-trans-Dimethyl-piperazin-1-yl)-2-{5-[4-(4-fluoro-benzyl)-piperidine-1-carbonyl]-6-methoxy-1-methyl-1H-indol-3-yl}-ethane-1,2-dione;

28: 4-(2-{5-[4-(4-Fluoro-benzyl)-piperidine-1-carbonyl]-6-methoxy-1-methyl-1H-indol-3-yl}-2-oxo-acetyl)-2,5-trans-dimethyl-piperazine-1-carboxylic acid ethyl ester;

29: 6-Chloro-5-[4-(4-fluoro-benzyl)-piperidine-1-carbonyl]-3-[2-(4-methyl-piperazin-1-yl)-2-oxo-acetyl]-indole-1-carboxylic acid ethyl ester;

30: 1-{6-Chloro-5-[4-(4-fluoro-benzyl)-piperidine-1-carbonyl]-1-methyl-1H-indol-3-yl}-2-(4-methyl-piperazin-1-yl)-ethane-1,2-dione;

31: 1-{5-[4-(4-Flouro-benzyl)-piperidine-1-carbonyl]-1,2-dimethyl-1H-indol-3-yl}-2-(4-methyl-piperazin-1-yl)-ethane-1,2-dione;

32: 1-{6-Chloro-5-[4-(4-fluoro-benzyl)-piperidine-1-carbonyl]-1,2-dimethyl-1H-indol-3-yl}-2-(4-methyl-piperazin-1-yl)-ethane-1,2-dione;

35: 5-[4-(4-Fluoro-benzyl)-piperidine-1-carbonyl]-6-methoxy-3-[2-(4-methyl-piperazin-1-yl)-2-oxo-acetyl]-indole-1-carboxylic acid dimethylamide;

36: 6-Chloro-5-[4-(4-fluoro-benzyl)-piperidine-1-carbonyl]-3-[2-(4-methyl-piperazin-1-yl)-2-oxo-acetyl]-indole-1-carboxylic acid dimethylamide;

37: 2-{6-Chloro-1-ethoxycarbonyl-5-[4-(4-fluoro-benzyl)-piperidine-1-carbonyl]-1H-indol-3-yl}-N,N-dimethyl-2-oxo-acetamide;

39: 2-{6-Chloro-1-dimethylaminocarbonyl-5-[4-(4-fluoro-benzyl)-piperidine-1-carbonyl]-1H-indol-3-yl}-N,N-dimethyl-2-oxo-acetamide;

40: 2-{6-Chloro-1-cyano-5-[4-(4-fluoro-benzyl)-piperidine-1-carbonyl]-1H-indol-3-yl}-N,N-dimethyl-2-oxo-acetamide;

41: 2-{6-Chloro-5-[4-(4-fluoro-benzyl)-piperidine-1-carbonyl]-1-methanesulfonyl-1H-indol-3-yl}-N,N-dimethyl-2-oxo-acetamide;

42: 6-Chloro-3-dimethylaminooxalyl-5-[4-(4-fluoro-benzyl)-piperidine-1-carbonyl]-indole-1-carboxylic acid tert-butyl ester;

43: 2-{6-Chloro-5-[4-(4-fluoro-benzyl)-piperidine-1-carbonyl]-1-methoxymethyl-1H-indol-3-yl}-N,N-dimethyl-2-oxo-acetamide;

44: 2-{1-Cyano-5-[4-(4-fluoro-benzyl)-piperidine-1-carbonyl]-6-methoxy-1H-indol-3-yl}-N,N-dimethyl-2-oxo-acetamide;

49: 3-Dimethylaminooxalyl-5-[4-(4-fluoro-benzyl)-piperidine-1-carbonyl]-6-methoxy-indole-1-carboxylic acid dimethylamide;

50: 2-{5-[4-(4-Fluoro-benzyl)-piperidine-1-carbonyl]-1-methanesulfonyl-6-methoxy-1H-indol-3-yl}-N,N-dimethyl-2-oxo-acetamide;

51: 2-{5-[4-(4-Fluoro-benzyl)-piperidine-1-carbonyl]-6-methoxy-1-methoxymethyl-1H-indol-3-yl}-N,N-dimethyl-2-oxo-acetamide;

52: 2-{1-Acetyl-5-[4-(4-fluoro-benzyl)-piperidine-1-carbonyl]-6-methoxy-1H-indol-3-yl}-N,N-dimethyl-2-oxo-acetamide;

53: 2-{1-Dimethylsulfamoyl-5-[4-(4-fluoro-benzyl)-piperidine-1-carbonyl]-6-methoxy-1H-indol-3-yl}-N,N-dimethyl-2-oxo-acetamide;

54: 3-Dimethylaminooxalyl-5-[4-(4-fluoro-benzyl)-piperidine-1-carbonyl]-6-methoxy-indole-1-carboxylic acid tert-butyl ester;

55: 1-{5-[4-(4-Fluoro-benzyl)-piperidine-1-carbonyl]-1-methanesulfonyl-6-methoxy-1H-indol-3-yl}-2-(4-methyl-piperazin-1-yl)-ethane-1,2-dione;

58: 2-{6-Chloro-5-[4-(4-fluoro-benzyl)-piperidine-1-carbonyl]-1-methyl-1H-indol-3-yl}-2-oxo-acetamide;

62: 2-{6-Chloro-5-[4-(4-fluoro-benzyl)-piperidine-1-carbonyl]-1-methoxymethyl-1H-indol-3-yl}-N-methyl-2-oxo-acetamide;

64: 2-{1-tert-butoxycarbonylmethyl-6-Chloro-5-[4-(4-fluoro-benzyl)-piperidine-1-carbonyl]-1H-indol-3-yl}-N,N-dimethyl-2-oxo-acetamide;

65: 2-{5-[4-(4-fluoro-benzyl)-piperidine-1-carbonyl]-6-methoxy-1-methyl-1H-indol-3-yl}-N-ethyl-N-methyl-2-oxo-acetamide;

66: 2-{6-Ethoxy-5-[4-(4-fluoro-benzyl)-piperidine-1-carbonyl]-1-methyl-1H-indol-3-yl}-N,N-dimethyl-2-oxo-acetamide;

68: {6-Chloro-3-dimethylaminooxalyl-5-[4-(4-fluoro-benzyl)-piperidine-1-carbonyl]-indol-1-yl}-acetic acid methyl ester;

69: 2,2-Dimethyl-propionic acid 6-chloro-3-dimethylaminooxalyl-5-[4-(4-fluoro-benzyl)-piperidine-1-carbonyl]-indol-1-ylmethyl ester;

70: 2-{6-Chloro-5-[4-(4-fluoro-benzyl)-piperidine-1-carbonyl]-1-methylthiomethyl-1H-indol-3-yl}-N,N-dimethyl-2-oxo-acetamide;

71: 2-{6-Chloro-5-[4-(4-fluoro-benzyl)-piperidine-1-carbonyl]-1-methyl-1H-indol-3-yl}-N,N-diethyl-2-oxo-acetamide;

72: 2-{6-Chloro-5-[4-(4-fluoro-benzyl)-piperidine-1-carbonyl]-1-methyl-1H-indol-3-yl}-N-(2-cyano-ethyl)-N-methyl-2-oxo-acetamide;

73: 2-{6-Chloro-5-[4-(4-fluoro-benzyl)-piperidine-1-carbonyl]-1-methyl-1H-indol-3-yl}-2-oxo-N-thiazol-2-yl-acetamide;

74: 1-Azetidin-1-yl-2-{6-chloro-5-[4-(4-fluoro-benzyl)-piperidine-1-carbonyl]-1H-indol-3-yl}-ethane-1,2-dione;

75: 2-{6-Chloro-5-[4-(4-fluoro-benzyl)-piperidine-1-carbonyl]-1-isopropyl-1H-indol-3-yl}-N,N-dimethyl-2-oxo-acetamide;

76: 2-[6-Chloro-5-[4-(4-fluoro-benzyl)-piperidine-1-carbonyl]-1-(2-methoxy-ethyl)-1H-indol-3-yl]-N,N-dimethyl-2-oxo-acetamide;

78: 2-{6-Chloro-5-[4-(4-fluoro-benzyl)-piperidine-1-carbonyl]-1-methyl-1H-indol-3-yl}-N-isopropyl-N-methyl-2-oxo-acetamide;

79: 2-{6-Chloro-5-[4-(4-fluoro-benzyl)-piperidine-1-carbonyl]-1-methyl-1H-indol-3-yl}-N-cyclopropylmethyl-N-propyl-2-oxo-acetamide;

80: 2-{6-Chloro-5-[4-(4-fluoro-benzyl)-piperidine-1-carbonyl]-1-methyl-1H-indol-3-yl}-N-ethyl-N-methyl-2-oxo-acetamide;

81: 2-{6-Chloro-5-[4-(4-fluoro-benzyl)-piperidine-1-carbonyl]-1-methyl-1H-indol-3-yl}-N-cyclopropyl-2-oxo-acetamide;

82: 2-{6-Chloro-5-[4-(4-fluoro-benzyl)-piperidine-1-carbonyl]-1-methyl-1H-indol-3-yl}-2-oxo-N-pyrrolidin-1-yl-acetamide;

84: 1-{6-Chloro-5-[4-(4-fluoro-benzyl)-piperidine-1-carbonyl]-1-methyl-1H-indol-3-yl}-2-pyrrolidin-1-yl-ethane-1,2-dione;

85: 2-{6-Chloro-5-[4-(4-fluoro-benzyl)-piperidine-1-carbonyl]-1-methyl-1H-indol-3-yl}-N,N-diisopropyl-2-oxo-acetamide;

86: 2-{6-Chloro-5-[4-(4-fluoro-benzyl)-piperidine-1-carbonyl]-1-methyl-1H-indol-3-yl}-N-methoxy-2-oxo-acetamide;

87: 1-{6-Chloro-5-[4-(4-fluoro-benzyl)-piperidine-1-carbonyl]-1-methyl-1H-indol-3-yl}-2-(2-methyl-aziridin-1-yl)-ethane-1,2-dione;

88: 1-Azocan-1-yl-2-{6-chloro-5-[4-(4-fluoro-benzyl)-piperidine-1-carbonyl]-1-methyl-1H-indol-3-yl}-ethane-1,2-dione;

90: 2-{6-Chloro-5-[4-(4-fluoro-benzyl)-piperidine-1-carbonyl]-1-methanesulfonylmethyl-1H-indol-3-yl}-N,N-dimethyl-2-oxo-acetamide;

91: 2-[6-Chloro-5-[4-(4-fluoro-benzyl)-piperidine-1-carbonyl]-1-(2-methoxy-ethoxymethyl)-1H-indol-3-yl]-N,N-dimethyl-2-oxo-acetamide;

93: 2-{1-Acetoxymethyl-6-chloro-5-[4-(4-fluoro-benzyl)-piperidine-1-carbonyl]-1H-indol-3-yl}-N,N-dimethyl-2-oxo-acetamide;

94: 2-{1-Benzyloxymethyl-6-chloro-5-[4-(4-fluoro-benzyl)-piperidine-1-carbonyl]-1H-indol-3-yl}-N,N-dimethyl-2-oxo-acetamide;

95: 2-{6-Chloro-1-ethoxymethyl-5-[4-(4-fluoro-benzyl)-piperidine-1-carbonyl]-1H-indol-3-yl}-N,N-dimethyl-2-oxo-acetamide;

97: 2-{6-Chloro-5-[4-(4-fluoro-benzyl)-piperidine-1-carbonyl]-1-methyl-1H-indol-3-yl}-N-cyclopropyl-N-methyl-2-oxo-acetamide;

98: 2-{5-[4-Fluoro-4-(4-fluoro-benzyl)-piperidine-1-carbonyl]-6-methoxy-1-methyl-1H-indol-3-yl}-N,N-dimethyl-2-oxo-acetamide;

99: 2-{5-[4-Fluoro-4-(4-fluoro-benzyl)-piperidine-1-carbonyl]-6-methoxy-1-methoxymethyl-1H-indol-3-yl}-N,N-dimethyl-2-oxo-acetamide;

101: 2-{6-Chloro-1-(2-diethylamino-ethyl)-5-[4-(4-fluoro-benzyl)-piperidine-1-carbonyl]-1H-indol-3-yl}-N,N-dimethyl-2-oxo-acetamide;

103: 2-{6-Chloro-5-[4-(4-fluoro-benzyl)-piperidine-1-carbonyl]-1-methyl-1H-indol-3-yl}-N-ethyl-2-oxo-N-propyl-acetamide;

104: 1-{6-Chloro-5-[4-(4-fluoro-benzyl)-piperidine-1-carbonyl]-1-methyl-1H-indol-3-yl}-2-thiazolidin-3-yl-ethane-1,2-dione;

105: 2-{6-Chloro-5-[4-(4-fluoro-benzyl)-piperidine-1-carbonyl]-1-methyl-1H-indol-3-yl}-N-ethyl-N-isopropyl-2-oxo-acetamide;

106: 1-{6-Chloro-5-[4-(4-fluoro-benzyl)-piperidine-1-carbonyl]-1-methyl-1H-indol-3-yl}-2-(4,4-dimethyl-oxazolidin-3-yl)-ethane-1,2-dione;

107: 1-{6-Chloro-5-[4-(4-fluoro-benzyl)-piperidine-1-carbonyl]-1-methyl-1H-indol-3-yl}-2-(2,5-dimethyl-pyrrolidin-1-yl)-ethane-1,2-dione;

108: {6-Chloro-5-[4-(4-fluoro-benzyl)-piperidine-1-carbonyl]-1-methyl-1H-indol-3-yl}-oxo-acetic acid N',N'-dimethyl-hydrazide;

109: 1-{6-Chloro-5-[4-(4-fluoro-benzyl)-piperidine-1-carbonyl]-1-methyl-1H-indol-3-yl}-2-piperidin-1-yl-ethane-1,2-dione;

110: 2-{6-Chloro-5-[4-(4-fluoro-benzyl)-piperidine-1-carbonyl]-1-methyl-1H-indol-3-yl}-N-ethyl-N-(2-methoxy-ethyl)-2-oxo-acetamide;

111: 2-{6-Chloro-5-[4-(4-fluoro-benzyl)-piperidine-1-carbonyl]-1-methyl-1H-indol-3-yl}-N-(2-methylsulfanyl-ethyl)-2-oxo-acetamide;

112: 2-{6-Chloro-5-[4-(4-fluoro-benzyl)-piperidine-1-carbonyl]-1-methyl-1H-indol-3-yl}-N-methoxy-N-methyl-2-oxo-acetamide;

113: 2-{6-Chloro-5-[4-(4-fluoro-benzyl)-piperidine-1-carbonyl]-1-methyl-1H-indol-3-yl}-N-cyanomethyl-N-methyl-2-oxo-acetamide;

114: [(2-{6-Chloro-5-[4-(4-fluoro-benzyl)-piperidine-1-carbonyl]-1-methyl-1H-indol-3-yl}-2-oxo-acetyl)-methyl-amino]-acetic acid methyl ester;

115: 2-{1-Cyanomethyl-5-[4-(4-fluoro-benzyl)-piperidine-1-carbonyl]-6-methoxy-1H-indol-3-yl}-N,N-dimethyl-2-oxo-acetamide;

116: [6-Chloro-1-methyl-3-(1-methyl-1H-imidazole-2-carbonyl)-1H-indol-5-yl]-[4-(4-fluoro-benzyl)-piperidin-1-yl]-methanone;

117: 1-[5-(4-Benzyl-piperidine-1-carbonyl)-1H-indol-3-yl]-2-(4-methyl-piperazin-1-yl)-ethane-1,2-dione;

118: [5-(4-Benzyl-piperidine-1-carbonyl)-1H-indol-3-yl]-oxo-acetic acid methyl ester;

119: [5-(4-Benzyl-piperidine-1-carbonyl)-1H-indol-3-yl]-oxo-acetic acid;

120: 1-[5-(4-Benzyl-piperidine-1-carbonyl)-6-methoxy-1H-indol-3-yl]-2-(4-methyl-piperazin-1-yl)-ethane-1,2-dione;

121: 4-{2-[5-(4-Benzyl-piperidine-1-carbonyl)-1H-indol-3-yl]-2-oxo-acetyl}-piperazine-1-carboxylic acid tert-butyl ester;

122: 1-[5-(4-Benzyl-piperidine-1-carbonyl)-1H-indol-3-yl]-2-piperazin-1-yl-ethane-1,2-dione;

123: 2-[5-(4-Benzyl-piperidine-1-carbonyl)-1H-indol-3-yl]-2-oxo-acetamide;

124: [5-(4-Benzyl-piperidine-1-carbonyl)-6-methoxy-1H-indol-3-yl]-oxo-acetic acid;

125: 2-[5-(4-Benzyl-piperidine-1-carbonyl)-6-methoxy-1H-indol-3-yl]-2-oxo-N-(2-pyrrolidin-1-yl-ethyl)-acetamide;

126: 1-{5-[4-(4-Fluoro-benzyl)-piperidine-1-carbonyl]-2-methyl-1H-indol-3-yl}-2-(4-methyl-piperazin-1-yl)-ethane-1,2-dione;

127: {5-[4-(4-Fluoro-benzyl)-piperidine-1-carbonyl]-2-methyl-1H-indol-3-yl}-oxo-acetic acid;

128: 1-{6-Chloro-5-[4-(4-fluoro-benzyl)-piperidine-1-carbonyl]-1H-indol-3-yl}-2-(4-methyl-piperazin-1-yl)-ethane-1,2-dione;

129: [5-(4-Benzyl-piperidine-1-carbonyl)-6-methoxy-1H-indol-3-yl]-oxo-acetic acid methyl ester;

130: {5-[4-(4-Fluoro-benzyl)-piperidine-1-carbonyl]-1H-indol-3-yl}-oxo-acetic acid methyl ester;

131: {5-[4-(4-Fluoro-benzyl)-piperidine-1-carbonyl]-6-methoxy-1H-indol-3-yl}-oxo-acetic acid;

132: {5-[4-(4-Fluoro-benzyl)-piperidine-1-carbonyl]-6-methoxy-1H-indol-3-yl}-oxo-acetic acid methyl ester;

133: {5-[4-(4-Fluoro-benzyl)-piperidine-1-carbonyl]-1H-indol-3-yl}-oxo-acetic acid;

134: [5-(4-Benzyl-piperidine-1-carbonyl)-4-methoxy-1H-indol-3-yl]-oxo-acetic acid;

136: [5-(4-Benzyl-piperidine-1-carbonyl)-4-methoxy-1H-indol-3-yl]-oxo-acetic acid 2-methyl-4-oxo-4H-pyran-3-yl ester;

140: N-(2,3-Dihydroxy-propyl)-2-{5-[4-(4-fluoro-benzyl)-piperidine-1-carbonyl]-6-methoxy-1H-indol-3-yl}-2-oxo-acetamide;

141: 1-{5-[4-(4-Fluoro-benzyl)-piperidine-1-carbonyl]-6-methoxy-1H-indol-3-yl}-2-morpholin-4-yl-ethane-1,2-dione;

142: 1-{5-[4-(4-Fluoro-benzyl)-piperidine-1-carbonyl]-6-methoxy-1H-indol-3-yl}-2-piperidin-1-yl-ethane-1,2-dione;

143: 1-{5-[4-(4-Fluoro-benzyl)-piperidine-1-carbonyl]-6-methoxy-1H-indol-3-yl}-2-(4-pyrrolidin-1-yl-piperidin-1-yl)-ethane-1,2-dione;

144: 2-{5-[4-(4-Fluoro-benzyl)-piperidine-1-carbonyl]-6-methoxy-1H-indol-3-yl}-N,N-dimethyl-2-oxo-acetamide;

145: 2-{5-[4-(4-Fluoro-benzyl)-piperidine-1-carbonyl]-6-methoxy-1H-indol-3-yl}-2-oxo-acetamide;

147: 1-[5-(4-Benzyl-4-hydroxy-piperidine-1-carbonyl)-6-methoxy-1H-indol-3-yl]-2-(4-methyl-piperazin-1-yl)-ethane-1,2-dione;

150: 1-{5-[4-(4-Fluoro-benzyl)-piperidine-1-carbonyl]-6-methoxy-1H-indol-3-yl}-2-(4-isopropyl-piperazin-1-yl)-ethane-1,2-dione;

151: 1-{5-[4-(4-Fluoro-benzyl)-piperidine-1-carbonyl]-6-methoxy-1H-indol-3-yl}-2-(4-methyl-piperazin-1-yl)-ethane-1,2-dione;

156: 4-(2-{5-[4-(4-Fluoro-benzyl)-piperidine-1-carbonyl]-6-methoxy-1H-indol-3-yl}-2-oxo-acetyl)-piperazine-1-carboxylic acid tert-butyl ester;

157: 1-{5-[4-(4-Fluoro-benzyl)-piperidine-1-carbonyl]-6-methoxy-1H-indol-3-yl}-2-(4-hydroxy-piperidin-1-yl)-ethane-1,2-dione;

159: 1-{5-[4-(4-Fluoro-benzyl)-piperidine-1-carbonyl]-6-methoxy-1H-indol-3-yl}-2-piperizin-1-yl-ethane-1,2-dione;

163: 2-{6-Chloro-5-[4-(4-fluoro-benzyl)-piperidine-1-carbonyl]-1H-indol-3-yl}-N,N-dimethyl-2-oxo-acetamide;

165: 1-{6-Chloro-5-[4-(4-fluoro-benzyl)-piperidine-1-carbonyl]-1H-indol-3-yl}-2-morpholin-4-yl-ethane-1,2-dione;

166: 2-{6-Chloro-5-[4-(4-fluoro-benzyl)-piperidine-1-carbonyl]-1H-indol-3-yl}-N,N-diethyl-2-oxo-acetamide;

167: 2-{6-Chloro-5-[4-(4-fluoro-benzyl)-piperidine-1-carbonyl]-1H-indol-3-yl}-N-isopropyl-N-methyl-2-oxo-acetamide;

168: 2-{6-Chloro-5-[4-(4-fluoro-benzyl)-piperidine-1-carbonyl]-2-methyl-1H-indol-3-yl}-N,N-dimethyl-2-oxo-acetamide;

169: 1-{6-Chloro-5-[4-(4-fluoro-benzyl)-piperidine-1-carbonyl]-2-methyl-1H-indol-3-yl}-2-(4-methyl-piperazin-1-yl)-ethane-1,2-dione;

174: 2-{4-Chloro-5-[4-(4-fluoro-benzyl)-piperidine-1-carbonyl]-1H-indol-3-yl}-N,N-dimethyl-2-oxo-acetamide;

175: 2-{5-[4-(4-Fluoro-benzyl)-piperidine-1-carbonyl]-6-methoxy-2-methyl-1H-indol-3-yl}-N,N-dimethyl-2-oxo-acetamide;

178: 1-{5-[4-(4-Fluoro-benzyl)-piperidine-1-carbonyl]-6-methoxy-2-methyl-1H-indol-3-yl}-2-(4-methyl-piperazin-1-yl)-ethane-1,2-diane;

181: 2-{5-[4-Fluoro-4-(4-fluoro-benzyl)-piperidine-1-carbonyl]-6-methoxy-1H-indol-3-yl}-N,N-dimethyl-2-oxo-acetamide; and 182: 2-(5-{4-[(4-Fluoro-phenyl)-methyl-amino]-piperidine-1-carbonyl}-6-methoxy-1-methyl-1H-indol-3-yl)-N,N-dimethyl-2-oxo-acetamide.

29. A pharmaceutical composition which comprises a therapeutically effective amount of the compound of claim 1 along with a pharmaceutically acceptable substituent.

30. A method to treat rheumatoid arthritis comprising administering to a subject in need of such treatment a compound of claim 1 or a pharmaceutical composition thereof.

* * * * *